United States Patent
Walensky et al.

(10) Patent No.: US 10,308,926 B2
(45) Date of Patent: Jun. 4, 2019

(54) STABLIZED EZH2 PEPTIDES

(71) Applicant: DANA-FARBER CANCER INSTITUTE, INC., Boston, MA (US)

(72) Inventors: Loren D. Walensky, Newton, MA (US); Gregory H. Bird, Pelham, NH (US); Woojin Kim, Newton, MA (US); Stuart Orkin, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/772,143

(22) PCT Filed: Mar. 13, 2014

(86) PCT No.: PCT/US2014/025587
§ 371 (c)(1),
(2) Date: Sep. 2, 2015

(87) PCT Pub. No.: WO2014/151369
PCT Pub. Date: Sep. 25, 2014

(65) Prior Publication Data
US 2016/0068834 A1    Mar. 10, 2016

Related U.S. Application Data

(60) Provisional application No. 61/790,023, filed on Mar. 15, 2013.

(51) Int. Cl.
| | |
|---|---|
| C12N 9/96 | (2006.01) |
| A61K 38/00 | (2006.01) |
| A61K 35/00 | (2006.01) |
| A61K 38/12 | (2006.01) |
| C07K 5/00 | (2006.01) |
| C07K 7/00 | (2006.01) |
| C07K 16/00 | (2006.01) |
| C07K 17/00 | (2006.01) |
| C07K 14/47 | (2006.01) |
| C12N 9/10 | (2006.01) |

(52) U.S. Cl.
CPC ............ *C12N 9/96* (2013.01); *C07K 14/47* (2013.01); *C12N 9/1007* (2013.01); *A61K 38/00* (2013.01); *C12Y 201/01043* (2013.01)

(58) Field of Classification Search
CPC ...... A61K 38/00; C07K 14/47; C12N 9/1007; C12N 9/96; C12Y 201/01043
See application file for complete search history.

(56) References Cited

U.S. PATENT DOCUMENTS

| | | |
|---|---|---|
| 5,446,090 A | 8/1995 | Harris |
| 6,348,558 B1 | 2/2002 | Harris et al. |
| 7,723,468 B2 | 5/2010 | Daffre et al. |
| 2004/0067503 A1 | 4/2004 | Tan et al. |
| 2005/0250680 A1 | 11/2005 | Walensky et al. |
| 2012/0270800 A1 | 10/2012 | Verdine et al. |

FOREIGN PATENT DOCUMENTS

| | | | |
|---|---|---|---|
| WO | WO 1999/14259 | 3/1999 | |
| WO | WO 1999/34833 | 7/1999 | |
| WO | WO 2008/121767 | 10/2008 | |
| WO | WO 2008121767 A2 * | 10/2008 | ............... C07K 7/06 |
| WO | WO 2009/108261 | 9/2009 | |
| WO | WO 2010/060112 | 5/2010 | |
| WO | WO 2010/068684 | 6/2010 | |
| WO | WO 2010/148335 | 12/2010 | |
| WO | 2012/174409 A1 | 12/2012 | |
| WO | WO 2012/174409 A1 | 12/2012 | |

OTHER PUBLICATIONS

Han et al. "Structural Basis of EZH2 Recognition by EED" Structure 15:1306-1315. Published Oct. 2007.*
Anonymous. UniProtKB—Q15910 (EZH2 Human). (Year: 1998).*
McCabe et al. "EZH2 inhibition as a therapeutic strategy for lymphoma with EZH2-activating mutations" Nature 492:108-114. (Year: 2012).*
Souroujon M and Mochly-Rosen D "Peptide modulators of protein-protein interactions in intracellular signaling" Nature Biotechnology 16:919-924. (Year: 1998).*
Altschul et al., *Gapped BLAST and PSI-BLAST: a new generation of protein database search programs*, Nucleic Acids Res. 25(17):3389-3402 (1997).
Banerjee, R. et al. *The tumor suppressor gene rap1GAP is silenced by miR-101-mediated EZH2 overexpression in invasive squamous cell carcinoma*, Oncogene 30, 4339-4349 (2011).
Bang, et al., *Total Chemical Synthesis of Crambin*, J. Am. Chem. Soc. 126:1377-1383 (2004).
Beisel, C., et al., Histone methylation by the *Drosophila* epigenetic transcriptional regulator Ash1. Nature 419, 857-862 (2002).
Beke, L., et al., *The gene encoding the prostatic tumor suppressor PSP94 is a target for repression by the Polycomb group protein EZH2*, Oncogene 26:4590-4595 (2007).
Bernal, F. et al. *A Stapled p53 Helix Overcomes HDMX-Mediated Suppression of p53*. Cancer Cell 18: 411-422 (2010).
Bird et al, *Chemical synthesis of hydrocarbon-stapled peptides for protein interaction research and therapeutic targeting*, Current Protocols in Chemical Biology, 3(3):99-117 (2011).
Bird et. al., *Synthesis and Biophysical Characterization of Stabilized alpha-Helices of BCL-2 Domains*, Methods in Enzymol., 446:369-386 (2008).
Bird, G. H. et al. *Hydrocarbon double-stapling remedies the proteolytic instability of a lengthy peptide therapeutic*. Proceedings of the National Academy of Sciences 107, 14093-14098 (2010).

(Continued)

*Primary Examiner* — Zachary J Miknis
(74) *Attorney, Agent, or Firm* — Fish & Richardson P.C.

(57) ABSTRACT

Provided herein are polypeptides containing stabilized therapeutic peptides related to enhancer of zeste homolog 2 (EZH2), histone lysine N-methyltransferase. Also provided are compositions containing these polypeptides and methods of using such peptides in the treatment of cancer that include administering to a subject one of the polypeptides.

43 Claims, 38 Drawing Sheets

Specification includes a Sequence Listing.

(56) References Cited

OTHER PUBLICATIONS

Blackwell et al., *Ring-Closing Metathesis of Olefinic Peptides: Design, Synthesis, and Structural Characterization of Macrocyclic Helical Peptides*, J. Org. Chem., 66: 5291-5302, 2001.
Borchardt, R. T., et al., *A potent inhibitor of S-adenosylhomocysteine hydrolase and of vaccinia virus multiplication in mouse L929 cells.* J. Biol. Chem. 259, 4353-4358 (1984).
Borun, T. W., et al., *Studies of histone methylation during the HeLa S-3 cell cycle.* J. Biol. Chem. 247(13):4288-4298 (1972).
Bowen, N. J., et al., *Mi-2/NuRD: multiple complexes for many purposes.* Biochim. Biophys. Acta 1677, 52-57 (2004).
Bracken, A. P. et al. *The Polycomb group proteins bind throughout the INK4A-ARF locus and are disassociated in senescent cells.* Genes & Development 21(5):525-530 (2007).
Byvoet, P., et al., *The distribution and turnover of labeled methyl groups in histone fractions of cultured mammalian cells*, Archives of Biochemistry and Biophysics 148(2):558-567 (2003).
Cao, R., *Role of Histone H3 Lysine 27 Methylation in Polycomb-Group Silencing.* Science 298:1039-1043 (2002).
Carvalho, J. et al., *Lack of microRNA-101 causes E-cadherin functional deregulation through EZH2 up-regulation in intestinal gastric cancer.* J Pathol 228(1): 31-44 (2012).
Chamberlain, S. J., et al., *Polycomb repressive complex 2 is dispensable for maintenance of embryonic stem cell pluripotency.* Stem Cells 26(6):1496-1505 (2008).
Chiang, P. K., *Biological effects of inhibitors of S-adenosylhomocysteine hydrolase.* Pharmacol. Ther. 77(2):115-134 (1998).
Czermin, B. et al. *Drosophila enhancer of Zeste/ESC complexes have a histone H3 methyltransferase activity that marks chromosomal Polycomb sites.* Cell 111(2):185-196 (2002).
Deshayes, S., et al., *Cell penetrating peptides: tools for intracellular delivery of therapeutics.* Cell. Mol. Life Sci. 62:1839-1849 (2005).
Devi et al., *Antibodies to poly[(2----8)-alpha-N-acetylneuraminic acid] and poly[(2----9)-alpha-N-acetylneuraminic acid] are elicited by immunization of mice with Escherichia coli K92 conjugates: potential vaccines for groups B and C meningococci and E. coli K1*, Proc. Natl. Acad. Sci. USA 88(16):7175-7179, (1991).
Di Tullio, et al., *CCAAT/enhancer binding protein alpha (C/EBP(alpha))-induced transdifferentiation of pre-B cells into macrophages involves no overt refrodifferentiation.* Proceedings of the National Academy of Sciences 108(41):17016-17021 (2011).
Ezhkova, E. et al. *EZH1 and EZH2 cogovern histone H3K27 trimethylation and are essential for hair follicle homeostasis and wound repair.* Genes & Development 25(5):485-498 (2011).
Fattom et al., *Serum antibody response in adult volunteers elicited by injection of Streptococcus pneumoniae type 12F polysaccharide alone or conjugated to diphtheria toxoid*, Infect. Immun., 58(7):2309-2312, (1990).
Fujii, S., et al., *Enhancer of Zeste Homologue 2 (EZH2) Down-regulates RUNX3 by Increasing Histone H3 Methylation.* Journal of Biological Chemistry 283(25):17324-17332 (2008).
Fussbroich, B. et al. *EZH2 Depletion Blocks the Proliferation of Colon Cancer Cells.* PLoS ONE 6(7): e21651 (2011).
Hambardzumyan, D., et al., *Radiation resistance and stem-like cells in brain tumors.* Cancer Cell 10(6):454-456 (2006).
Han, Z. et al. *Structural Basis of EZH2 Recognition by EED.* Structure 15(10):1306-1315 (2007).
He, L. et al. *High expression of EZH2 is associated with tumor aggressiveness and poor prognosis in patients with esophageal squamous cell carcinoma treated with definitive chemoradiotherapy.* Int. J. Cancer 127(1):138-147 (2009).
Heinz, S. et al. *Expression of the polycomb group protein EZH2 and its relation to outcome in patients with urothelial carcinoma of the bladder.* J. Cancer Res. Clin. Oncol. 134, 331-336 (2007).
Ho, L. et al., *Chromatin remodelling during development.* Nature 463(7280):474-484 (2010).
Kawamoto et al., *Design of Triazole-stapled BCL9 α-Helical Peptides to Target the β-Catenin/B-cell CLL/lymphoma 9 (BCL9) Protein-Protein Interaction*, Journal of Medicinal Chemistry 55(3):1137-1146 (2012).
Kleer, C. G. et al. *EZH2 is a marker of aggressive breast cancer and promotes neoplastic transformation of breast epithelial cells.* Proc. Natl. Acad. Sci. U.S.A. 100(20):11606-11611 (2003).
Knutson, S. K. et al. *A selective inhibitor of EZH2 blocks H3K27 methylation and kills mutant lymphoma cells.* Nature Chemical Biology 8(11):890-896 (2012).
Kong, D. et al. *Loss of let-7 up-regulates EZH2 in prostate cancer consistent with the acquisition of cancer stem cell signatures that are attenuated by BR-DIM.* PLoS ONE 7(3): e33729 (2012).
Krivtsov, A. V. et al. *Transformation from committed progenitor to leukaemia stem cell initiated by MLL-AF9.* Nature 442(7104):818-822 (2006).
Kuzmichev, A. *Histone methyltransferase activity associated with a human multiprotein complex containing the Enhancer of Zeste protein.* Genes & Development 16(22):2893-2905 (2002).
Margueron, R. et al., *The Polycomb complex PRC2 and its mark in life.* Nature 469(7330):343-349 (2011).
Margueron, R. et al. *Ezh1 and Ezh2 Maintain Repressive Chromatin through Different Mechanisms.* Molecular Cell 32(4):503-518 (2008).
McCabe et al. *EZH2 inhibition as a therapeutic strategy for lymphoma with EZH2-activating mutations*, Nature, 492(7427):108-112 (2012).
McCabe, M. T. et al. *Mutation of A677 in histone methyltransferase EZH2 in human B-cell lymphoma promotes hyperfrimethylation of histone H3 on lysine 27 (H3K27).* Proceedings of the National Academy of Sciences 109(8):2989-2994 (2012).
Miranda, T. B. et al. *DZNep is a global histone methylation inhibitor that reactivates developmental genes not silenced by DNA methylation.* Molecular Cancer Therapeutics 8(6):1579-1588 (2009).
Moellering, R. E. et al. *Direct inhibition of the NOTCH transcription factor complex.* Nature 462(7270):182-188 (2009).
Momparler, R. L., et al., *Synergistic antileukemic action of a combination of inhibitors of DNA methylation and histone methylation.* Leuk. Res. 36(8):1049-1054 (2012).
Morin, R. D. et al. *Somatic mutations altering EZH2 (Tyr641) in follicular and diffuse large B-cell lymphomas of germinal-center origin.* Nature Genetics 42(2):181-185 (2010).
Muller, J. et al. *Histone methyltransferase activity of a Drosophila Polycomb group repressor complex.* Cell 111(2):197-208 (2002).
Nagy, P. L., et al., *A trithorax-group complex purified from Saccharomyces cerevisiae is required for methylation of histone H3.* Proc. Natl. Acad. Sci. U.S.A. 99(1):90-94 (2002).
Neff, T. et al. *Polycomb repressive complex 2 is required for MLL-AF9 leukemia.* Proceedings of the National Academy of Sciences 109(13):5028-5033 (2012).
Pinto do O, P. *Hematopoietic progenitor/stem cells immortalized by Lhx2 generate functional hematopoietic cells in vivo.* Blood 99(11):3939-3946 (2002).
Sasaki, M. et al. *The overexpression of polycomb group proteins Bmi 1 and EZH2 is associated with the progression and aggressive biological behavior of hepatocellular carcinoma.* Lab. Invest. 88(8):873-882 (2008).
Sasaki, M., et al., *Over-expression of polycomb group protein EZH2 relates to decreased expression of p16 INK4a in cholangiocarcinogenesis in hepatolithiasis.* J Pathol 215(2):175-183 (2008).
Schafmeister et al., *An All-Hydrocarbon Cross-Linking System for Enhancing the Helicity and Metabolic Stability of Peptides*, J. Am. Chem. Soc., 122:5891-5892 (2000).
Shen, X. et al. *EZH1 Mediates Methylation on Histone H3 Lysine 27 and Complements EZH2 in Maintaining Stem Cell Identity and Executing Pluripotency.* Molecular Cell 32(4):491-502 (2008).
Shen, X. et al. *Jumonji Modulates Polycomb Activity and Self-Renewal versus Differentiation of Stem Cells.* Cell 139(7):1303-1314 (2009).
Shi, J. et al. *The Polycomb complex PRC2 supports aberrant self-renewal in a mouse model of MLL-AF9; Nras(G12D) acute myeloid leukemia.* Oncogene 32(7):930-938 (2012).
Simon, J. A. et al., *Mechanisms of polycomb gene silencing: knowns and unknowns.* Nat Rev Mol Cell Biol 10(10):697-708 (2009).
Singh, S. K. et al. *Identification of human brain tumour initiating cells.* Nature 432(7015):396-401 (2004).
Sneeringer, C. J. et al. *Coordinated activities of wild-type plus mutant EZH2 drive tumor-associated hypertrimethylation of lysine*

(56) References Cited

OTHER PUBLICATIONS 27 on histone H3 (H3K27) in human B-cell lymphomas. Proceedings of the National Academy of Sciences 107(49):20980-20985 (2010).

Stewart, M. L., et al., *The MCL-1 BH3 helix is an exclusive MCL-1 inhibitor and apoptosis sensitizer.* Nature Chemical Biology 6, 595-601 (2010).

Suetsugu, A. et al. *Characterization of CD133+ hepatocellular carcinoma cells as cancer stem/progenitor cells.* Biochemical and Biophysical Research Communications 351(4): 820-824.

Szu et al., *Comparative immunogenicities of Vi polysaccharide-protein conjugates composed of cholera toxin or its B subunit as a carrier bound to high- or lower-molecular-weight Vi.* Infect. Immun. 57(12):3823-3827 (1989).

Szu et al., *Relation between structure and immunologic properties of the Vi capsular polysaccharide,* Infect. Immun 59(12):4555-4561,1991.

Szu et al., *Laboratory and preliminary clinical characterization of Vi capsular polysaccharide-protein conjugate vaccines,* Infect. Immun 62(10):4440-4444, 1994.

Szu et al., *Vi capsular polysaccharide-protein conjugates for prevention of typhoid fever. Preparation, characterization, and immunogenicity in laboratory animals,* J. Exp. Med. 166(5):1510-1524, 1987.

Takada, K. et al. *Targeted Disruption of the BCL9/β-Catenin Complex Inhibits Oncogenic Wnt Signaling.* Sci Transl Med 4(148):148ra117 (2012).

Tan, J. et al. *Pharmacologic disruption of Polycomb-repressive complex 2-mediated gene repression selectively induces apoptosis in cancer cells.* Genes & Development 21(9):1050-1063 (2007).

Toren, A. et al. *CD133-positive hematopoietic stem cell 'stemness' genes contain many genes mutated or abnormally expressed in leukemia.* Stem Cells 23(8):1142-1153 (2005).

Varambally, S. et al. *Genomic Loss of microRNA-101 Leads to Overexpression of Histone Methyltransferase EZH2 in Cancer.* Science 322(5908):1695-1699 (2008).

Varambally, S. et al. *The polycomb group protein EZH2 is involved in progression of prostate cancer.* Nature 419(6907):624-629 (2002).

Wagener, N. et al. *Enhancer of zeste homolog 2 (EZH2) expression is an independent prognostic factor in renal cell carcinoma.* BMC Cancer 10:524 (2010).

Walensky, L. D. *Activation of Apoptosis in Vivo by a Hydrocarbon-Stapled BH3 Helix.* Science 305, 1466-1470 (2004).

Walensky, L. D. et al. *A Stapled BID BH3 Helix Directly Binds and Activates BAX.* Molecular Cell 24, 199-210 (2006).

Wang, C. et al. *EZH2 Mediates epigenetic silencing of neuroblastoma suppressor genes CASZ1, CLU, RUNX3, and NGFR.* Cancer Research 72, 315-324 (2012).

Wilen, S. H., et al., *Strategies in Optical Resolutions,* Tetrahedron 33:2725 (1977).

Wilen, S.H. *Tables of Resolving Agents and Optical Resolutions* p. 268 (EX. Eliel, Ed., Univ. of Notre Dame Press, Notre Dame, IN (1972).

Williams et al. *Asymmetric Synthesis of Monosubstituted and a,a-Disubstituted a-Amino Acids via Diastereoselective Glycine Enolate Alkylations,* J. Am. Chem. Soc., 113:9276, (1991).

Williams et al., *Efficient Asymmetric Synthesis of N-tert-Butoxycarbonyl ☐-Amino Acids Using 4-tert-Butoxycarbonyl-5,6-Diphenylmorpholin-2-One: (R)-(Ntert-Butoxycarbonyl)Allylglycine [(4-Pentenoic acid, 2-[[(1,1-dimethylethoxy)carbony]amino]-, (2R)-)],* Org. Synth., 80:31-37 (2003).

Wilson, B. G. et al. *Epigenetic Antagonism between Polycomb and SWI/SNF Complexes during Oncogenic Transformation.* Cancer Cell 18(4):316-328 (2010).

Yang et al., *[11] Calculation of Protein Conformation from Circular Dichroism,* Methods Enzymol. 130:208-269 (1986).

Yap, D. B. et al. *Somatic mutations at EZH2 Y641 act dominantly through a mechanism of selectively altered PRC2 catalytic activity, to increase H3K27 trimethylation.* Blood 117(8):2451-2459 (2011).

You, J. S. et al., *Cancer genetics and epigenetics: two sides of the same coin?* Cancer Cell 22(1):9-20 (2012).

Yu, J. et al. *Integrative Genomics Analysis Reveals Silencing of β-Adrenergic Signaling by Polycomb in Prostate Cancer.* Cancer Cell 12(5):419-431 (2007).

Raaphorst, FM et al., EZH2 Protein, Partial [*Homo sapiens*]: GenBank Accession No. AAS09975.1, Feb. 7, 2004. Pathology, VU Medical Center, Amsterdam, Netherlands. 1 page.

International Search Report for PCT/US2014/025587, dated Sep. 26, 2014. 5 pages.

EPO Extended Search Report for EP App No. 14767620.9, dated Jul. 20, 2016 (9 pages).

Kim et al., *Targeted disruption of the EZH2-EED complex inhibits EZH2-dependent cancer,* Nat. Chem. Biol., 9(10):643-650 (Oct. 2013).

Australia Patent Office Examination Report for App. No. AU 2014235039, dated Oct. 10, 2017 (4 pages).

Baek et al., *Structure of the stapled p53 peptide bound to Mdm2,* J. Am. Chem.Soc., 134(1): 103-106, Jan. 2012.

Bird et al., *Mucosal delivery of a double-stapled RSV peptide prevents nasopulmonary infection,* J. Clin. Invest., 124(5): 2113-2124, May 2014.

Bird et al., *Biophysical determinants for cellular uptake of hydrocarbon-stapled peptide helices,* Nat. Chem. Biol., 12(10): 845-852, Oct. 2016.

Chang et al., *Stapled α-helical peptide drug development: a potent dual inhibitor of MDM2 and MDMX for p53-dependent cancer therapy,* PNAS 110(36): E3445-E3454, Sep. 2013.

Chapuis et al., *Effect of hydrocarbon stapling on the properties of α-helical antimicrobial peptides isolated from the venom of hymenoptera,* Amino Acids, 43(5): 2047-2058, Nov. 2012.

Stewart et al., *The MCL-1 BH3 Helix is an exclusive MCL-1 inhibitor and apoptosis sensitizer,* Nat Chem Biol., 6(8): 595-601, Aug. 2010.

\* cited by examiner

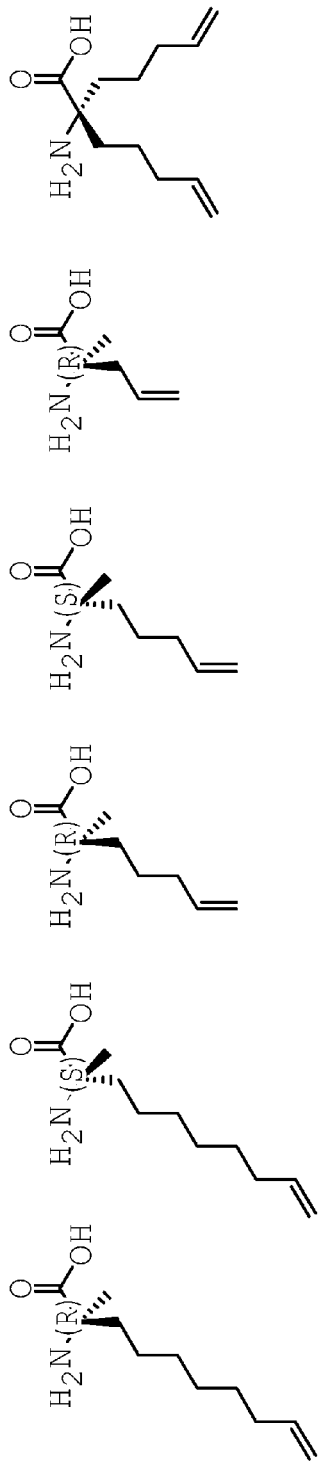
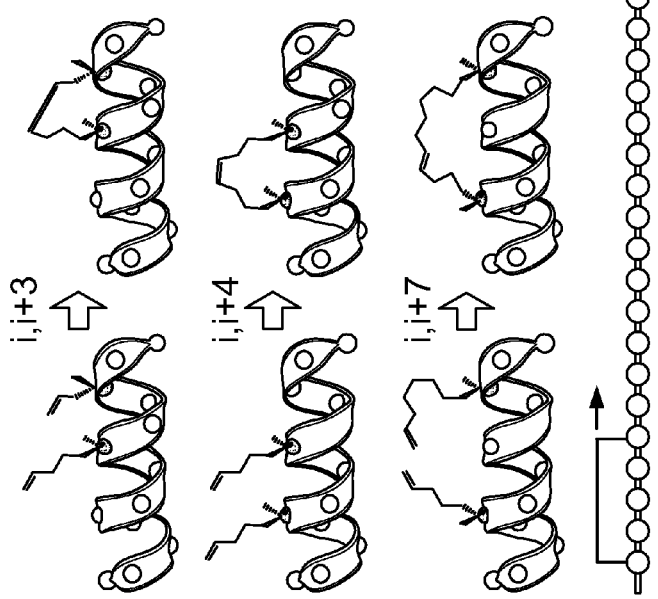
FIG. 1A
FIG. 1B a

SAH-EZH2_A(40-68)  SN_LFSSNRXKILXRTEILNQEWKQRRIQPV
SAH-EZH2_A(42-68)      FSSNRXKILXRTEILNQEWKQRRIQPV
SAH-EZH2_A(42-64)      FSSNRXKILXRTEILNQEWKQRR

SAH-EZH2_B(40-68)  SN_LFSSNRQKILERTXILNXEWKQRRIQPV
SAH-EZH2_B(42-68)      FSSNRQKILERTXILNXEWKQRRIQPV
SAH-EZH2_B(42-64)      FSSNRQKILERTXILNXEWKQRR

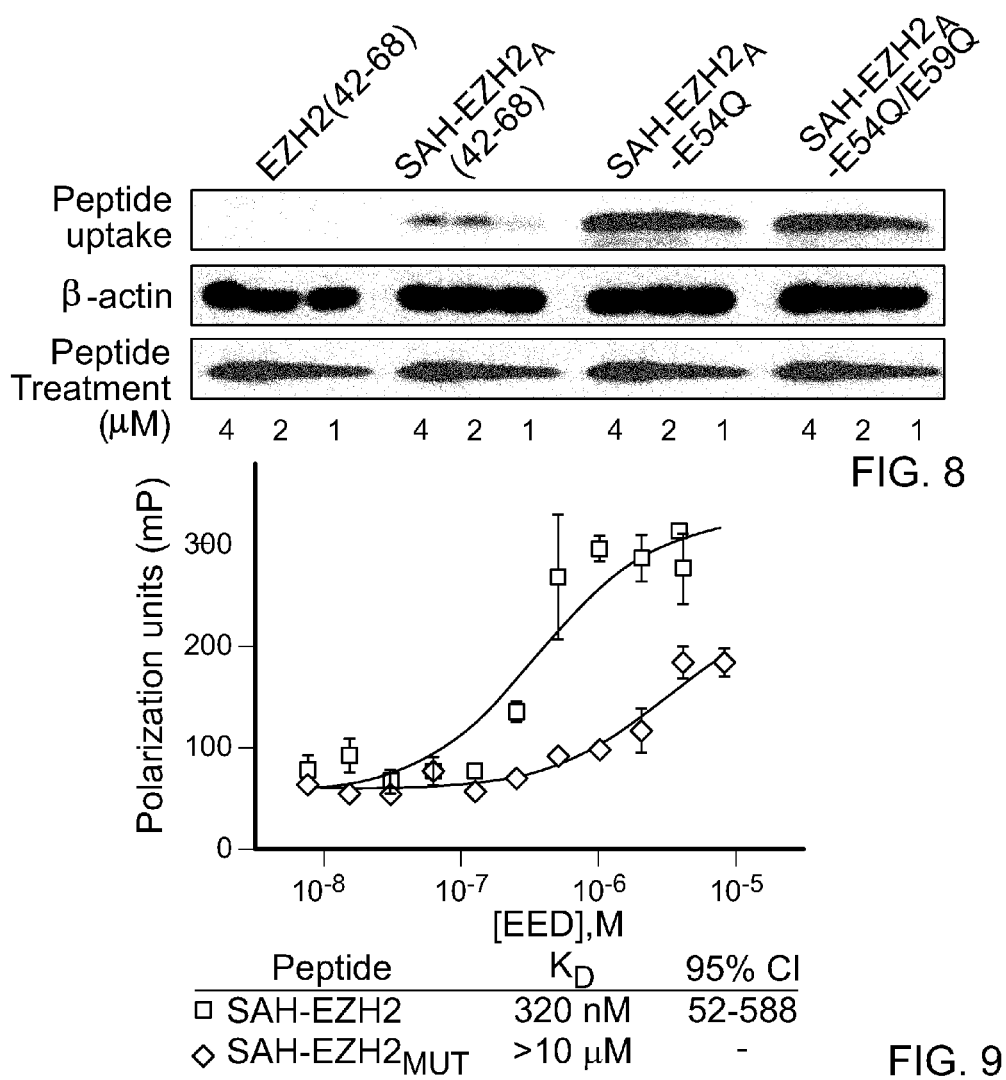
FIG. 8
FIG. 9
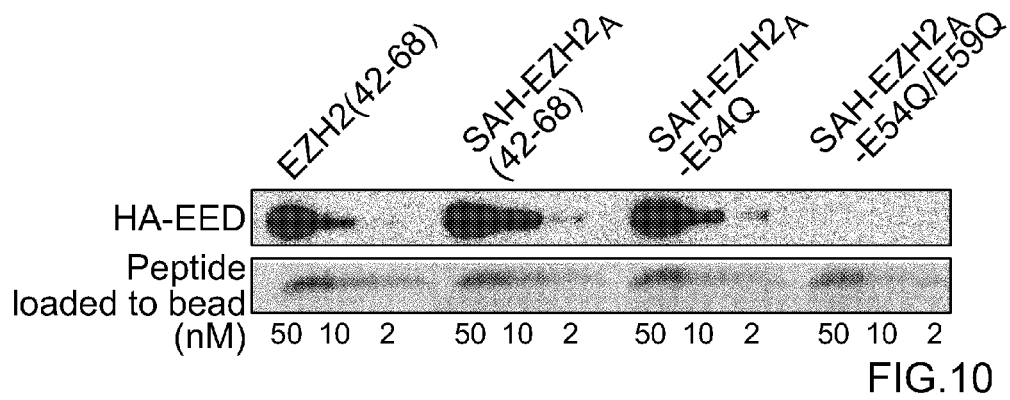
FIG. 10

1. Flow through
2. 1st Wash
3. 2nd Wash
4. 1st Elute
5. 2nd Elute

6. Proteins left bound to resin after elution

| Competitor | K_D | 95% CI | |
|---|---|---|---|
| ◇ EZH2(47-64) | - | - | QKILERTQILNQEWKQRR |
| ○ SAH-EZH2 | 1.13 μM | 0.51 μM - 2.52 μM | FSSNRXKILXRTQILNQEWKQRRIQPV |
| △ EZH2(42-68)AC | 0.65 μM | 0.34 μM - 1.25 μM | FSSNRXKILXRTXILNXEWKQRRIQPV |

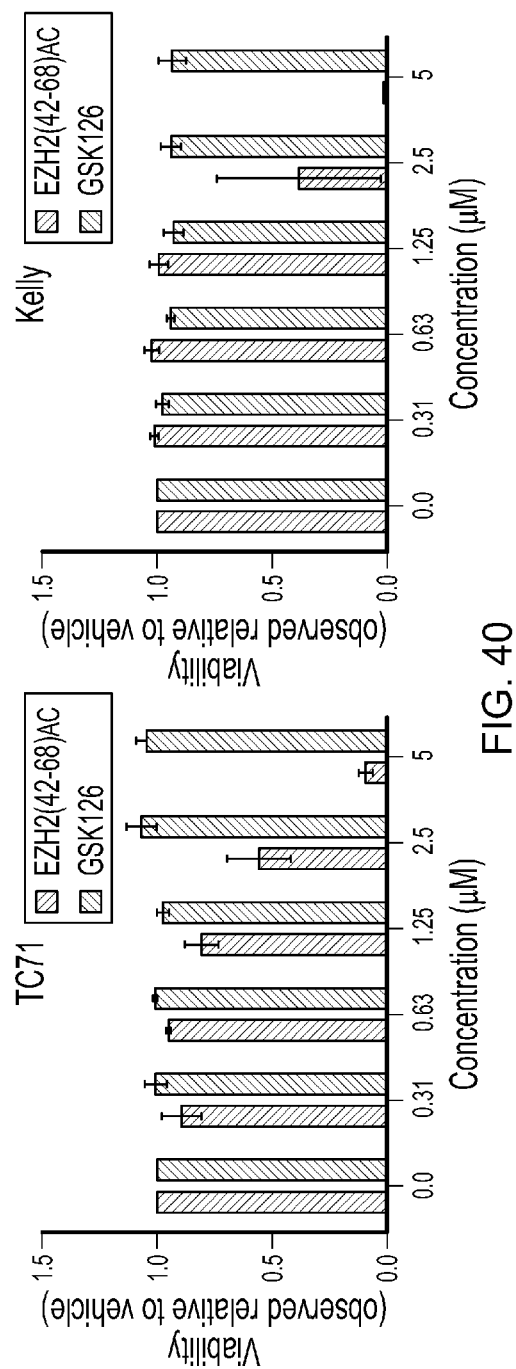
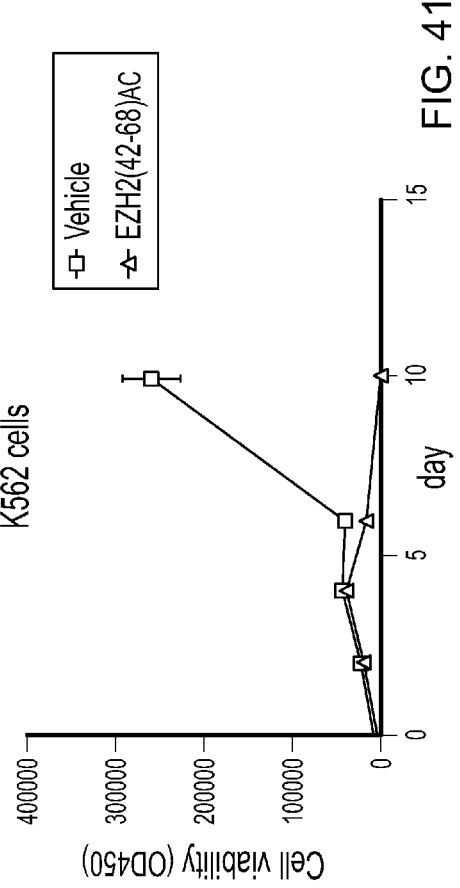
FIG. 40
FIG. 41

SEQUENCE LISTING

```
<160> NUMBER OF SEQ ID NOS: 56

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or any conservative amino acid substitution
<220> FEATURE:
<221> NAME/KEY: MOD_RES
<222> LOCATION: (2)..(2)
<223> OTHER INFORMATION: Met or any conservative amino acid substitution
<220> FEATURE:
<221> NAME/KEY: MOD_RES
<222> LOCATION: (3)..(3)
<223> OTHER INFORMATION: Phe or any conservative amino acid substitution
<220> FEATURE:
<221> NAME/KEY: MOD_RES
<222> LOCATION: (4)..(5)
<223> OTHER INFORMATION: Ser or any conservative amino acid substitution
<220> FEATURE:
<221> NAME/KEY: MOD_RES
<222> LOCATION: (6)..(6)
<223> OTHER INFORMATION: Asn or any conservative amino acid substitution
<220> FEATURE:
<221> NAME/KEY: MOD_RES
<222> LOCATION: (7)..(7)
```

```
<223> OTHER INFORMATION: Arg or any conservative amino acid substitution
<220> FEATURE:
<221> NAME/KEY: MOD_RES
<222> LOCATION: (8)..(8)
<223> OTHER INFORMATION: Gln, any conservative amino acid substitution
      or any stapled amino acid substitution to position 12
<220> FEATURE:
<221> NAME/KEY: MOD_RES
<222> LOCATION: (9)..(9)
<223> OTHER INFORMATION: Lys or any conservative amino acid substitution
<220> FEATURE:
<221> NAME/KEY: MOD_RES
<222> LOCATION: (10)..(10)
<223> OTHER INFORMATION: Ile or any conservative amino acid substitution
<220> FEATURE:
<221> NAME/KEY: MOD_RES
<222> LOCATION: (11)..(11)
<223> OTHER INFORMATION: Leu or any conservative amino acid substitution
<220> FEATURE:
<221> NAME/KEY: MOD_RES
<222> LOCATION: (12)..(12)
<223> OTHER INFORMATION: Glu, Gln, any conservative amino acid
      substitution or any stapled amino acid substitution to position 8
<220> FEATURE:
<221> NAME/KEY: MOD_RES
<222> LOCATION: (13)..(13)
<223> OTHER INFORMATION: Arg or any conservative amino acid substitution
<220> FEATURE:
<221> NAME/KEY: MOD_RES
<222> LOCATION: (14)..(14)
<223> OTHER INFORMATION: Thr or any conservative amino acid substitution
<220> FEATURE:
<221> NAME/KEY: MOD_RES
<222> LOCATION: (15)..(15)
<223> OTHER INFORMATION: Glu, Gln or any conservative amino acid
      substitution
<220> FEATURE:
<221> NAME/KEY: MOD_RES
<222> LOCATION: (16)..(16)
<223> OTHER INFORMATION: Ile or any conservative amino acid substitution
<220> FEATURE:
<221> NAME/KEY: MOD_RES
<222> LOCATION: (17)..(17)
<223> OTHER INFORMATION: Leu or any conservative amino acid substitution
<220> FEATURE:
<221> NAME/KEY: MOD_RES
<222> LOCATION: (18)..(18)
<223> OTHER INFORMATION: Asn or any conservative amino acid substitution
<220> FEATURE:
<221> NAME/KEY: MOD_RES
<222> LOCATION: (19)..(19)
<223> OTHER INFORMATION: Gln or any conservative amino acid substitution
<220> FEATURE:
<221> NAME/KEY: MOD_RES
<222> LOCATION: (20)..(20)
<223> OTHER INFORMATION: Glu, Gln or any conservative amino acid
      substitution
<220> FEATURE:
<221> NAME/KEY: MOD_RES
<222> LOCATION: (21)..(21)
<223> OTHER INFORMATION: Trp or any conservative amino acid substitution
<220> FEATURE:
<221> NAME/KEY: MOD_RES
<222> LOCATION: (22)..(22)
<223> OTHER INFORMATION: Lys or any conservative amino acid substitution
<220> FEATURE:
<221> NAME/KEY: MOD_RES
<222> LOCATION: (23)..(23)
<223> OTHER INFORMATION: Gln or any conservative amino acid substitution
<220> FEATURE:
<221> NAME/KEY: MOD_RES
<222> LOCATION: (24)..(25)
<223> OTHER INFORMATION: Arg or any conservative amino acid substitution
<220> FEATURE:
<221> NAME/KEY: MOD_RES
<222> LOCATION: (26)..(26)
<223> OTHER INFORMATION: Ile or any conservative amino acid substitution
<220> FEATURE:
<221> NAME/KEY: MOD_RES
```

```
<222> LOCATION: (27)..(27)
<223> OTHER INFORMATION: Gln or any conservative amino acid substitution
<220> FEATURE:
<221> NAME/KEY: MOD_RES
<222> LOCATION: (28)..(28)
<223> OTHER INFORMATION: Pro or any conservative amino acid substitution
<220> FEATURE:
<221> NAME/KEY: MOD_RES
<222> LOCATION: (29)..(29)
<223> OTHER INFORMATION: Val or any conservative amino acid substitution
<220> FEATURE:
<223> OTHER INFORMATION: See specification as filed for detailed
      description of substitutions and preferred embodiments

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Met Phe Ser Ser Asn Arg Gln Lys Ile Leu Glu Arg Thr Glu Ile
1               5                   10                  15

Leu Asn Gln Glu Trp Lys Gln Arg Arg Ile Gln Pro Val
            20                  25

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 3

Ser Leu Phe Ser Ser Asn Arg Xaa Lys Ile Leu Xaa Arg Thr Glu Ile
1               5                   10                  15

Leu Asn Gln Glu Trp Lys Gln Arg Arg Ile Gln Pro Val
            20                  25

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

```
<223> OTHER INFORMATION: Norleucine
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (16)..(16)
<223> OTHER INFORMATION: Any stapling amino acid

<400> SEQUENCE: 4

Ser Leu Phe Ser Ser Asn Arg Gln Lys Ile Leu Xaa Arg Thr Glu Xaa
1               5                   10                  15

Leu Asn Gln Glu Trp Lys Gln Arg Arg Ile Gln Pro Val
            20                  25

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (15)..(15)
<223> OTHER INFORMATION: Any stapling amino acid
<220> FEATURE:
<221> NAME/KEY: MOD_RES
<222> LOCATION: (19)..(19)
<223> OTHER INFORMATION: Any stapling amino acid

<400> SEQUENCE: 5

Ser Leu Phe Ser Ser Asn Arg Gln Lys Ile Leu Glu Arg Thr Xaa Ile
1               5                   10                  15

Leu Asn Xaa Glu Trp Lys Gln Arg Arg Ile Gln Pro Val
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (16)..(16)
<223> OTHER INFORMATION: Any stapling amino acid
<220> FEATURE:
<221> NAME/KEY: MOD_RES
<222> LOCATION: (20)..(20)
<223> OTHER INFORMATION: Any stapling amino acid

<400> SEQUENCE: 6

Ser Leu Phe Ser Ser Asn Arg Gln Lys Ile Leu Glu Arg Thr Glu Xaa
1               5                   10                  15

Leu Asn Gln Xaa Trp Lys Gln Arg Arg Ile Gln Pro Val
            20                  25

<210> SEQ ID NO 7
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (19)..(19)
<223> OTHER INFORMATION: Any stapling amino acid
<220> FEATURE:
<221> NAME/KEY: MOD_RES
<222> LOCATION: (23)..(23)
<223> OTHER INFORMATION: Any stapling amino acid

<400> SEQUENCE: 7

Ser Leu Phe Ser Ser Asn Arg Gln Lys Ile Leu Glu Arg Thr Glu Ile
1               5                   10                  15

Leu Asn Xaa Glu Trp Lys Xaa Arg Arg Ile Gln Pro Val
            20                  25

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (21)..(21)
<223> OTHER INFORMATION: Norleucine

<400> SEQUENCE: 8

Ser Leu Phe Ser Ser Asn Arg Gln Lys Ile Leu Glu Arg Thr Glu Ile
1               5                   10                  15

Leu Asn Gln Glu Leu Trp Gln Arg Arg Ile Gln
            20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (15)..(15)
<223> OTHER INFORMATION: Any stapling amino acid
<220> FEATURE:
<221> NAME/KEY: MOD_RES
<222> LOCATION: (19)..(19)
<223> OTHER INFORMATION: Any stapling amino acid
<220> FEATURE:
<221> NAME/KEY: MOD_RES
<222> LOCATION: (21)..(21)
<223> OTHER INFORMATION: Norleucine

<400> SEQUENCE: 9

Ser Leu Phe Ser Ser Asn Arg Gln Lys Ile Leu Glu Arg Thr Xaa Ile
```

```
                1               5                   10                  15
Leu Asn Xaa Glu Leu Trp Gln Arg Arg Ile Gln
            20                  25

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (19)..(19)
<223> OTHER INFORMATION: Any stapling amino acid
<220> FEATURE:
<221> NAME/KEY: MOD_RES
<222> LOCATION: (21)..(21)
<223> OTHER INFORMATION: Norleucine
<220> FEATURE:
<221> NAME/KEY: MOD_RES
<222> LOCATION: (23)..(23)
<223> OTHER INFORMATION: Any stapling amino acid

<400> SEQUENCE: 10

Ser Leu Phe Ser Ser Asn Arg Gln Lys Ile Leu Glu Arg Thr Glu Ile
1               5                   10                  15

Leu Asn Xaa Glu Leu Trp Xaa Arg Arg Ile Gln
            20                  25

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Lys Ile Leu Glu Arg Thr Glu Ile Leu Asn Gln Glu Trp Lys Gln
1               5                   10                  15

Arg Arg

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Norleucine

<400> SEQUENCE: 12

Gln Lys Ile Leu Glu Arg Thr Glu Ile Leu Asn Gln Glu Leu Trp Gln
1               5                   10                  15

Arg Arg

<210> SEQ ID NO 13
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (14)..(14)
<223> OTHER INFORMATION: Norleucine

<400> SEQUENCE: 13

Gln Lys Ile Leu Glu Arg Thr Xaa Ile Leu Asn Xaa Glu Leu Trp Gln
1               5                   10                  15

Arg Arg

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (16)..(16)
<223> OTHER INFORMATION: Any stapling amino acid

<400> SEQUENCE: 14

Gln Lys Ile Leu Glu Arg Thr Glu Ile Leu Asn Xaa Glu Leu Trp Xaa
1               5                   10                  15

Arg Arg

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any stapling amino acid
<220> FEATURE:
<221> NAME/KEY: MOD_RES
<222> LOCATION: (7)..(7)
<223> OTHER INFORMATION: Any stapling amino acid

<400> SEQUENCE: 15

Asn Arg Xaa Lys Ile Leu Xaa Arg Thr Glu Ile Leu Asn Gln Glu Trp
1               5                   10                  15

Lys Gln Arg Arg
            20

<210> SEQ ID NO 16
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any stapling amino acid
<220> FEATURE:
<221> NAME/KEY: MOD_RES
<222> LOCATION: (14)..(14)
<223> OTHER INFORMATION: Any stapling amino acid

<400> SEQUENCE: 16

Asn Arg Gln Lys Ile Leu Glu Arg Thr Xaa Ile Leu Asn Xaa Glu Trp
1               5                   10                  15

Lys Gln Arg Arg
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any stapling amino acid
<220> FEATURE:
<221> NAME/KEY: MOD_RES
<222> LOCATION: (7)..(7)
<223> OTHER INFORMATION: Any stapling amino acid

<400> SEQUENCE: 17

Asn Arg Xaa Lys Ala Leu Xaa Arg Thr Glu Ile Ala Asn Gln Glu Ala
1               5                   10                  15

Lys Gln Arg Arg
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any stapling amino acid
<220> FEATURE:
<221> NAME/KEY: MOD_RES
<222> LOCATION: (14)..(14)
<223> OTHER INFORMATION: Any stapling amino acid

<400> SEQUENCE: 18

Asn Arg Gln Lys Ala Leu Glu Arg Thr Xaa Ile Ala Asn Xaa Glu Ala
1               5                   10                  15

Lys Gln Arg Arg
            20

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 19

Phe Ser Ser Asn Arg Xaa Lys Ile Leu Xaa Arg Thr Glu Ile Leu Asn
1               5                   10                  15

Gln Glu Trp Lys Gln Arg Arg
            20

<210> SEQ ID NO 20
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any stapling amino acid
<220> FEATURE:
<221> NAME/KEY: MOD_RES
<222> LOCATION: (17)..(17)
<223> OTHER INFORMATION: Any stapling amino acid

<400> SEQUENCE: 20

Phe Ser Ser Asn Arg Gln Lys Ile Leu Glu Arg Thr Xaa Ile Leu Asn
1               5                   10                  15

Xaa Glu Trp Lys Gln Arg Arg
            20

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 21

Phe Xaa Ser Asn Arg Xaa Lys Ile Leu Xaa Arg Thr Gln Ile Leu Asn
1               5                   10                  15

Gln Glu Trp Lys Gln Arg Arg
            20

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic

```
                                              peptide
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 22

Phe Ser Xaa Asn Arg Xaa Lys Ile Leu Xaa Arg Thr Gln Ile Leu Asn
 1               5                  10                  15

Gln Glu Trp Lys Gln Arg Arg
            20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
                        peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (13)..(13)
<223> OTHER INFORMATION: Any stapling amino acid
<220> FEATURE:
<221> NAME/KEY: MOD_RES
<222> LOCATION: (17)..(17)
<223> OTHER INFORMATION: Any stapling amino acid

<400> SEQUENCE: 23

Phe Xaa Ser Asn Arg Gln Lys Ile Leu Gln Arg Thr Xaa Ile Leu Asn
 1               5                  10                  15

Xaa Glu Trp Lys Gln Arg Arg
            20

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
                        peptide
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (13)..(13)
<223> OTHER INFORMATION: Any stapling amino acid
<220> FEATURE:
<221> NAME/KEY: MOD_RES
<222> LOCATION: (17)..(17)
<223> OTHER INFORMATION: Any stapling amino acid

<400> SEQUENCE: 24

Phe Ser Xaa Asn Arg Gln Lys Ile Leu Gln Arg Thr Xaa Ile Leu Asn
 1               5                  10                  15

Xaa Glu Trp Lys Gln Arg Arg
            20
```

```
<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (13)..(13)
<223> OTHER INFORMATION: Any stapling amino acid
<220> FEATURE:
<221> NAME/KEY: MOD_RES
<222> LOCATION: (17)..(17)
<223> OTHER INFORMATION: Any stapling amino acid

<400> SEQUENCE: 25

Phe Xaa Ser Asn Arg Gln Lys Ala Leu Gln Arg Thr Xaa Ile Ala Asn
1               5                   10                  15

Xaa Glu Ala Lys Gln Arg Arg
            20

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 26

Phe Ser Ser Asn Arg Xaa Lys Ile Leu Xaa Arg Thr Glu Ile Leu Asn
1               5                   10                  15

Gln Glu Trp Lys Gln Arg Arg Ile Gln Pro Val
            20                  25

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 27

Phe Ser Ser Asn Arg Xaa Lys Ile Leu Xaa Arg Thr Gln Ile Leu Asn
1               5                   10                  15

Gln Glu Trp Lys Gln Arg Arg Ile Gln Pro Val
            20                  25
```

```
<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 28

Phe Ser Ser Asn Arg Xaa Lys Ile Leu Xaa Arg Thr Gln Ile Leu Asn
1               5                   10                  15

Gln Gln Trp Lys Gln Arg Arg Ile Gln Pro Val
            20                  25

<210> SEQ ID NO 29
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 29

Phe Ser Ser Asn Arg Xaa Gln Ile Leu Xaa Arg Thr Gln Ile Leu Asn
1               5                   10                  15

Gln Lys Trp Lys Gln Arg Arg Ile Gln Pro Val
            20                  25

<210> SEQ ID NO 30
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any stapling amino acid
<220> FEATURE:
<221> NAME/KEY: MOD_RES
<222> LOCATION: (14)..(14)
<223> OTHER INFORMATION: Any stapling amino acid

<400> SEQUENCE: 30

Phe Ser Ser Asn Arg Gln Lys Ile Leu Xaa Arg Thr Glu Xaa Leu Asn
1               5                   10                  15

Gln Glu Trp Lys Gln Arg Arg Ile Gln Pro Val
            20                  25

<210> SEQ ID NO 31
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any stapling amino acid
<220> FEATURE:
<221> NAME/KEY: MOD_RES
<222> LOCATION: (14)..(14)
<223> OTHER INFORMATION: Any stapling amino acid

<400> SEQUENCE: 31

Phe Ser Ser Asn Arg Gln Lys Ile Leu Xaa Arg Thr Gln Xaa Leu Asn
1               5                   10                  15

Gln Glu Trp Lys Gln Arg Arg Ile Gln Pro Val
            20                  25

<210> SEQ ID NO 32
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any stapling amino acid
<220> FEATURE:
<221> NAME/KEY: MOD_RES
<222> LOCATION: (14)..(14)
<223> OTHER INFORMATION: Any stapling amino acid

<400> SEQUENCE: 32

Phe Ser Ser Asn Arg Gln Lys Ile Leu Xaa Arg Thr Gln Xaa Leu Asn
1               5                   10                  15

Gln Gln Trp Lys Gln Arg Arg Ile Gln Pro Val
            20                  25

<210> SEQ ID NO 33
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any stapling amino acid
<220> FEATURE:
<221> NAME/KEY: MOD_RES
<222> LOCATION: (17)..(17)
<223> OTHER INFORMATION: Any stapling amino acid

<400> SEQUENCE: 33

Phe Ser Ser Asn Arg Gln Lys Ile Leu Glu Arg Thr Xaa Ile Leu Asn
1               5                   10                  15

Xaa Glu Trp Lys Gln Arg Arg Ile Gln Pro Val
            20                  25

<210> SEQ ID NO 34
<211> LENGTH: 27
<212> TYPE: PRT
<213> ORGANISM: Artificial Sequence
<220> FEATURE:
<223> OTHER INFORMATION: Description of Artificial Sequence: Synthetic
```

```
    peptide
<220> FEATURE:
<221> NAME/KEY: MOD_RES
<222> LOCATION: (13)..(13)
<223> OTHER INFORMATION: Any stapling amino acid
<220> FEATURE:
<221> NAME/KEY: MOD_RES
<222> LOCATION: (17)..(17)
<223> OTHER INFORMATION: Any stapling amino acid

<400> SEQUENCE: 34

Phe Ser Ser Asn Arg Gln Lys Ile Leu Gln Arg Thr Xaa Ile Leu Asn
1               5                  10                  15

Xaa Glu Trp Lys Gln Arg Arg Ile Gln Pro Val
            20                  25

<210> SEQ ID NO 35
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any stapling amino acid
<220> FEATURE:
<221> NAME/KEY: MOD_RES
<222> LOCATION: (17)..(17)
<223> OTHER INFORMATION: Any stapling amino acid

<400> SEQUENCE: 35

Phe Ser Ser Asn Arg Gln Lys Ile Leu Gln Arg Thr Xaa Ile Leu Asn
1               5                  10                  15

Xaa Gln Trp Lys Gln Arg Arg Ile Gln Pro Val
            20                  25

<210> SEQ ID NO 36
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any stapling amino acid
<220> FEATURE:
<221> NAME/KEY: MOD_RES
<222> LOCATION: (18)..(18)
<223> OTHER INFORMATION: Any stapling amino acid

<400> SEQUENCE: 36

Phe Ser Ser Asn Arg Gln Lys Ile Leu Glu Arg Thr Glu Xaa Leu Asn
1               5                  10                  15

Gln Xaa Trp Lys Gln Arg Arg Ile Gln Pro Val
            20                  25

<210> SEQ ID NO 37
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
```

<223> OTHER INFORMATION: Any stapling amino acid
<220> FEATURE:
<221> NAME/KEY: MOD_RES
<222> LOCATION: (18)..(18)
<223> OTHER INFORMATION: Any stapling amino acid

<400> SEQUENCE: 37

Phe Ser Ser Asn Arg Gln Lys Ile Leu Gln Arg Thr Glu Xaa Leu Asn
1               5                   10                  15

Gln Xaa Trp Lys Gln Arg Arg Ile Gln Pro Val
            20                  25

<210> SEQ ID NO 38
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any stapling amino acid
<220> FEATURE:
<221> NAME/KEY: MOD_RES
<222> LOCATION: (18)..(18)
<223> OTHER INFORMATION: Any stapling amino acid

<400> SEQUENCE: 38

Phe Ser Ser Asn Arg Gln Lys Ile Leu Glu Arg Thr Gln Xaa Leu Asn
1               5                   10                  15

Gln Xaa Trp Lys Gln Arg Arg Ile Gln Pro Val
            20                  25

<210> SEQ ID NO 39
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any stapling amino acid
<220> FEATURE:
<221> NAME/KEY: MOD_RES
<222> LOCATION: (18)..(18)
<223> OTHER INFORMATION: Any stapling amino acid

<400> SEQUENCE: 39

Phe Ser Ser Asn Arg Gln Lys Ile Leu Gln Arg Thr Gln Xaa Leu Asn
1               5                   10                  15

Gln Xaa Trp Lys Gln Arg Arg Ile Gln Pro Val
            20                  25

<210> SEQ ID NO 40
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Ser Ser Asn Arg Gln Lys Ile Leu Glu Arg Thr Glu Ile Leu Asn
1               5                   10                  15

Gln Glu Trp Lys Gln Arg Arg Ile Gln Pro Val 20                  25

<210> SEQ ID NO 41
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Ser Ser Asn Arg Gln Lys Ile Leu Glu Arg Thr Gln Ile Leu Asn
1               5                   10                  15

Gln Glu Trp Lys Gln Arg Arg Ile Gln Pro Val
            20                  25

<210> SEQ ID NO 42
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Arg Arg Ser Met Phe Ser Ser Asn Arg Gln Lys Ile Leu Glu Arg Thr
1               5                   10                  15

Glu Ile Leu Asn Gln Glu Trp Lys Gln Arg Arg Ile Gln Pro Val
            20                  25                  30

<210> SEQ ID NO 43
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Arg Phe Ser Ser Asn Arg Gln Lys Ile Leu Glu Arg Thr Glu Ile
1               5                   10                  15

Leu Asn Gln Glu Trp Lys Gln Arg Arg Ile Gln Pro Val
            20                  25

<210> SEQ ID NO 44
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Arg Phe Ser Ser Asn Arg Gln Lys Ile Leu Glu Arg Thr Gln Ile
1               5                   10                  15

Leu Asn Gln Glu Trp Lys Gln Arg Arg Ile Gln Pro Val
            20                  25

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 45

Arg Ser Met Phe Ser Ser Asn Arg Gln Lys Ile Leu Glu Arg Thr Glu
1               5                   10                  15

Ile Leu Asn Gln Glu Trp Lys Gln Arg Arg Ile Gln Pro Val
            20                  25                  30

<210> SEQ ID NO 46
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Phe Ser Ser Asn Arg Gln Lys Ile Leu Glu Arg Thr Glu Ile Leu
1               5                   10                  15

Asn Gln Glu Trp Lys Gln Arg Arg Ile Gln Pro Val
            20                  25

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Phe Ser Ser Asn Arg Gln Lys Ile Leu Glu Arg Thr Gln Ile Leu
1               5                   10                  15

Asn Gln Glu Trp Lys Gln Arg Arg Ile Gln Pro Val
            20                  25

<210> SEQ ID NO 48
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser Met Phe Ser Ser Asn Arg Gln Lys Ile Leu Glu Arg Thr Glu Ile
1               5                   10                  15

Leu Asn Gln Glu Trp Lys Gln Arg Arg Ile Gln Pro Val Arg Arg
            20                  25                  30

<210> SEQ ID NO 49
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Ser Ser Asn Arg Gln Lys Ile Leu Glu Arg Thr Glu Ile Leu Asn
1               5                   10                  15

Gln Glu Trp Lys Gln Arg Arg Ile Gln Pro Val Arg Arg
            20                  25

<210> SEQ ID NO 50
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Phe Ser Ser Asn Arg Gln Lys Ile Leu Glu Arg Thr Gln Ile Leu Asn
1               5                   10                  15

Gln Glu Trp Lys Gln Arg Arg Ile Gln Pro Val Arg Arg
            20                  25

<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ser Met Phe Ser Ser Asn Arg Gln Lys Ile Leu Glu Arg Thr Glu Ile
1               5                   10                  15

Leu Asn Gln Glu Trp Lys Gln Arg Arg Ile Gln Pro Val Arg
            20                  25                  30

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Ser Ser Asn Arg Gln Lys Ile Leu Glu Arg Thr Glu Ile Leu Asn
1               5                   10                  15

Gln Glu Trp Lys Gln Arg Arg Ile Gln Pro Val Arg
            20                  25

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Phe Ser Ser Asn Arg Gln Lys Ile Leu Glu Arg Thr Gln Ile Leu Asn
1               5                   10                  15

Gln Glu Trp Lys Gln Arg Arg Ile Gln Pro Val Arg
            20                  25

<210> SEQ ID NO 54
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Arg Lys Lys Arg Arg Gln Arg Arg Arg Pro Gln Phe Ser Ser Asn
1               5                   10                  15
```

```
Arg Gln Lys Ile Leu Glu Arg Thr Glu Ile Leu Asn Gln Glu Trp Lys
                20                  25                  30

Gln Arg Arg Ile Gln Pro Val
        35

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Lys Ile Leu Glu Arg Thr Gln Ile Leu Asn Gln Glu Trp Lys Gln
1               5                   10                  15

Arg Arg

<210> SEQ ID NO 56
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid
<220> FEATURE:
<221> NAME/KEY: MOD_RES
<222> LOCATION: (13)..(13)
<223> OTHER INFORMATION: Any stapling amino acid
<220> FEATURE:
<221> NAME/KEY: MOD_RES
<222> LOCATION: (17)..(17)
<223> OTHER INFORMATION: Any stapling amino acid

<400> SEQUENCE: 56

Phe Ser Ser Asn Arg Xaa Lys Ile Leu Xaa Arg Thr Xaa Ile Leu Asn
1               5                   10                  15

Xaa Glu Trp Lys Gln Arg Arg Ile Gln Pro Val
            20                  25
```

STABLIZED EZH2 PEPTIDES

STATEMENT OF UNITED STATES GOVERNMENT SUPPORT

This invention was made with government support under grant numbers U01CA105423 and R01GM090299 awarded by the National Institutes of Health. The government has certain rights in the invention.

CROSS-REFERENCE TO RELATED APPLICATIONS

The present application is the National Phase of International Application Serial No. PCT/US2014/025587, filed on Mar. 14, 2014, which claims the benefit of U.S. Provisional Patent Application Ser. No. 61/790,023, filed on Mar. 15, 2013, both of which are herein incorporated by reference in their entirety.

TECHNICAL FIELD

This disclosure relates to structurally stabilized therapeutic peptides related to enhancer of zeste homolog 2 (EZH2), histone lysine N-methyltransferase and methods of using such peptides in the treatment of cancer.

SEQUENCE LISTING

The instant application contains a Sequence Listing which has been submitted electronically in ASCII format and is hereby incorporated by reference in its entirety. Said ASCII copy, created on Mar. 12, 2014, is named 00530-0309WO1_SL.txt and is 30,362 bytes in size.

BACKGROUND

Enhancer of zeste homolog2 (EZH2) is a SET-domain-containing histone lysine N-methyltransferase that participates in the epigenetic regulation of cell lineage determination and homeostasis. EZH2 forms the Polycomb repressive complex2 (PRC2) with embryonic ectoderm development (EED) and suppressor of zeste 12 homolog (SUZ12) to catalyze histone H3 Lys27 trimethylation, and hyperactivity of this enzymatic function has been linked to aberrant repression of tumor suppressor genes in diverse cancers.

Epigenetic modifications of DNA and histones by a variety of protein complexes produce combinatorial codes of chromatin modification, amplifying the complexity of how genetically encoded information is employed. Such epigenetic information is decoded by "reader" proteins that, in conjunction with transcription factors, regulate the differential expression of genes during development and homeostasis. Two broad classes of protein complexes, Trithorax (trxG) and Polycomb (PcG), are responsible for the deposition of histone marks that dictate whether a gene is activated or repressed, respectively[1-5]. TrxG generally maintains an 'on state' of gene expression by catalyzing methylation of Lys4 of Histone H3 (H3K4), while PcG maintains an 'off state' by catalyzing trimethylation of Lys27 of Histone H3 (H3K27). In mammals, there are two distinct PcG complexes, Polycomb repressive complex 1 (PRC1) and Polycomb repressive complex 2 (PRC2). PRC2 catalyzes trimethylation of H3K27 and, at certain sites, facilitates the recruitment of PRC1 to methylated histones to repress target genes[3,4]. PRC2 is composed of three essential core components, enhancer of zeste homolog 2 (EZH2), suppressor of zeste 12 (SUZ12) and embryonic ectoderm development (EED). The conserved suppressor of variegation, enhancer of zeste, trithorax (SET) domain of EZH2 represents the active site for catalysis of H3K27 methylation[6].

In addition to the established roles of the epigenetic machinery in cell homeostasis and development, recent studies have implicated discrete protein subcomponents, such as EZH2, in the pathogenesis of diverse cancers[7-12]. EZH2 overexpression has been linked to repression of tumor suppressor genes and derepression of genes involved in metastasis[13-16]. In certain cancers, this EZH2 deregulation has been linked to pathologic alterations in microRNA levels[17-20]. Somatic mutations that alter the substrate specificity and functional activity of EZH2 have also been found in B cell non-Hodgkin's lymphoma[21-24]. Correspondingly, reduced expression of EZH2 by shRNA or siRNA induces proliferative arrest in cancer cell lines that overexpress EZH2[25,26]. The genetic ablation of Ezh2 alone prevents the development of a murine T cell lymphoma that results from inactivation of Snf5, a core component of the Swi/Snf remodeling complex[27]. Collectively, these findings implicate EZH2 deregulation in the development and maintenance of cancer.

SUMMARY

The present disclosure provides structurally stabilized peptides related to (e.g., sharing sequence homology with) portions or fragments of Enhancer of zeste homolog2 (EZH2), and methods for using such stabilized peptides as therapeutic and/or prophylactic agents.

In some aspects, the present disclosure provides internally cross-linked polypeptides comprising the amino acid sequence $A_0B_0C_0D_0E_0F_0G_0 A_1B_1C_1D_1E_1F_1G_1 A_2B_2C_2D_2E_2F_2G_2 A_3B_3C_3D_3E_3F_3G_3 A_4$ (SEQ ID NO:1) wherein $A_0$ is S or a conservative substitution; $B_0$ is M or a conservative substitution; $C_0$ is F or a conservative substitution; $D_0$ is S or a conservative substitution; $E_0$ is S or a conservative substitution; $F_0$ is N or a conservative substitution; $G_0$ is R or a conservative substitution; $A_1$ is Q or a conservative substitution or a staple to $E_1$; $B_1$ is K or a conservative substitution; $C_1$ is I or a conservative substitution; $D_1$ is L or a conservative substitution; $E_1$ is E, Q or a conservative substitution or a staple to $A_1$; $F_1$ is R or a conservative substitution; $G_1$ is T or a conservative substitution; $A_2$ is E, Q or a conservative substitution; $B_2$ is I or a conservative substitution; $C_2$ is L or a conservative substitution; $D_2$ is N or a conservative substitution; $E_2$ is Q or a conservative substitution; $F_2$ is E, Q or a conservative substitution; $G_2$ is W or a conservative substitution; $A_3$ is K or a conservative substitution $B_3$ is Q or a conservative substitution; $C_3$ is R or a conservative substitution; $D_3$ is R or a conservative substitution; $E_3$ is I or a conservative substitution; $F_3$ is Q or a conservative substitution; $G_3$ is P or a conservative substitution; $A_4$ is V or a conservative substitution; wherein the side chains of two amino acids separated by two, three or six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches. In some embodiments $C_0$, $F_0$, $G_0$, $B_1$, $C_1$, $F_1$, $C_2$, $D_2$, $F_2$, $G_2$, $C_3$, $E_3$, $G_3$ and $A_4$ are not substituted. Thus, in some embodiments, these residues are F, N, R, K, I, R, L, N, E, W, R, I, P and V, respectively.

In some embodiments, internally cross-linked polypeptides of the disclosure include the sequence SMFSSN-RQKILERTEILNQEWKQRRIQPV (SEQ ID NO:2), wherein: none, one or more (e.g., 1, 2, 3, 4, 5, 6, 7, 8, 9, 10, 11, 12, 13, 14, 15, 16, 17, 18) of the amino acids are replaced by a conservative amino acid substitution or, in some cases, a conservative substitution that does not alter the binding face of the peptide. In some cases, the internally cross-linked peptide is at least 80% (e.g., 80%, 85%, 90%, 95%, 98%, 99%, 99.5%, or 100%) identical to the sequence of SEQ ID NO:2. The amino acid side chains that are replaced by a cross-link are consider non-identical in calculating percent identity.

In some embodiments, internally cross-linked polypeptides of the disclosure comprises:

```
                                    (SEQ ID NO: 2)
SMFSSNRQKILERTEILNQEWKQRRIQPV;

(SEQ ID NO: 40)
FSSNRQKILERTEILNQEWKQRRIQPV, (SEQ ID NO: 41)
FSSNRQKILERTQILNQEWKQRRIQPV, (SEQ ID NO: 42)
RRSMFSSNRQKILERTEILNQEWKQRRIQPV, (SEQ ID NO: 43)
RRFSSNRQKILERTEILNQEWKQRRIQPV, (SEQ ID NO: 44)
RRFSSNRQKILERTQILNQEWKQRRIQPV, (SEQ ID NO: 45)
RSMFSSNRQKILERTEILNQEWKQRRIQPV, (SEQ ID NO: 46)
RFSSNRQKILERTEILNQEWKQRRIQPV, (SEQ ID NO: 47)
RFSSNRQKILERTQILNQEWKQRRIQPV, (SEQ ID NO: 48)
SMFSSNRQKILERTEILNQEWKQRRIQPVRR, (SEQ ID NO: 49)
FSSNRQKILERTEILNQEWKQRRIQPVRR, (SEQ ID NO: 50)
FSSNRQKILERTQILNQEWKQRRIQPVRR, (SEQ ID NO: 51)
SMFSSNRQKILERTEILNQEWKQRRIQPVR, (SEQ ID NO: 52)
FSSNRQKILERTEILNQEWKQRRIQPVR,
and (SEQ ID NO: 53)
FSSNRQKILERTQILNQEWKQRRIQPVR,
``` wherein the side chains of two amino acids separated by three or six amino acids comprises an internal staple selected from Table 1 (FIG. 43). In addition, 1, 2, 3, 4, 5, 6, 7, 8, 9, 10, 11, 12 or 13 of the amino acids can be substituted, preferably conservatively. Within the sequence: S M F S S N R Q K I L E R T E I L N Q E W K Q R R I Q P V (SEQ ID NO:2) the underlined residues are preferably not substituted. In some embodiments there is an internal cross-link (staple) between $8^{th}$ and $12^{th}$ amino acids of SEQ ID NO:1 (i.e., the side chains of these resides is replaced by a staple. In SEQ ID NO:1, the is preferably an internal cross-link (staple) between $A_1$ and $E_1$. Some cases the E in SEQ ID NO:2 (or SEQ ID NO:1) are replaced by Q. In some cases the stabilized peptides do not include any E and in some cases have a get positive charge.

In some embodiments negatively charged residues in any of the stabilized peptides are replaced by Q or R.

In some embodiments an RR dipeptide is appended to the amino or carboxy terminus of the stapled peptide.

In preferred embodiments, the staple is an alkyl or alkynl.

In some embodiments, internally cross-linked polypeptides of the disclosure include an internal staple replacing the side chains of two amino acids separated by three or six amino acids comprises an internal staple selected from Table 1 (FIG. 43).

In some embodiments, internally cross-linked peptides are selected from the group consisting of SEQ ID NOs:2-39. In some embodiments, the internal staples and/or the internal stitch replacing the side chains of the three amino acids includes an internal stitch selected from Table 1 (FIG. 43). In some embodiments, the internal staples and/or the internal stitch comprises at least two internal staples (replacing the side chains of 4 amino acids, i.e., each staple is between two amino acids separated by 3 amino acids). In some embodiments, the internal staples and/or the internal stitch comprises a combination of at least one internal staple and an internal stitch. In some embodiments, the internal stitch replaces the side chain of a first amino acid and a second and a third amino acid thereby cross-linking the first amino acid (which lies between the second and third amino acids) to the second and third amino acid via an internal cross-link, wherein the first and second amino acid are separated by two, three, or six amino acids, the first and the third amino acids are separated by two, three, or six amino acids, and the second and third amino acids are distinct amino acids. In some embodiments, the internal stitch replacing the side chains of the three amino acids cross-links a pair of amino acids separated by two, three, or six amino acids. In some embodiments, the side chains of the four amino acids of the internally cross-linked polypeptides of the disclosure are replaced by two distinct internal staples. In some embodiments, a first of the two distinct internal staples cross-links a first pair of amino acids separated by two, three, or six amino acids, and a second of the at least two distinct internal staples cross-links a second pair of amino acids separated by two, three, or six amino acids. In some embodiments, internally cross-linked polypeptides of the disclosure are selected from the group consisting of SEQ ID NOs:3-41. In some embodiments, internally cross-linked polypeptides of the disclosure include internal staples, internal stitches, or a combination of internal staples and internal stitches replacing the side chains of at least four amino acids, such as at least one staple and at least one stitch. In some embodiments, the at least one staple cross-links a pair of amino acids separated by two, three, or six amino acids and the at least one stitch cross-links a first amino acid to a second amino acid and a third amino acid, wherein the first and second amino acid are separated by two, three, or six amino acids, the first and the third amino acids are separated by two, three, or six amino acids, and the second and third amino acids are distinct amino acids. In some embodiments, such staples are selected from Table 1 (FIG. 43).

In some aspects, the disclosure provides pharmaceutical compositions that include one or more internally cross-linked polypeptides of the disclosure. In some embodiments, such pharmaceutical compositions can also include one or more medicaments for the treatment of cancer and/or the alleviation of one or more symptoms associated with cancer.

In some aspects, the disclosure provides kits for identifying agents that interact with a stabilized EZH2 peptide. Such kits can include one or more internally cross-linked polypeptides of the disclosure and EED or a portion of EED that binds EZH2. In some aspects the disclosure provides a method for identifying compounds that disrupts the interaction of EZH2 with EED the method comprising contacting test compound with a stabilized peptide described herein (e.g., one of SEQ ID NOS: 3-41, preferably SEQ ID NO:27); and detecting the level of binding between the stabilized peptide and the EED peptide the presence of an test agent, wherein a change in the level of binding between the stabilized peptide and the EED peptide indicates that the agent is a candidate agent that binds to the EED and decreases binding to EZH2. In some embodiments, these methods can include selecting the candidate agent, and optionally, administering the candidate agent to an animal model of a cancer, e.g., to determine if the agent inhibits the cancer.

In some aspects, the disclosure provides methods for treating cancer in a subject. These methods can include selecting a subject suffering from cancer; and administering to the subject an effective amount of the stabilized peptides of claims described herein. In some embodiments, methods include assessing a level of EZH2 in the subject before and after treatment; and continuing treatment until a decrease in the level EZH2 is observed.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

FIG. 1A|Examples of non-natural amino acids containing olefinic tethers that can be used to generated hydrocarbon stapled EZH2 peptides.

FIG. 1B|Examples of single staple compositions spanning i, i+3; i, i+4, and i, i+7 positions for singly stapled EZH2 peptides.

FIG. 8|Enhanced cellular penetrance of E54Q and E54Q/E59Q mutants of SAH-EZH2$_A$(42-68), as measured by fluorescence scan of lysates from FITC-peptide treated MLL-AF9 leukemia cells.

FIG. 9|EED-binding affinity of SAH-EZH2$_A$ E54Q (SAH-EZH2) and SAH-EZH2$_A$ E54Q/E59Q (SAH-EZH2mut) peptides, as measured by fluorescence polarization. Data represent mean±s.e.m. for experiments performed in triplicate.

FIG. 10|Comparative binding of SAH-EZH2 glutamate mutants to purified HA-EED (40 nM final concentration) as assessed by anti-FITC pull-down and EED western analysis.

FIG. 29B 1Real Time qPCR analysis of macrophage/monocyte-specific marker expression. SAH-EZH2 treated (8 days) cells exhibit increased expression of macrophage/monocyte specific markers. pAdam<0.11, pFcer1a<0.14, pACE<0.29.

```
                                              (SEQ ID NO: 55)
(QKILERTQILNQEWKQRR, (SEQ ID NO: 27)
FSSNRXKILXRTQILNQEWKQRRIQPV, (SEQ ID NO: 56)
FSSNRXKILXRTXILNXEWKQRRIQPV
```

Figure 39:
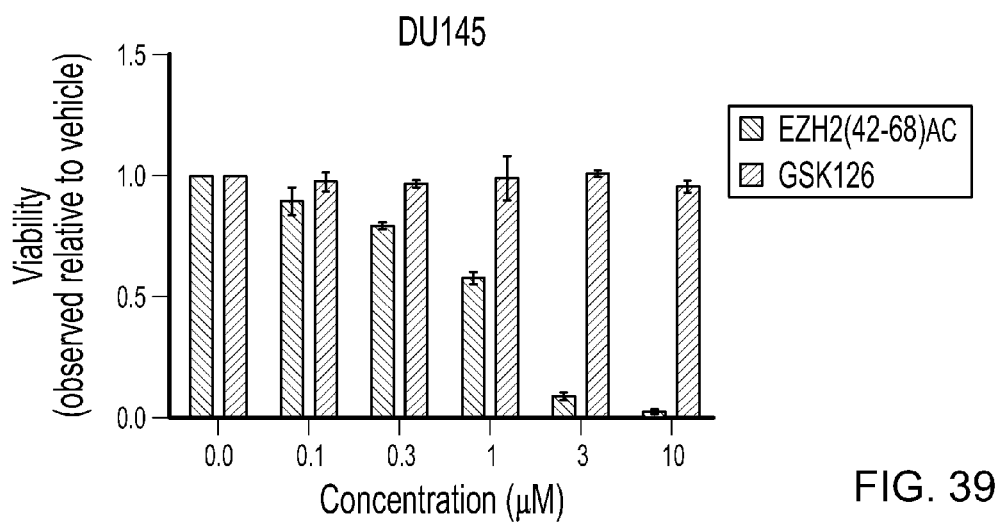

FIG. 39|Graphs demonstrating the anti-proliferative effect of a doubly stapled SAH-EZH2(42-68)$_{AC}$ (FSSN-RXKILXRTXILNXEWKQRRIQPV (SEQ ID NO:56) peptide on the breast cancer cell line MDA-MB231 and the prostate cancer cell line DU145.

FIG. 40|Graphs demonstrating the anti-proliferative activity of a doubly stapled SAH-EZH2(42-68)$_{AC}$ peptide on Ewing Sarcoma cell line TC-71 and neuroblastoma cell line Kelly.

FIG. 41|Graph demonstrating anti-proliferative effect of a doubly stapled SAH-EZH2(42-68)$_{AC}$ peptide on the chronic myelogenous leukemia cell line K562.

Figure 42:
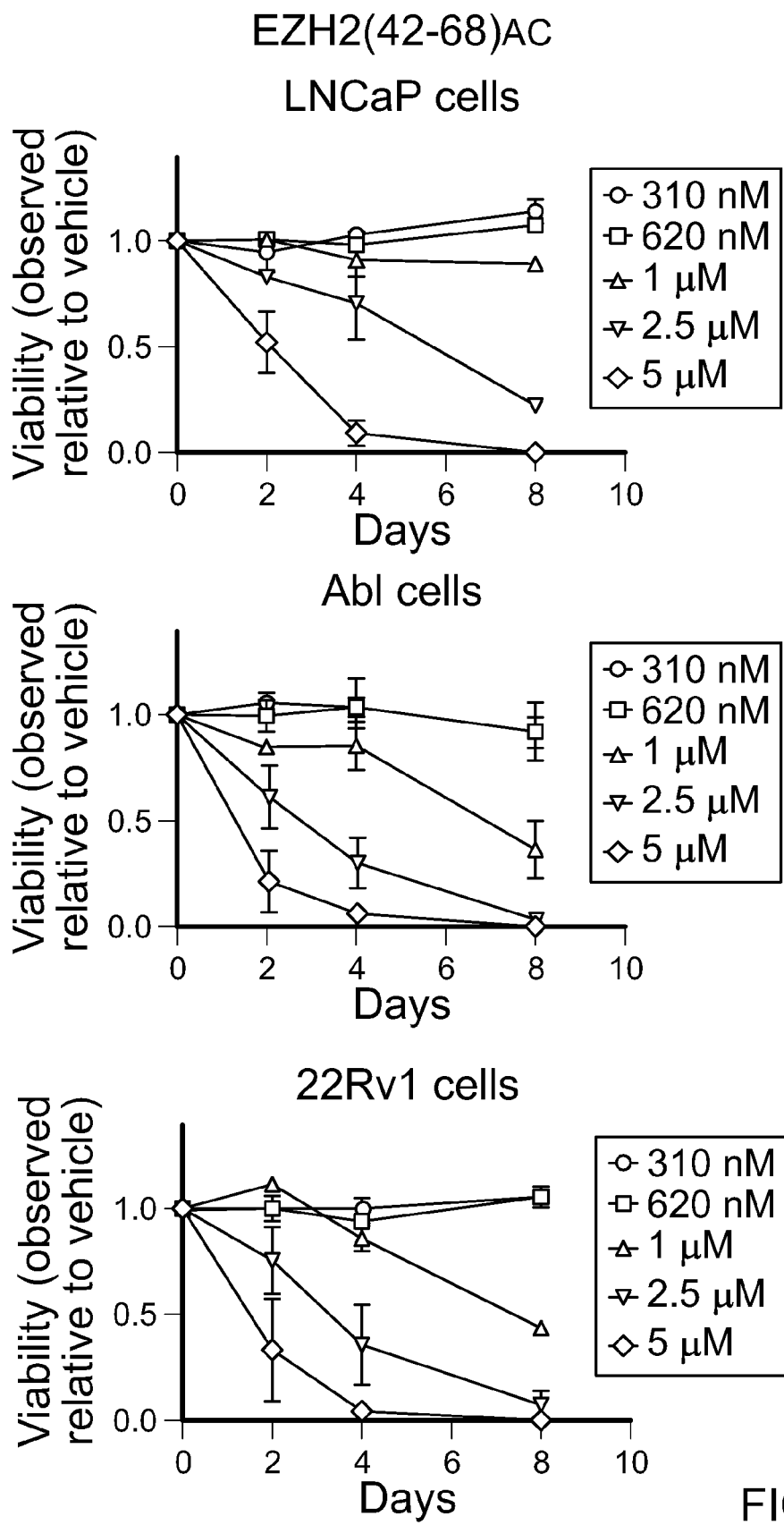

FIG. 42|Graphs demonstrating the anti-proliferative effect of a doubly stapled SAH-EZH2(42-68)$_{AC}$ peptide on prostate cancer cell lines.

Figure 43:
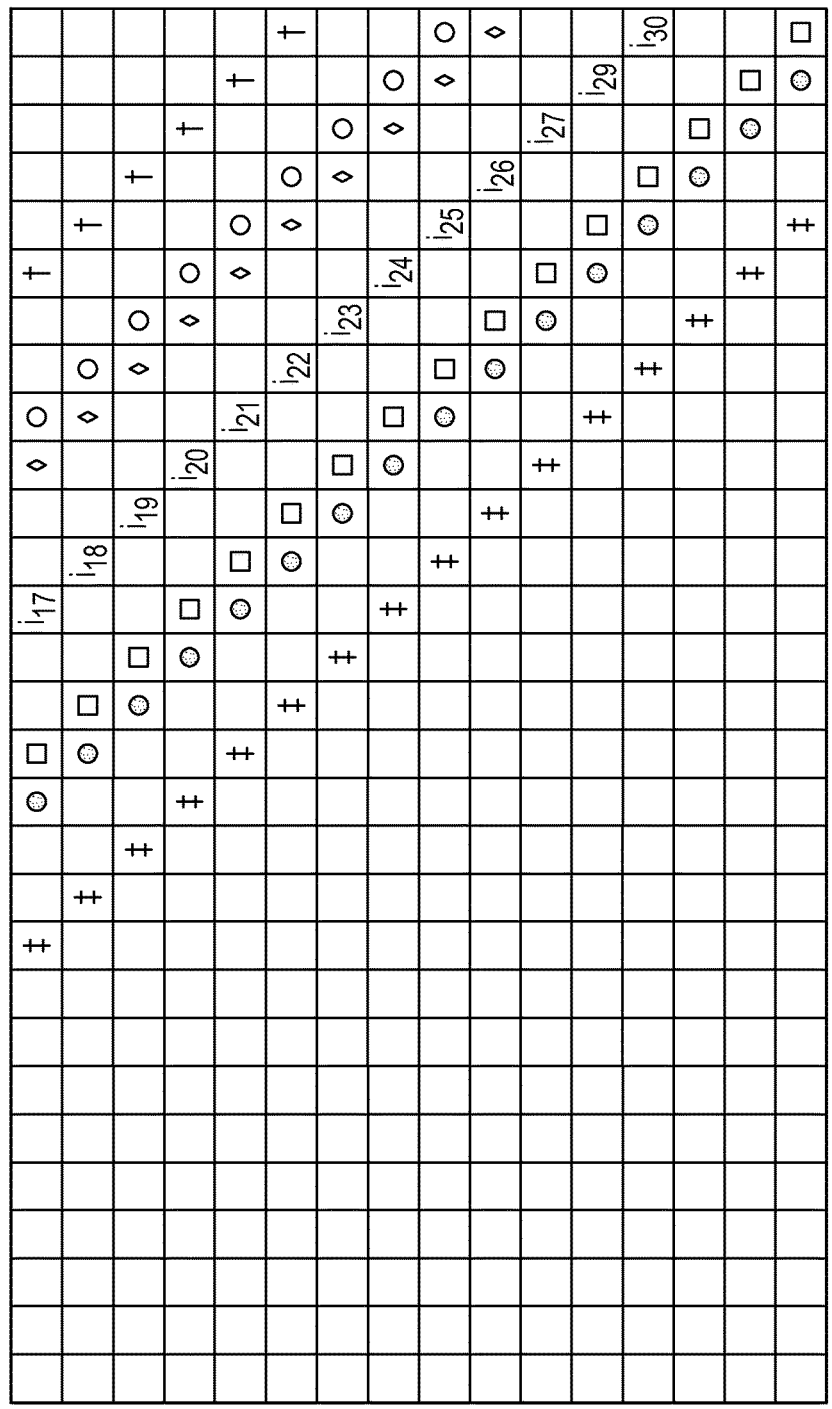

FIG. 43|A table depicting various stapled peptides (Table 1). Sequence disclosed as SEQ ID NO: 2.

DETAILED DESCRIPTION

Stabilized Peptides

The present disclosure provides structurally stabilized peptides related to portions or fragments of EZH2 (referred to at times as stabilized α-helices of EZH2 or SAH-EZH2) comprising at least two modified amino acids joined by an internal (intramolecular) cross-link (or staple), wherein the at least two amino acids are separated by 2, 3, or, 6 amino acids. Stabilized peptides herein include stapled and/or stitched peptides.

Amino acids are the building blocks of the peptides herein. The term "amino acid" refers to a molecule containing both an amino group and a carboxyl group as well as a side chain Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (Q), Glu (E), Gly (G), His (H), Ile (I), leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnatural beta-amino acids Amino acids used in the construction of peptides of the present invention can be prepared by organic synthesis, or obtained by other routes, such as, for example, degradation of or isolation from a natural source.

There are many known unnatural amino acids any of which may be included in the peptides of the present invention. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(=O)C$_6$H$_5$; —CF$_3$; —CN; -halo; —NO2; CH$_3$), disubstituted phenylalanines, substituted tyrosines (e.g., further substituted with -Q=O)C$_6$H$_5$; —CF$_3$; —CN; -halo; —NO$_2$; CH$_3$), and statine. Additionally, amino acids can be derivatized to include amino acid residues that are hydroxylated, phosphorylated, sulfonated, acylated, and glycosylated, to name a few.

A "peptide" or "polypeptide" comprises a polymer of amino acid residues linked together by peptide (amide) bonds. The term(s), as used herein, refers to proteins, polypeptides, and peptide of any size, structure, or function. Typically, a peptide or polypeptide will be at least three amino acids long. A peptide or polypeptide may refer to an individual protein or a collection of proteins. In some instances, peptides can include only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof "Dipeptide" refers to two covalently linked amino acids.

In some instances, peptides can include (e.g., comprise, consist essentially of, or consist of) at least seven (e.g., 7, 8, 9, 10, 11, 12, 13, 14, 15, 16, 17, 18, 19, 20, 21, 22, 23, 24, 25, 26, 27, 28 or 29) contiguous amino acids of: A) the amino acid sequence SMFSSNRQKILERTEILN-QEWKQRRIQPV (SEQ ID NO:2); B) the amino acid sequence FSSNRQKILERTEILNQEWKQRRIQPV (SEQ ID NO:40); C) the amino acid sequence FSSN-RQKILERTQILNQEWKQRRIQPV (SEQ ID NO:41), or D) the amino acid sequence: $A_0B_0C_0D_0E_0F_0G_0$ $A_1B_1C_1D_1E_1F_1G_1$ $A_2B_2C_2D_2E_2F_2G_2A_3B_3C_3D_3E_3F_3G_3$ $A_4$ (SEQ ID NO:1) wherein:

wherein $A_0$ is S or a conservative substitution; $B_0$ is M or a conservative substitution; $C_0$ is F or a conservative substitution; $D_0$ is S or a conservative substitution; $E_0$ is S or a conservative substitution; $F_0$ is N or a conservative substitution; $G_0$ is R or a conservative substitution; $A_1$ is Q or a conservative substitution or a staple to $E_1$; $B_1$ is K or a conservative substitution; $C_1$ is I or a conservative substitution; $D_1$ is L or a conservative substitution; $E_1$ is E, Q or a conservative substitution or a staple to $A_1$; $F_1$ is R or a conservative substitution; $G_1$ is T or a conservative substitution; $A_2$ is E, Q or a conservative substitution; $B_2$ is I or a conservative substitution; $C_2$ is L or a conservative substitution; $D_2$ is N or a conservative substitution; $E_2$ is Q or a conservative substitution; $F_2$ is E, Q or a conservative substitution; $G_2$ is W or a conservative substitution; $A_3$ is K or a conservative substitution $B_3$ is Q or a conservative substitution; $C_3$ is R or a conservative substitution; $D_3$ is R or a conservative substitution; $E_3$ is I or a conservative substitution; $F_3$ is Q or a conservative substitution; $G_3$ is P or a conservative substitution; $A_4$ is V or a conservative substitution; wherein the side chains of two amino acids separated by two, three or six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches. In some embodiments $C_0, F_0, G_0, B_1, C_1, F_1, C_2, D_2, F_2, G_2, C_3, E_3, G_3$ and $A_4$ are not substituted.

Peptides can also include at least seven (e.g., 7, 8, 9, 10, 11, 12, 13, 14, 15, 16, 17, 18, 19, 20, 21, 22, 23, 24, 25, 26, 27, 28 or 29) contiguous amino acids of: A) the amino acid sequence: SMFSSNRQKILERTEILNQEWKQRRIQPV (SEQ ID NO:2); B) the amino acid sequence FSSN-RQKILERTEILNQEWKQRRIQPV (SEQ ID NO:40); C) the amino acid sequence FSSNRQKILERTQILN-QEWKQRRIQPV (SEQ ID NO:41), wherein the peptide has a reinforced or stabilized alpha helical secondary structure (e.g., wherein the peptide includes at least one internal crosslink) and wherein the percent identity calculation includes the cross-linked amino acids and the cross-linked amino acids are considered non-conservative substitutions. In some cases the internal cross-link replaces the side chains of two amino acids separated by 3 amino acids. In some cases the internal cross-link replaces the side chains of two amino acids separated by 6 amino acids. In some cases there are two internal cross-links, each replacing the side chains of a pair of amino acids separated by 3 amino acids and each cross-link being on essentially the same face of the resulting essentially alpha-helical peptide. In the peptides of SEQ ID NOs:2, 40 and 41, the amino acid residues corresponding to the underlined residues in the sequence S M F S S N R Q K I L E R T E I L N Q E W K Q R R I Q P V (SEQ ID NO:2) are not substituted, wherein the peptide has a reinforced or stabilized alpha helical secondary structure (e.g., wherein the peptide includes at least one internal crosslink).

In some instances, the peptide has or can be induced to have alpha helical secondary structure.

In some instances, SEQ ID NO:1 corresponds to or is (SEQ ID NO:2). In some instances, stabilized peptides can have at least 80% (e.g., 80%, 85%, 90%, 95%, 98%, 99%, 99.5%, or 100%) identity to SEQ ID NO: 2 or can include SEQ ID NO:1 or SEQ ID NO:2 with one or more (e.g., 1, 2, 3, 4, 5, 6, 7, 8, 9, 10, 11, 12, 13, 14, 15, 16, 17, 18, preferably 1-2, 1-3, 1-4 or 1-5) conservative amino acid substitutions. In some cases, the stabilized peptide has the sequence of SEQ ID NO:1 with one or two staples (e.g., one staple between two amino acids separated by 3 (or 6) amino acids or two staples each between two amino acids that are separated by 3 (or 6) amino acids). In addition, 1, 2, 3, 4 or 5 of the amino acids (whose side chains are not replaced with a staple) in this stabilized peptide can be replaced by a conservative substitution.

In some cases the staple is between $A_1$ and $E_1$, of SEQ ID NO:1.

Methods for detecting any reduction in binding can include comparing binding affinity following conservative amino acid substitution, wherein any amino acid substitution that reduces (e.g., substantially reduces) binding are not conservative amino acid substitutions. In some embodiments, substantially reduced binding can include binding that is 10%, 20%, 30%, 40%, 50%, 60%, 70%, 80%, 90%, 95%, 98%, 99%, or 100% less than binding of the unmodified stabilized peptide to EED. Methods for assessing interaction between a stabilized EZH2 peptide and EED are disclosed herein. Methods for identifying the interactive face of a peptide are known in the art.

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

As disclosed above, peptides herein include at least two modified amino acids that together form an internal (intramolecular) cross-link (or staple), wherein the at least two modified amino acids are separated by: (A) two amino acids (i.e., i, i+3, shown in Table 1 (FIG. 43) as ◊), (B) three amino acid (i.e., i, i+4, shown in Table 1 (FIG. 43) as ○), or (C) six amino acids (i.e., i, i+7, shown in Table 1 (FIG. 43) as †).

In the case of a cross-link between i and i+3 the cross-link can be a C7 alkylene or alkenylene. In the case of a cross-between i and i+4 the cross-link can be a C8 alkylene or alkenylene. In the case of a cross-link between i and i+7 the cross-link can be a C11, C12 or C13 alkylene or alkenylene. When the cross-link is an alkenylene there can one or more double bonds.

In the case of a cross-link between i and i+3 the cross-link can be a C6, C7, or C8 alkyl or alkene (e.g., a C6 alkene having a single double bond). In the case of a cross-link between i and i+4 the cross-link can be a C8 alkyl or alkene. In the case of a cross-link between i and i+7 the cross-link can be a C11, C12 or C13 alkyl or alkene (e.g., a C11 alkene having a single double bond). When the cross-link is an alkene there can be one or more double bonds.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (Blackwell et al., J. Org. Chem., 66: 5291-5302, 2001; Angew et al., Chem. Int. Ed. 37:3281, 1994). As used herein, the term "peptide stapling," includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed in WO 2008121767 and in WO 2010/068684, which are both hereby incorporated by reference. In some instances, staples, as used herein, can retain the unsaturated bond or can be reduced (e.g., as mentioned below in the stitching paragraph description).

While many peptide staples have all hydrocarbon cross-links, other type of cross-links or staples can be used. For example, triazole-containing (e.g., 1,4 triazole or 1,5 triazole) crosslinks can be used (Kawamoto et al. 2012 Journal of Medicinal Chemistry 55:1137; WO 2010/060112).

Stapling of a peptide using all-hydrocarbon cross-link has been shown to help maintain its native conformation and/or secondary structure, particularly under physiologically relevant conditions (Schafmiester et al., J. Am. Chem. Soc., 122:5891-5892, 2000; Walensky et al., Science, 305:1466-1470, 2004).

Stapling the polypeptide herein by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's thermal stability, may increase the peptide's hydrophobicity, may allow for better penetration of the peptide into the target cell's membrane (e.g., through an energy-dependent transport mechanism such as pinocytosis), and/or may lead to an improvement in the peptide's biological activity relative to the corresponding uncrosslinked (e.g., "unstitched" or "unstapled") peptide.

Stabilized peptides herein include at least two internally cross-linked or stapled amino acids, wherein the at least two amino acids are separated by two (i.e., i, i+3, shown in Table 1 (FIG. 43)), three (i.e., i, i+4, shown in Table 1 (FIG. 43)), or six (i.e., i, i+7, shown in Table 1 (FIG. 43)) amino acids. While at least two amino acids are required to support an internal cross-link (e.g., a staple), additional pairs of internally cross-linked amino acids can be included in a peptide, e.g., to support additional internal cross-links (e.g., staples). For example peptides can include 1, 2, 3, 4, 5, or more staples. Examples of peptide staples are illustrated in the figures. Cross-linked peptides (e.g., stapled and/or stitched peptides) are generally referred to herein as SAH peptides.

Alternatively or in addition, peptides can include three internally cross-linked or stitched amino acids, e.g., yielding two staples arising from a common origin. A peptide stitch includes at least three internally cross-linked amino acids, wherein the middle of the three amino acids (referred to here as the core or central amino acid and shown in Table 1 (FIG. 43) as "i") forms an internal cross-link (between alpha carbons) with each of the two flanking modified amino acids. The alpha carbon of the core amino acid has side chains that are internal cross-links to the alpha carbons of other amino acids in the peptide, which can be saturated or not saturated Amino acids cross-linked to the core amino acid can be separated from the core amino acid in either direction by 2, 3, or 6 amino acids (e.g., i, i-3, i, i-4, i, i-7 (shown in Table 1 (FIG. 43)), i, i+3, i, i+4, i, i+7 (shown in Table 1 (FIG. 43)), where "i" is the core amino acid). The number of amino acids on either side of the core (e.g., between the core amino acid and an amino acid cross-linked to the core) can be the same or different. Examples of such three amino acid containing peptide stitches are illustrated in FIG. 1D. In some instances, a stitch can include 3, 4, 5, or more internally cross-linked amino acids. In some instances, peptides can include 1, 2, 3, 4, 5, or more stitches.

In some embodiments, peptides herein can include a combination of at least one (e.g., 1, 2, 3, 4, or 5) staple and at least one (e.g., 1, 2, 3, 4, or 5) stitch.

Cross-linked peptides (e.g., stapled and/or stitched peptides) are generally referred to herein as SAHF peptides. Peptides can include cross-linked amino acids at one or more of the positions illustrated in Table 1.

In FIG. 43 (Table 1) positions of cross-links are indicated by symbols and the letter "i". For example, $i_{10}$ (C1) can be linked via a i+3 staple to $F_1$ or $G_0$ (also called i-3) or a i+4 staple to G1 or $F_0$ (also called i-4) or a i+7 staple to $C_2$ or $C_0$ (also called i-7). Of course, $i_{10}$ (C1) could be stitched to, for example $F_1$ (i+3) and CO (i-7). In Table 1 (FIG. 43), the first row shows SEQ ID NO:1 and the second row shows an exemplary embodiment of SEQ ID NO: 1, SEQ ID NO:2.

Internal cross-links (e.g., staples and/or stitches) can be positioned on amino acids within a peptide to conserve the structural relationship of amino acids in the binding or interacting face of the peptide (e.g., to preserve the binding interface of a peptide). Alternatively, staples can placed on the interacting face as long as binding affinity or activity is not altered. Exemplary cross-linked peptides include SEQ ID NOs: 3-39.

In some instances, peptides herein do not include an internal cross-link that disrupts the binding interface of SEQ ID NO:2. For examples, in some instances, peptides do not include an internal cross-link between two or more (e.g., 2, 3, 4, 5, 6, 7, 8, 9, 10, or more) amino acids on the interacting face of SEQ ID NO:2.

Selection of amino acids for modification (e.g., to support an internal cross-link) can also be facilitated by staple scanning. The term "staple scan" refers to the synthesis of a library of stapled peptides whereby the location of the i and i+3; i and i+4; and i and i+7 single and multiple staple, or stitches, are positioned sequentially down the length of the peptide sequence, sampling all possible positions, to identify desired or optimal properties and activities for the stapled or stitched constructs. Examples of staple scanning methods are illustrated in the figures.

Suitable tethers are described herein and in US 2005/0250680, PCT/US2008/058575, WO 2009/108261, and WO 2010/148335.

Amino acid side chains suitable for use in the peptides disclosed herein are known in the art. For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted.

As noted above an internal tether or cross-link can extend across the length of one helical turn (i.e., about 3.4 amino acids (i.e., i, i+3, or i, i+4) or two helical turns (i.e., about 7 amino acids (i.e., i, i+7). Accordingly, amino acids positioned at i and i+3; i and i+4; or i and i+7 are ideal candidates for chemical modification and cross-linking (see Table 1). Thus, for example, where a peptide has the sequence . . . $Xaa_1, Xaa_2, Xaa_3, Xaa_4, Xaa_5, Xaa_6, Xaa_7, Xaa_8, Xaa_9$ . . . (wherein, " . . . " indicates the optional presence of additional amino acids), cross-links between $Xaa_1$ and $Xaa_4$, or between $Xaa_1$ and $Xaa_5$, or between $Xaa_1$ and $Xaa_8$ are useful as are cross-links between $Xaa_2$ and $Xaa_5$, or between $Xaa_2$ and $Xa_6$, or between $Xaa_2$ and $Xaa_9$, etc.

Polypeptides can include more than one crosslink within the polypeptide sequence to either further stabilize the sequence or facilitate the stabilization of longer polypeptide stretches. If the polypeptides are too long to be readily synthesized in one part, independently synthesized, cross-linked peptides can be conjoined by a technique called native chemical ligation (Bang, et al., J. Am. Chem. Soc. 126:1377). Alternately, large peptides are routinely synthesized using a convergent approach whereby fully protected fragments are specifically and sequentially reacted to form the full length desired product, after final deprotection, such as in the industrial synthesis of Fuzeon.

The invention features a modified polypeptide of Formula (I),

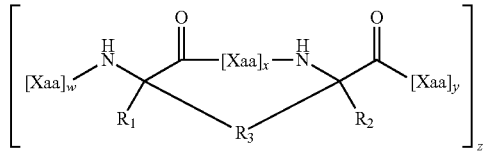

Formula (I)

or a pharmaceutically acceptable salt thereof,
wherein;
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;
$R_3$ is alkylene, alkenylene or alkynylene (e.g., a $C_6$, $C_7$, $C_8$, $C_{11}$, $C_{12}$ or $C_{13}$ alkylene), or $[R_4'—K—R_4]_n$; each of which is substituted with 0-6 $R_5$;
$R_4$ and $R_4'$ are independently alkylene, alkenylene or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);
$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;
K is O, S, SO, $SO_2$, CO, $CO_2$, $CONR_6$, or

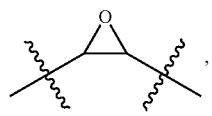 [SMILES: *C1OC1*]

aziridine, episulfide, diol, amino alcohol;
$R_6$ is H, alkyl, or a therapeutic agent;
n is 2, 3, 4 or 6;

x is an integer from 2-10;
w and y are independently an integer from 0-100;
z is an integer from 1-10 (e.g., 1, 2, 3, 4, 5, 6, 7, 8, 9, 10); and
each Xaa is independently an amino acid (e.g., one of the 20 naturally occurring amino acids or any naturally occurring non-naturally occurring amino acid);
wherein the polypeptide comprises at least 8 contiguous amino acids of SEQ ID NO:1, 2, 40, 41 or a variant thereof, or another polypeptide sequence described herein except that: (a) within the 8 contiguous (e.g., 9, 10, 11, 12, 13, 14, 15, 16, 17, 18, 19, 20, 21, 22, 23, 24, 24, 25, 26, 27, 28, 29, 30, 31, 32, 33, 34 or 35) amino acids of SEQ ID NO: 1, 2, 40, or 41 the side chains of at least one pair (e.g., one or two pairs) of amino acids separated by 2, 3 or 6 amino acids is replaced by the linking group, $R_3$, which connects the alpha carbons of the pair of amino acids as depicted in Formula I; and (b) the alpha carbon of the first of the pair of amino acids is substituted with $R_1$ as depicted in formula I and the alpha carbon of the second of the pair of amino acids is substituted with $R_2$ as depicted in Formula I.

In another aspect, the invention features a modified polypeptide of Formula (II),

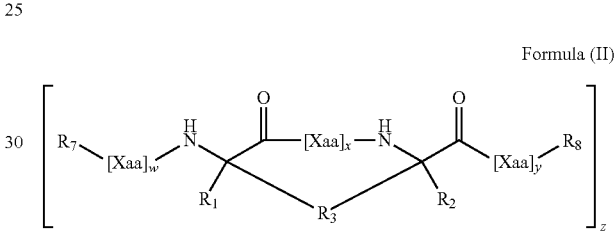

Formula (II)

or a pharmaceutically acceptable salt thereof,
wherein;
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;
$R_3$ is alkylene, alkenylene or alkynylene (e.g., a $C_6$, $C_7$, $C_8$, $C_{11}$, $C_{12}$ or $C_{13}$ alkylene) or $[R_4'—K—R_4]_n$; each of which is substituted with 0-6 $R_5$;
$R_4$ and $R_4'$ are independently alkylene, alkenylene or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);
$R_5$ is halo, alkyl, $OR_6$, $NHR_6$, $N(R_6)_2$, $SR_6$, $SOR_6$, $SO_2R_6$, $CO_2R_6$, $R_6$, a fluorescent moiety, or a radioisotope;
K is O, S, SO, $SO_2$, CO, $CO_2$, $CONR_6$, or

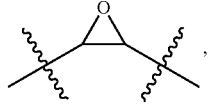

aziridine, episulfide, diol, amino alcohol, diamine;
$R_6$ is H, alkyl, or a therapeutic agent;
n is 2, 3, 4, 5, or 6;
x is an integer from 2-10;
w and y are independently an integer from 0-100;
z is an integer from 1-10 (e.g., 1, 2, 3, 4, 5, 6, 7, 8, 9, 10); and
each Xaa is independently an amino acid (e.g., one of the 20 naturally occurring amino acids or any naturally occurring non-naturally occurring amino acid);

R₇ is PEG, a tat protein, an affinity label, a targeting moiety, a fatty acid-derived acyl group, a biotin moiety, a fluorescent probe (e.g. fluorescein or rhodamine) linked via, e.g., a thiocarbamate or carbamate linkage;

R₈ is H, OH, NH₂, NHR$_{8a}$, NR$_{8a}$R$_{8b}$;

wherein the polypeptide comprises at least 8 contiguous amino acids (e.g., 9, 10, 11, 12, 13, 14, 15, 16, 17, 18, 19, 20, 21, 22, 23, 24, 24, 25, 26, 27, 28, 29, 30, 31, 32, 33, 34 or 35) of SEQ ID NO: 1, 2, 40, or 41, or another polypeptide sequence described herein except that: (a) within the 8 contiguous amino acids of SEQ ID NO: 1, 2, 40, 41 or another polypeptide sequence describe the side chains of at least one pair of amino acids separated by 2, 4 or 6 amino acids is replaced by the linking group, R₃, which connects the alpha carbons of the pair of amino acids as depicted in formula I; and (b) the alpha carbon of the first of the pair of amino acids is substituted with R₁ as depicted in Formula II and the alpha carbon of the second of the pair of amino acids is substituted with R₂ as depicted in Formula II.

In the case of Formula I or Formula II, the following embodiments are among those disclosed.

In cases where x=2 (i.e., i+3 linkage), R3 can be a C7 alkylene, alkenylene. Where it is an alkenylene there can one or more double bonds. In cases where x=6 (i.e., i+4 linkage), R₃ can be a C11, C12 or C13 alkylene or alkenylene. Where it is an alkenylene there can one or more double bonds. In cases where x=3 (i.e., i+4 linkage), R₃ can be a C8 alkylene, alkenylene. Where it is an alkenylene there can one or more double bonds.

In certain instances, the two alpha, alpha disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

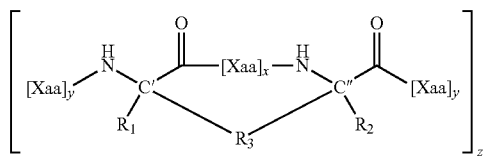

the C' and C" disubstituted stereocenters can both be in the R configuration or they can both be in the S configuration, for example when x is 3. When x is 6, the C' disubstituted stereocenter is in the R configuration and the C" disubstituted stereocenter is in the S configuration or the C' disubstituted stereocenter is in the S configuration and the C" disubstituted stereocenter is in the R configuration. The R₃ double bond may be in the E or Z stereochemical configuration. Similar configurations are possible for the carbons in Formula II corresponding to C' and C" in the formula depicted immediately above.

In some instances R₃ is [R₄—K—R₄']$_n$; and R₄ and R₄' are independently alkylene, alkenylene or alkynylene (e.g., each are independently a C1, C2, C3, C4, C5, C6, C7, C8, C9 or C10 alkylene, alkenylene or alkynylene In some instances, the polypeptide includes an amino acid sequence which, in addition to the amino acids side chains that are replaced by a cross-link, have 1, 2, 3, 4 or 5, 6, 7, 8, 9, 10, 11, 12 amino acid changes (e.g., conservative amino acid changes) in any of SEQ ID NOs: 1, 2, 40 or 41.

The tether can include an alkyl, alkenyl, or alkynyl moiety (e.g., C₆, C₈ or C₁₁ alkyl or a C₆, C₈ or C₁$_i$ alkenyl, or C₅, C₈ or C₁$_i$ alkynyl). The tethered amino acid can be alpha disubstituted (e.g., C₁-C₃ or methyl). [Xaa]$_y$ and [Xaa]$_w$ are peptides that can independently comprise at least 1, 2, 3, 4, 5, 6, 7, 8, 9, 10, 11, 12, 13, 14, 15, 16, 17, 18, 19, 20, 25, 26, 27, 28, 29, 30, 31, 32, 33, 34, or 35 contiguous amino acids of SEQ ID NOs: 1 or 2 and [Xaa]$_x$ is a peptide that can comprise 2, 3 or 6 contiguous amino acids of acids of SEQ ID NO: 1, 2, 40 or 41.

Peptides can contain one or more asymmetric centers and thus occur as racemates and racemic mixtures, single enantiomers, individual diastereomers and diastereomeric mixtures and geometric isomers (e.g. Z or cis and E or trans) of any olefins present. For example, peptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or may also be optically enriched. "Optically enriched," as used herein, means that the compound is made up of a significantly greater proportion of one enantiomer. In certain embodiments substantially free means that a composition contains at least about 90% by weight of a preferred enantiomer. In other embodiments the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al, Enantiomers, Racemates and Resolutions (Wiley Interscience, New York, 1981); Wilen, S. H., et al., Tetrahedron 33:2725 (1977); Eliel, E X. Stereochemistry of Carbon Compounds (McGraw-Hill, N Y, 1962); Wilen, S. H. Tables of Resolving Agents and Optical Resolutions p. 268 (EX. Eliel, Ed., Univ. of Notre Dame Press, Notre Dame, Ind. 1972). All such isomeric forms of these compounds are expressly included in the present invention.

Peptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

The symbol " ⤳ " when used as part of a molecular structure refers to a single bond or a trans or cis double bond.

The term "halo" refers to any radical of fluorine, chlorine, bromine or iodine. The term "alkyl" refers to a hydrocarbon chain that may be a straight chain or branched chain, containing the indicated number of carbon atoms. For example, C₁-C₁₀ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, C₂-C₁₀ indicates that the group may have from 2 to 10 (inclusive) carbon atoms in it. The term "lower alkenyl" refers to a C₂-C₈ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

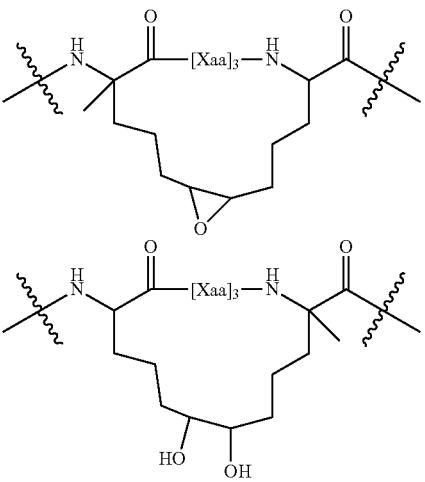

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body or track the location of the compound in the body. Alternatively, an additional therapeutic agent can be chemically attached to the functionalized tether (e.g., an anti-cancer agent such as rapamycin, vinblastine, taxol, etc.). Such derivatization can alternatively be achieved by synthetic manipulation of the amino or carboxy-terminus of the polypeptide or via the amino acid side chain. Other agents can be attached to the functionalized tether, e.g., an agent that facilitates entry of the polypeptide into cells.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

XO—$(CH_2CH_2O)_n$—$CH_2CH_2$—Y where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as —$NH(CH_2)_nC(O)$—, wherein n=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The stapled peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration.

In some embodiments, the stapled peptides disclosed herein have an enhanced ability to penetrate cell membranes (e.g., relative to non-stapled peptides).

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—$CH_2$); a thiomethylene bond (S—$CH_2$ or $CH_2$—S); an oxomethylene bond (O—$CH_2$ or $CH_2$-0); an ethylene bond ($CH_2$—$CH_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof.

α,α-Disubstituted non-natural amino acids containing olefinic side chains of varying length can be synthesized by known methods (Williams et al. J. Am. Chem. Soc., 113: 9276, 1991; Schafmeister et al., J. Am. Chem Soc., 122: 5891, 2000; and Bird et al., Methods Enzymol., 446:369, 2008; Bird et al, Current Protocols in Chemical Biology, 2011). For peptides where an i linked to i+7 staple is used (two turns of the helix stabilized) either one S5 amino acid and one R8 is used or one S8 amino acid and one R5 amino acid is used. R8 is synthesized using the same route, except that the starting chiral auxiliary confers the R-alkyl-stereoisomer. Also, 8-iodooctene is used in place of 5-iodopentene Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-$S_5$—OH, Fmoc-$R_8$—OH, Fmoc-$R_8$—OH, Fmoc-$S_8$—OH and Fmoc-$R_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, Calif.). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., Org. Synth., 80:31, 2003).

In some instances, peptides can include a detectable label. As used herein, a "label" refers to a moiety that has at least one element, isotope, or functional group incorporated into the moiety which enables detection of the peptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to a peptide at any position that does not interfere with the biological activity or characteristic of the inventive polypeptide that is being detected. Labels can include: labels that contain isotopic moieties, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc(Tc-99m), $^{111}$In, $^{123}$I, $^{125}$I, $^{169}$Yb, and $^{186}$Re; labels that include immune or immunoreactive moieties, which may be antibodies or antigens, which may be bound to enzymes {e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$I, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTC, $^{14}$C, $^{13}$N, $^{15}$O, $^{32}$P, $^{33}$P and $^{18}$F.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and Handbook of Fluorescent Probes and Research Products, Molecular Probes, 9th edition, 2002).

Again, methods suitable for obtaining (e.g., synthesizing), stapling, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafmeister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety) and are described herein (see, e.g., Example 1).

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the cross-linked polypeptides of the invention can be assayed, for example, using the methods described below.

Assays to Determine α-Helicity: Compounds are dissolved in an aqueous solution (e.g. 5 mM potassium phosphate solution at pH 7, or distilled $H_2O$, to concentrations of 25-50 µM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., Methods Enzymol. 130:208 (1986)).

Assays to Determine Melting Temperature (Tm): Cross-linked or the unmodified template peptides are dissolved in distilled $H_2O$ or other buffer or solvent (e.g. at a final concentration of 50 µM) and Tm is determined by measuring the change in ellipticity over a temperature range (e.g. 4 to 95° C.) on a spectropolarimeter (e.g., Jasco J-710, Aviv) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays: The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone and therefore may prevent or substantially retard proteolytic cleavage. The peptidomimetic macrocycles of the present invention may be subjected to in vitro enzymatic proteolysis (e.g. trypsin, chymotrypsin, pepsin) to assess for any change in degradation rate compared to a corresponding uncrosslinked or alternatively stapled polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E ~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time.

Peptidomimetic macrocycles and/or a corresponding uncrosslinked polypeptide can be each incubated with fresh mouse, rat and/or human serum (e.g. 1-2 mL) at 37° C. for, e.g., 0, 1, 2, 4, 8, and 24 hours. Samples of differing macrocycle concentration may be prepared by serial dilution with serum. To determine the level of intact compound, the following procedure may be used: The samples are extracted, for example, by transferring 100 µL of sera to 2 ml centrifuge tubes followed by the addition of 10 µL of 50% formic acid and 500 µL acetonitrile and centrifugation at 14,000 RPM for 10 min at 4+/−2° C. The supernatants are then transferred to fresh 2 ml tubes and evaporated on Turbovap under $N_2$<10 psi, 37° C. The samples are reconstituted in 100 µL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays: A key benefit of peptide stapling is the translation of in vitro protease resistance into markedly improved pharmacokinetics in vivo.

In Vitro Binding Assays: To assess the binding and affinity of peptidomimetic macrocycles and peptidomimetic precursors to acceptor proteins, a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

In Vitro Displacement Assays to Characterize Antagonists of Peptide-Protein Interactions: To assess the binding and affinity of compounds that antagonize the interaction between a peptide and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). A compound that antagonizes the interaction between the fluoresceinated peptidomimetic macrocycle and an acceptor protein will be detected in a competitive binding FPA experiment.

Binding Assays in Intact Cells: It is possible to measure binding of peptides or crosslinked polypeptides to their natural acceptors on or in intact cells by immunoprecipitation experiments.

Cellular Penetrability Assays: To measure the cell penetrability of peptides or crosslinked polypeptides, intact cells are incubated with fluoresceinated crosslinked polypeptides (10 µM) for 4 hrs in serum-free media or in media supplemented with human serum at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KineticScan.® HCS Reader.

Pharmaceutical Compositions

One or more of the stabilized peptides disclosed herein (e.g., one or more of SEQ ID NOs: 2-41) can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/ dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions).

In some instances, pharmaceutical compositions can include an effective amount of one or more stabilized peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of cancer).

Pharmaceutical compositions of this invention can include one or more peptides and any pharmaceutically acceptable carrier and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, the present disclosure provides methods for using any one or more of the peptides or pharmaceutical compositions (indicated below as 'X') disclosed herein in the following methods:

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., Infect. Immun, 58:2309-2312, 1990; Devi et al., Proc. Natl. Acad. Sci. USA 88:7175-7179, 1991; Li et al., Infect. Immun 57:3823-3827, 1989; Szu et al., Infect. Immun. 59:4555-4561,1991; Szu et al., J. Exp. Med. 166:1510-1524, 1987; and Szu et al., Infect. Immun 62:4440-4444, 1994). Polymeric carriers can be a natural or a synthetic material containing one or more primary and/or secondary amino groups, azido groups, or carboxyl groups. Carriers can be water soluble.

Methods of Treatment

The disclosure includes methods of using the peptides herein for the prophylaxis and/or treatment of cancer. The terms "treat" or "treating," as used herein, refers to partially or completely alleviating, inhibiting, ameliorating, and/or relieving the disease or condition from which the subject is suffering.

In general, methods include selecting a subject and administering to the subject an effective amount of one or more of the peptides herein, e.g., in or as a pharmaceutical composition, and optionally repeating administration as required for the prophylaxis or treatment of a cancer.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Treatment Methods

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. For example, effective amounts can be administered at least once.

EXAMPLES

Described below are internally cross-linked peptides related to EZH2 (SAH-EZH2) peptides that directly target EED, dissociate the EZH2/EED complex, and thereby reduce both EZH2 protein levels and H3Lys27 trimethylation. MLL-AF9 leukemia cells, which are dependent on the catalytic activity of PRC2, undergo growth arrest and monocyte/macrophage differentiation upon treatment with SAH-EZH2.

Example 1

Synthesis and EED-Binding Activity of SAH-EZH2 Peptides

Figure 2:
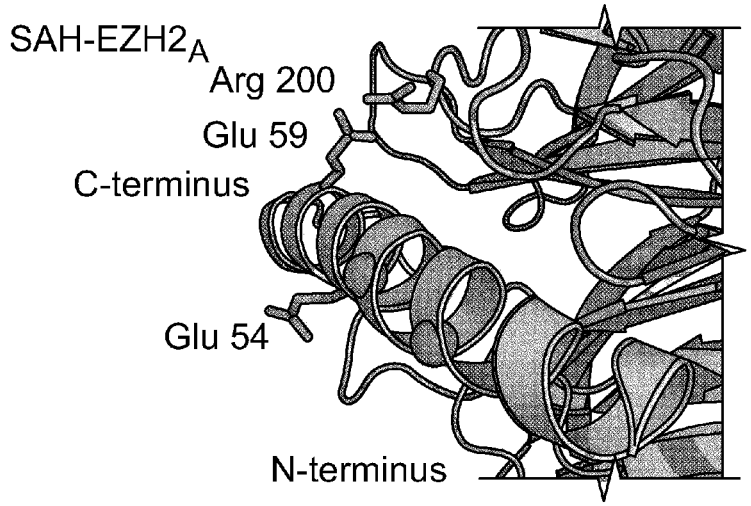
FIG. 2|The location of stapling position 'A' (47-51) is marked with red spheres and position 'C' (54-58) is marked with blue spheres. The alpha-helical EED-binding domain of EZH2 is colored gold and EED is colored gray. The native methionine of SAH-EZH2 was replaced with norleucine ('$N_L$') due to decreased efficiency of the metathesis reaction in the presence of sulfur. Insertion of single (i, i+3), (i, i+4), or (i, i+7) staples, and multiple staples in combinations thereof, are also envisioned. Sequences "A" are disclosed as SEQ ID NOS 3, 26 and 19, respectively, in order of appearance and Sequences "C" are disclosed as SEQ ID NOS 5, 33 and 20, respectively, in order of appearance.
Figure 2:
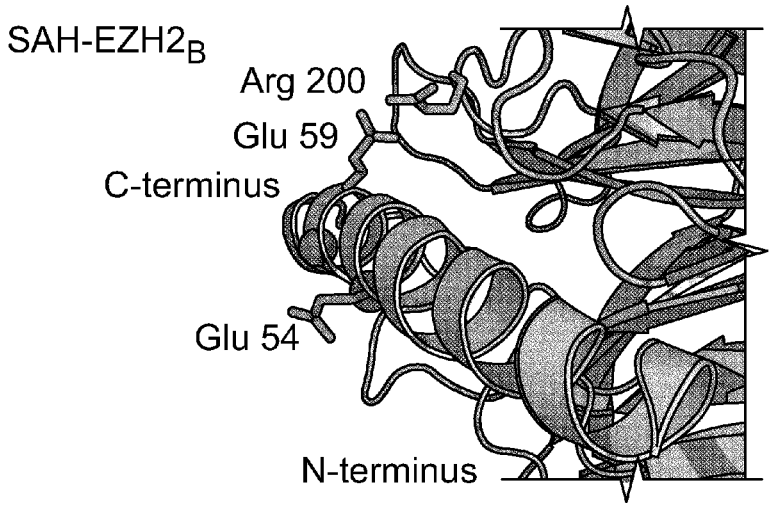
Figure 3:
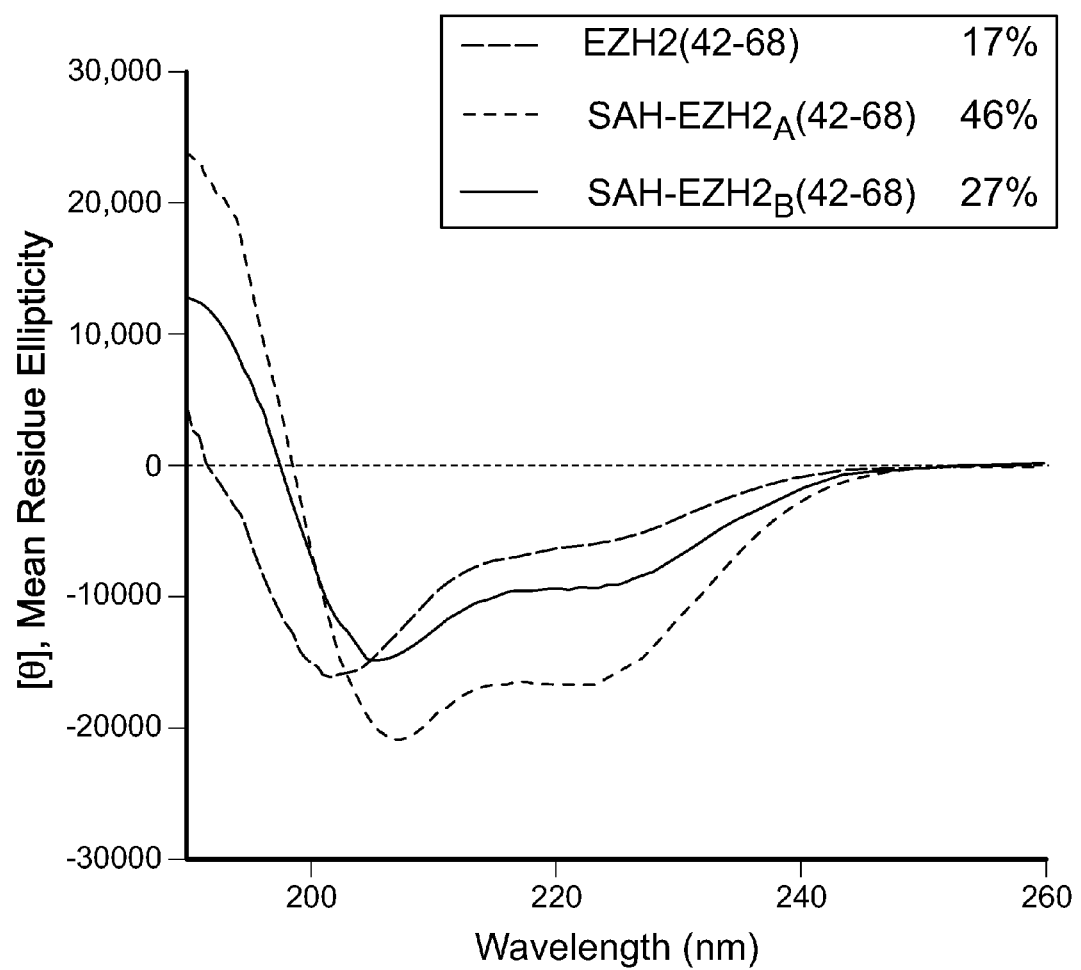
FIG. 3|Circular dichroism analysis of EZH2(42-68), SAH-EZH2$_A$(42-68) and SAH-EZH2$_C$(42-68) peptides, demonstrating structural stabilization by hydrocarbon stapling.
Figure 4:
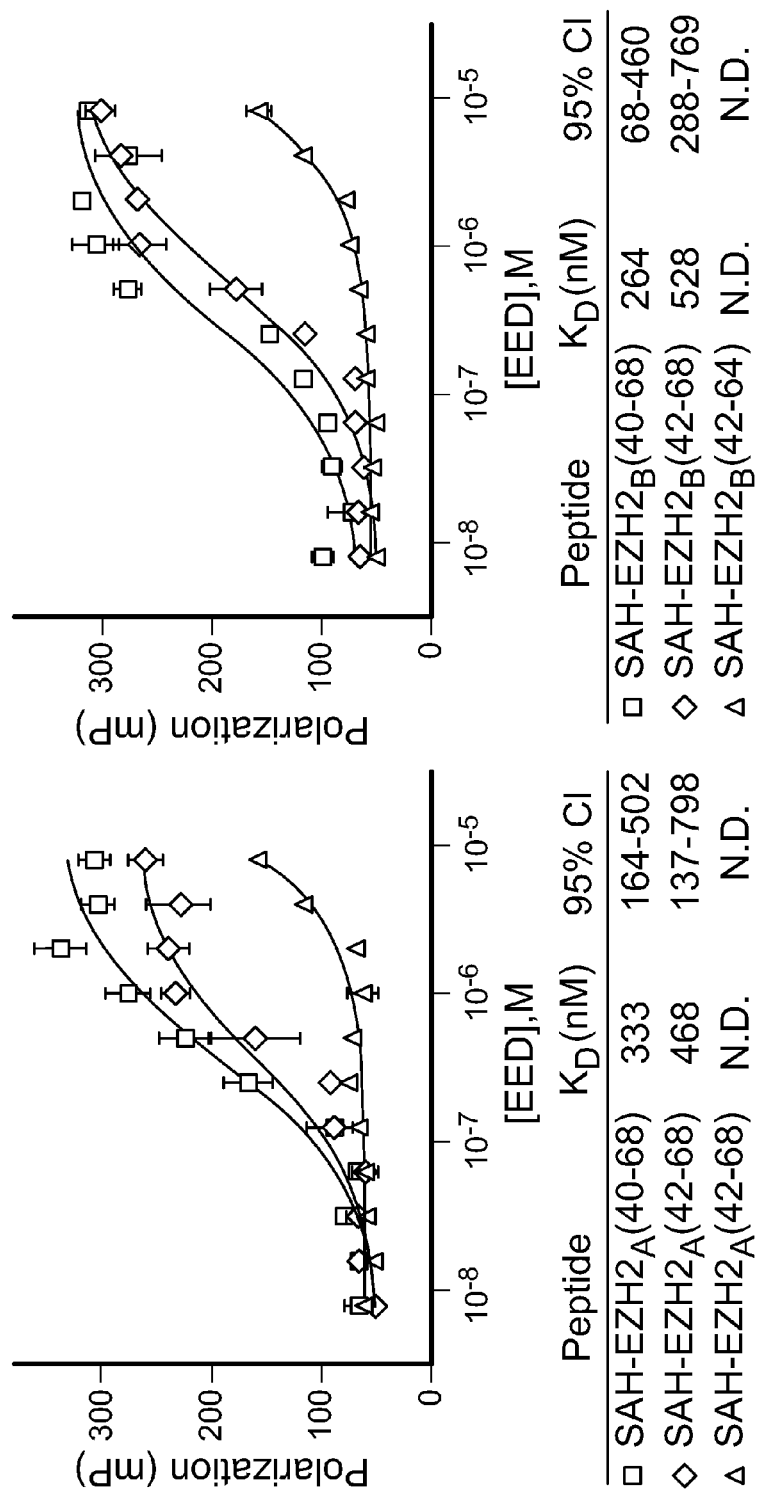
FIG. 4|Binding affinity of SAH-EZH2 peptides for EED as measured by fluorescence polarization. Data represents mean±s. e. m. for experiments performed in triplicate.
Figure 5:
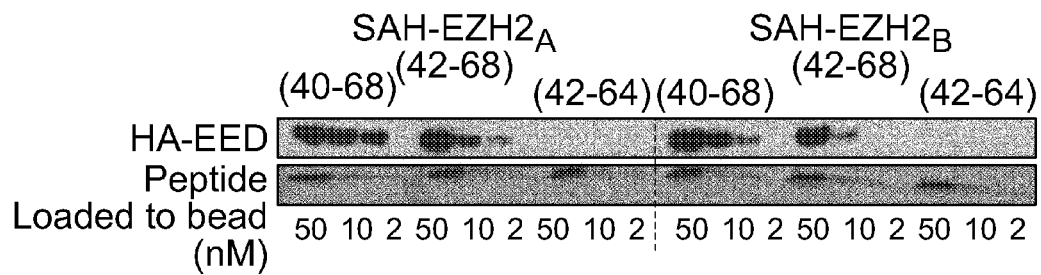
FIG. 5|Co-precipitation of purified HA-EED (40 nM final concentration) with FITC-labeled SAH-EZH2 peptides.

Hydrocarbon stapling has been applied to recapitulate the natural structure of alpha-helical binding motifs, yielding bioactive agents to dissect and target intracellular protein interactions[35-38]. To disrupt the PRC2 complex, we designed stapled peptides of variable length based on the alpha-helical, EED-binding domain of EZH2 that comprises amino acids 40-68[32] (FIG. 2). Two staple positions were sampled owing to their location at the opposite side of the key alpha-helical binding interface (FIG. 2), and insertion of the hydrocarbon staple enhanced alpha-helical structure, with the "A" staple conferring the most significant structural stabilization as assessed by circular dichroism (FIG. 3). The binding affinity of FITC-labeled SAH-EZH2 peptides for EED was measured by fluorescence polarization (FP) assay (FIG. 4) and co-immunoprecipitation (FIG. 5), documenting effective engagement of the EED target. However, significant differences emerged when comparing SAH-EZH2 peptides of different length. Whereas the longest constructs, SAH-EZH2$_A$(40-68) and SAH-EZH2$_B$(40-68) displayed the most potent dose-responsive EED-binding activities, followed by SAH-EZH2$_A$(42-68) and SAH-EZH2$_B$(42-68), the foreshortened SAH-EZH2$_A$(42-64) and SAH-EZH2$_B$(42-64) peptides lacking the IQPV motif exhibited no appreciable engagement of recombinant EED by FP or of expressed HA-EED by anti-FITC pull down (FIG. 5). These data are consistent with structure-function studies that documented the critical role of I65, P67 and V68 in the EZH2/EED interaction[32-34]. Thus, we identified SAH-EZH2 constructs comprising amino acids 40-68 and 42-68 as submicromolar EED binders.

Figure 6:
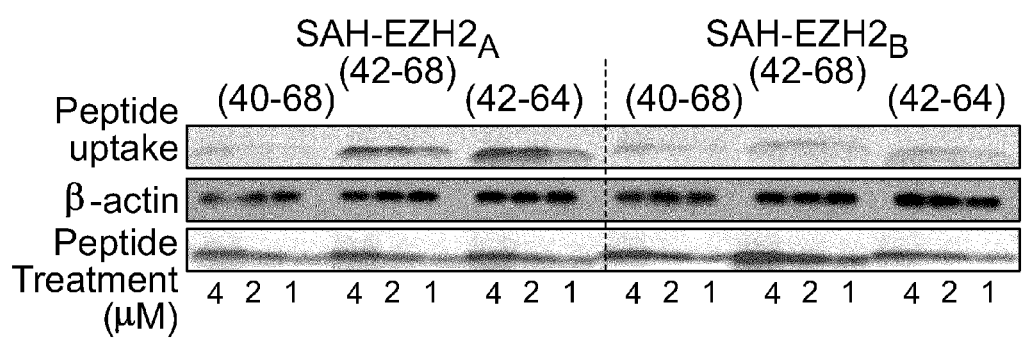
FIG. 6|Cellular penetrance of SAH-EZH2 peptides. Lysates of treated MLL-AF9 leukemia cells were electrophoresed and analyzed by fluorescence scan.

In preparation for phenotypic studies in treated cells, we evaluated the cellular uptake of SAH-EZH2 peptides in MLL-AF9 leukemia cells exposed to FITC-labeled derivatives, followed by fluorescence analysis of electrophoresed cellular extracts (FIG. 6). SAH-EZH2$_A$ peptides generally displayed enhanced cellular uptake in comparison with the corresponding constructs bearing the B-positioned staple, with the intermediate and shortest peptides exhibiting the most robust dose-responsive uptake. Based upon EED-binding potency and observed cellular penetrance, SAH-EZH2$_A$(42-68) emerged as the lead construct for optimization and biological testing.

SAH-EZH2 peptides were designed by replacing two naturally occurring amino acids with the non-natural S5 amino acids at i, i+4 positions (i.e. flanking 3 amino acids) to generate a staple spanning one α-helical turn, or a combination of R8 and S5 at i, i+7 positions, respectively, to generate a staple spanning two α-helical turns.

Asymmetric syntheses of α,α-disubstituted amino acids were performed as previously described in detail (Schafmeister et al., J. Am. Chem. Soc., 122:5891-5892, 2000; Walensky et al., Science, 305:1466-1470, 2004; Bird et al. Current Protocols in Chemical Biology, 2011).

Figure 1C:
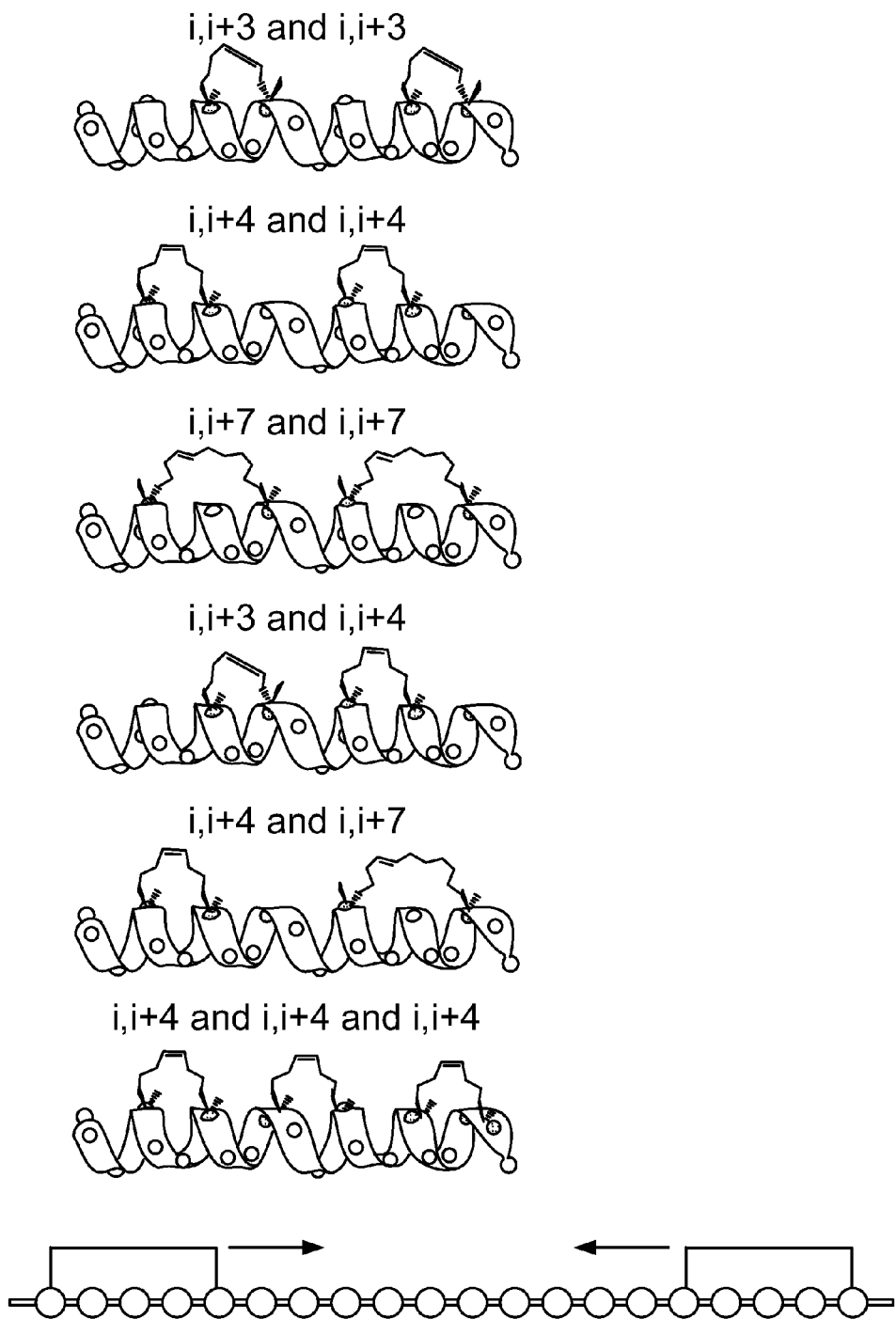
FIG. 1C|Examples of staple compositions for multiply stapled EZH2 peptides.
Figure 1D:
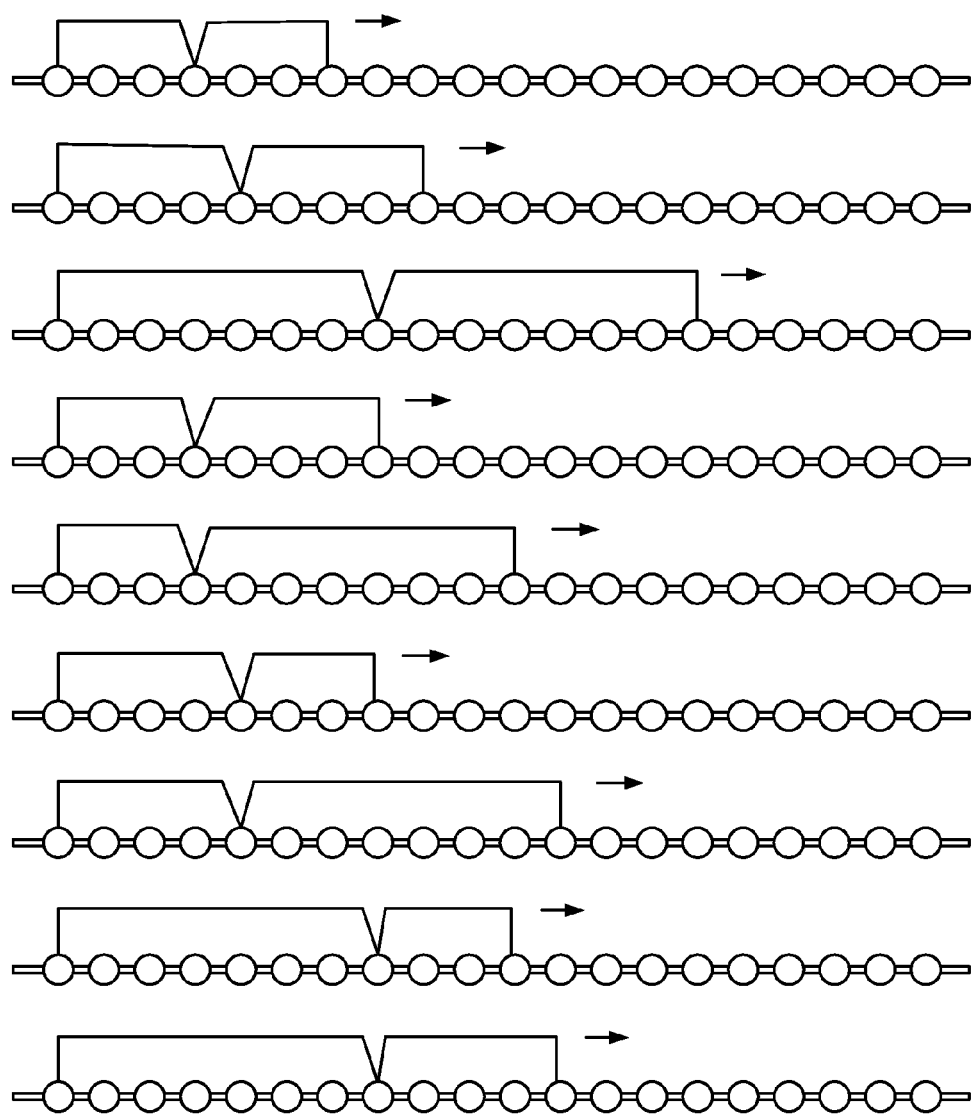
FIG. 1D|Examples of staple compositions for tandemly stapled stapled EZH2 peptides.

Alanine scanning and "staple scanning" was performed to respectively identify residues and binding surfaces critical for interaction, which dictates the design of optimized constructs and negative control mutants (see FIG. 1). The N-termini of SAHs are capped with acetyl or a fluorophore (e.g. FITC, rhodamine), depending upon the experimental application.

Doubly stapled peptides are generated by installing two-S5-S5, two—R8-S5, or other combinations of crosslinking non-natural amino acids (see FIG. 1). Multiply stapled or stitched peptides are generated using similar principles.

Synthesis of the SAH-EZH2 peptides shown in Table 2 was performed using solid phase Fmoc chemistry and ruthenium-catalyzed olefin metathesis, followed by peptide deprotection and cleavage, purification by reverse phase high performance liquid chromatography/mass spectrometry (LC/MS), and quantification by amino acid analysis (AAA) (Bird et al., Methods Enzymol., 446:369-386, 2008).

TABLE 2

| EZH2 Peptides (B = norleucine; J = Aib; X = stapling amino acid; sc = scrambled sequence) | |
|---|---|
| EZH2(40-68) | SMFSSNRQKILERTEILNQEWKQRRIQPV (SEQ ID NO: 2) |
| SAH-EZH2(40-68)$_A$ | SBFSSNRXKILXRTEILNQEWKQRRIQPV (SEQ ID NO: 3) |
| SAH-EZH2(40-68)$_B$ | SBFSSNRQKILXRTEXLNQEWKQRRIQPV (SEQ ID NO: 4) |
| SAH-EZH2(40-68)$_C$ | SBFSSNRQKILERTXILNXEWKQRRIQPV (SEQ ID NO: 5) |
| SAH-EZH2(40-68)$_D$ | SBFSSNRQKILERTEXLNQXWKQRRIQPV (SEQ ID NO: 6) |
| SAH-EZH2(40-68)$_E$ | SBFSSNRQKILERTEILNXEWKXRRIQPV (SEQ ID NO: 7) |
| EZH2(40-66)-sc | SBFSSNRQKILERTEILNQEBWQRRIQ (SEQ ID NO: 8) |
| SAH-EZH2(40-66)$_C$-sc | SBFSSNRQKILERTXILNXEBWQRRIQ (SEQ ID NO: 9) |
| SAH-EZH2(40-66)$_E$-sc | SBFSSNRQKILERTEILNXEBWXRRIQ (SEQ ID NO: 10) |
| EZH2(47-64) | QKILERTEILNQEWKQRR (SEQ ID NO: 11) |
| EZH2(47-64)-sc | QKILERTEILNQEBWQRR (SEQ ID NO: 12) |
| SAH-EZH2(47-64)$_C$-sc | QKILERTXILNXEBWQRR (SEQ ID NO: 13) |
| SAH-EZH2(47-64)$_E$-sc | QKILERTEILNXEBWXRR (SEQ ID NO: 14) |
| SAH-EZH2(45-64)$_A$ | NRXKILXRTEILNQEWKQRR (SEQ ID NO: 15) |
| SAH-EZH2(45-64)$_C$ | NRQKILERTXILNXEWKQRR (SEQ ID NO: 16) |
| SAH-EZH2(45-64)$_{A-MUT}$ | NRXKALXRTEIANQEAKQRR (SEQ ID NO: 17) |
| SAH-EZH2(45-64)$_{C-MUT}$ | NRQKALERTXIANXEAKQRR (SEQ ID NO: 18) |
| SAH-EZH2(42-64)$_A$ | FSSNRXKILXRTEILNQEWKQRR (SEQ ID NO: 19) |
| SAH-EZH2(42-64)$_C$ | FSSNRQKILERTXILNXEWKQRR (SEQ ID NO: 20) |
| SAH-EZH2(42-64)$_A$-541J/E54Q | FJSNRXKILXRTQILNQEWKQRR (SEQ ID NO: 21) |
| SAH-EZH2(42-64)$_A$-S42J/E54Q | FSJNRXKILXRTQILNQEWKQRR (SEQ ID NO: 22) |
| SAH-EZH2(42-64)$_C$-541J/E51Q | FJSNRQKILQRTXILNXEWKQRR (SEQ ID NO: 23) |
| SAH-EZH2(42-64)$_C$-541J/E51Q | FSJNRQKILQRTXILNXEWKQRR (SEQ ID NO: 24) |
| SAH-EZH2(42-64)$_C$-541J/E51Q-$_{MUT}$ | FJSNRQKALQRTXIANXEAKQRR (SEQ ID NO: 25) |
| SAH-EZH2(42-68)$_A$ | FSSNRXKILXRTEILNQEWKQRRIQPV (SEQ ID NO: 26) |
| SAH-EZH2(42-68)$_A$-E54Q | FSSNRXKILXRTQILNQEWKQRRIQPV (SEQ ID NO: 27) |
| SAH-EZH2(42-68)$_A$-E54,59Q | FSSNRXKILXRTQILNQQWKQRRIQPV (SEQ ID NO: 28) |
| SAH-EZH2(42-68)$_A$-K48QE54QE59K | FSSNRXQILXRTQILNQKWKQRRIQPV (SEQ ID NO: 29) |
| SAH-EZH2(42-68)$_B$ | FSSNRQKILXRTEXLNQEWKQRRIQPV (SEQ ID NO: 30) |
| SAH-EZH2(42-68)$_B$-E54Q | FSSNRQKILXRTQXLNQEWKQRRIQPV (SEQ ID NO: 31) |
| SAH-EZH2(42-68)$_B$-E54,59Q | FSSNRQKILXRTQXLNQQWKQRRIQPV (SEQ ID NO: 32) |
| SAH-EZH2(42-68)$_C$ | FSSNRQKILERTXILNXEWKQRRIQPV (SEQ ID NO: 33) |
| SAH-EZH2(42-68)$_D$-E51Q | FSSNRQKILQRTXILNXEWKQRRIQPV (SEQ ID NO: 34) |
| SAH-EZH2(42-68)$_C$-E51,59Q | FSSNRQKILQRTXILNXQWKQRRIQPV (SEQ ID NO: 35) |
| SAH-EZH2(42-68)$_D$ | FSSNRQKILERTEXLNQXWKQRRIQPV (SEQ ID NO: 36) |

TABLE 2-continued

EZH2 Peptides
(B = norleucine; J = Aib; X = stapling amino acid; sc = scrambled sequence)

| Name | Sequence | |
|---|---|---|
| SAH-EZH2(42-68)$_D$-E51Q | FSSNRQKILQRTEXLNQXWKQRRIQPV | (SEQ ID NO: 37) |
| SAH-EZH2(42-68)$_D$-E54Q | FSSNRQKILERTQXLNQXWKQRRIQPV | (SEQ ID NO: 38) |
| SAH-EZH2(42-68)$_D$-E51,54Q | FSSNRQKILQRTQXLNQXWKQRRIQPV | (SEQ ID NO: 39) |
| EZH2(42-68) | FSSNRQKILERTEILNQEWKQRRIQPV | (SEQ ID NO: 40) |
| EZH2(42-68) E54Q | FSSNRQKILERTQILNQEWKQRRIQPV | (SEQ ID NO: 41) |

Example 2

Figure 7:
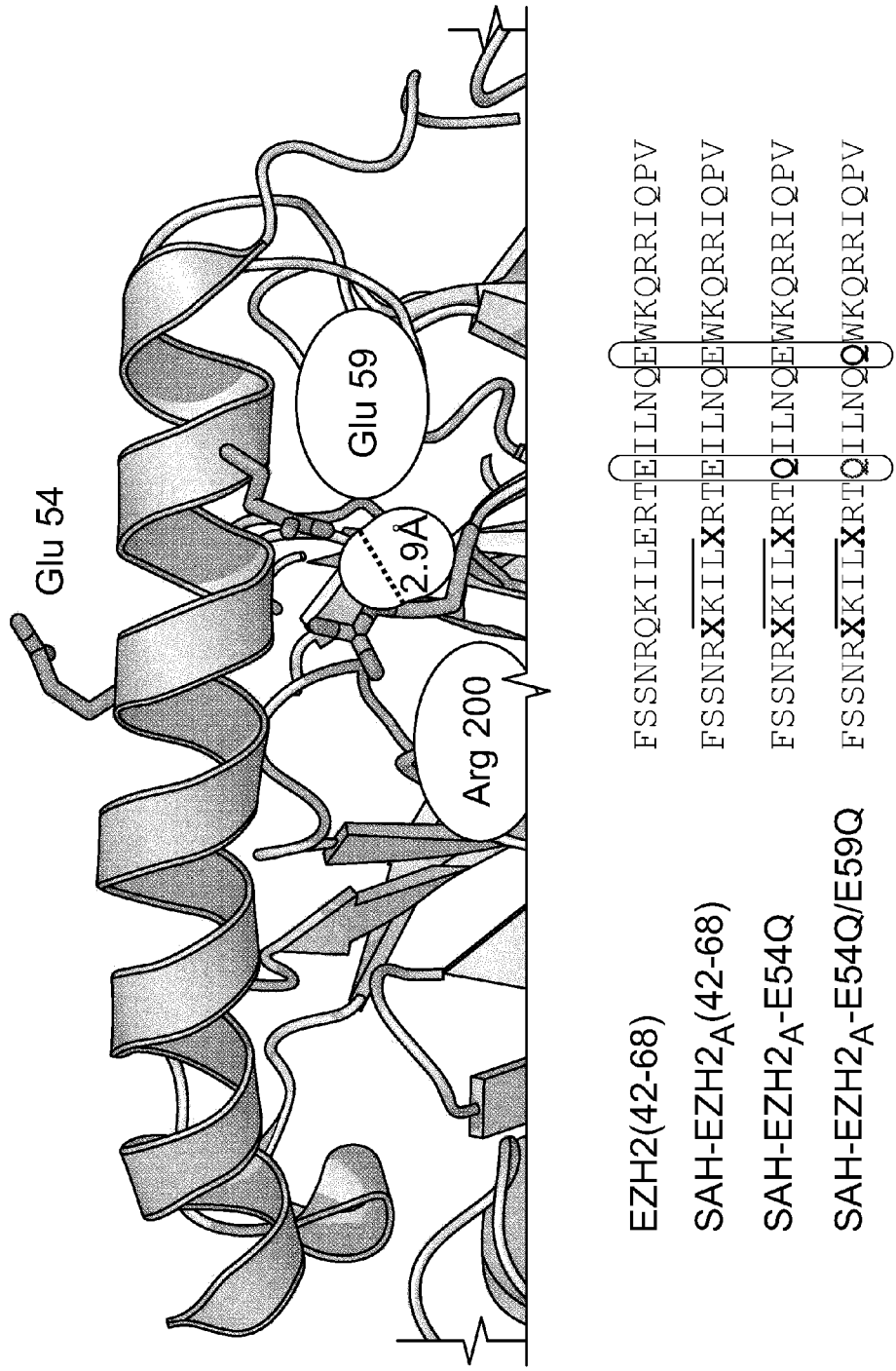
FIG. 7|Design of an optimized SAH-EZH2 peptide (SAH-EZH2$_A$[42-68]E54Q) and a negative control derivative (SAH-EZH2$_A$ [42-68]E54Q/E59Q) by glutamate mutagenesis. Sequences are disclosed as SEQ ID NOS 40 and 26-28, respectively, in order of appearance.
Figure 11:
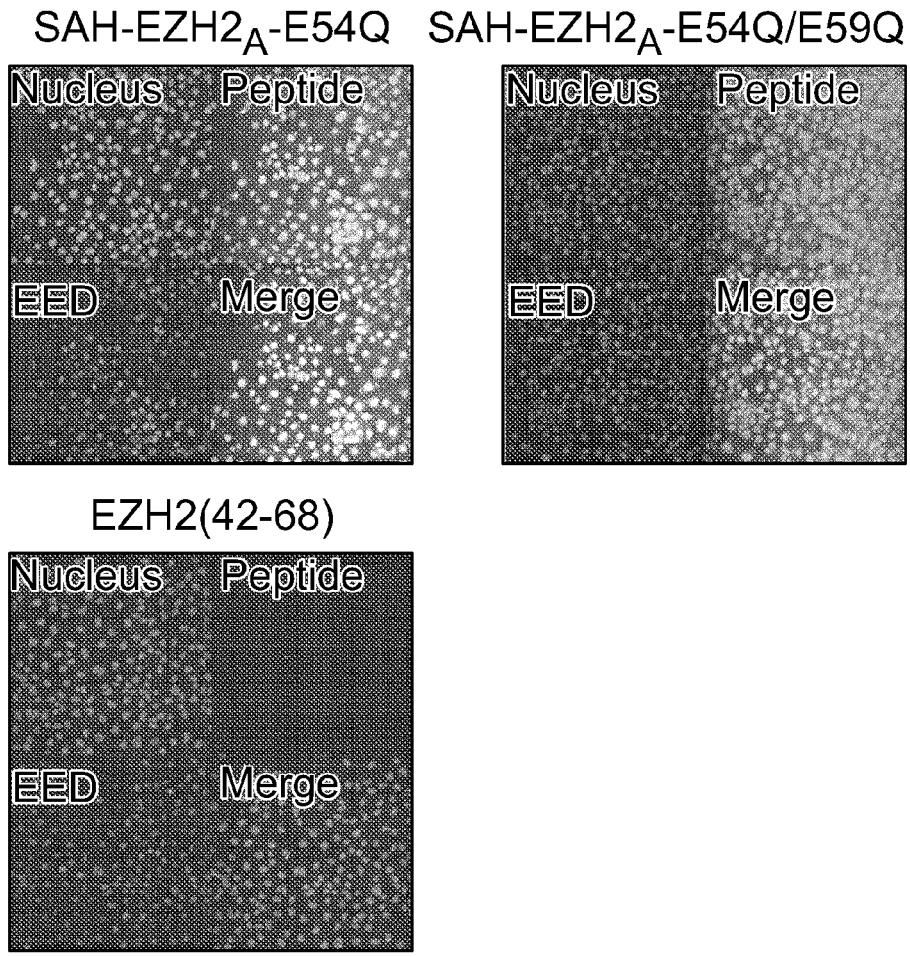
FIG. 11|Localization of EED (red) and SAH-EZH2$_A$ (42-68) E54Q and E54Q/E59Q peptides (green) to the nuclei (DAPI, blue) of COS-7 cells. Whereas the FITC-labeled stapled peptides demonstrate robust cellular uptake, the corresponding unmodified peptide shows no cellular penetrance.
Figure 12:
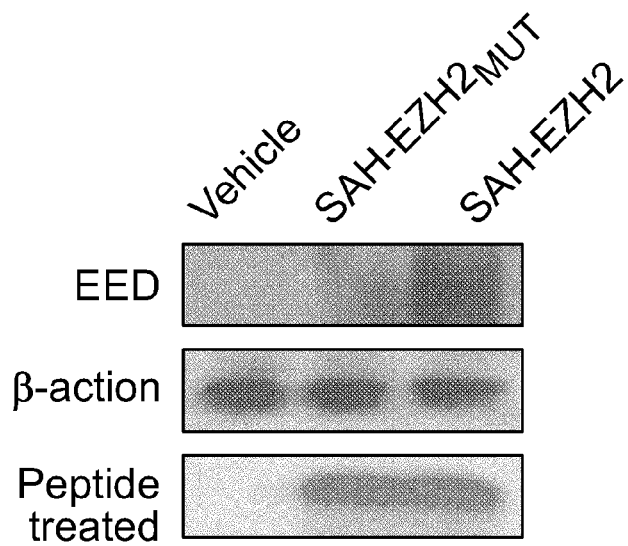
FIG. 12|Binding of SAH-EZH2$_A$ (42-68)E54Q (designated SAH-EZH2), but not SAH-EZH2$_A$ (42-68)E54Q/E59Q (designated SAH-EZH2$_{MUT}$), to native EED, as assessed by anti-FITC immunoprecipitation from peptide-treated MLL-AF9 cell culture and EED western analysis.
Figure 13A:
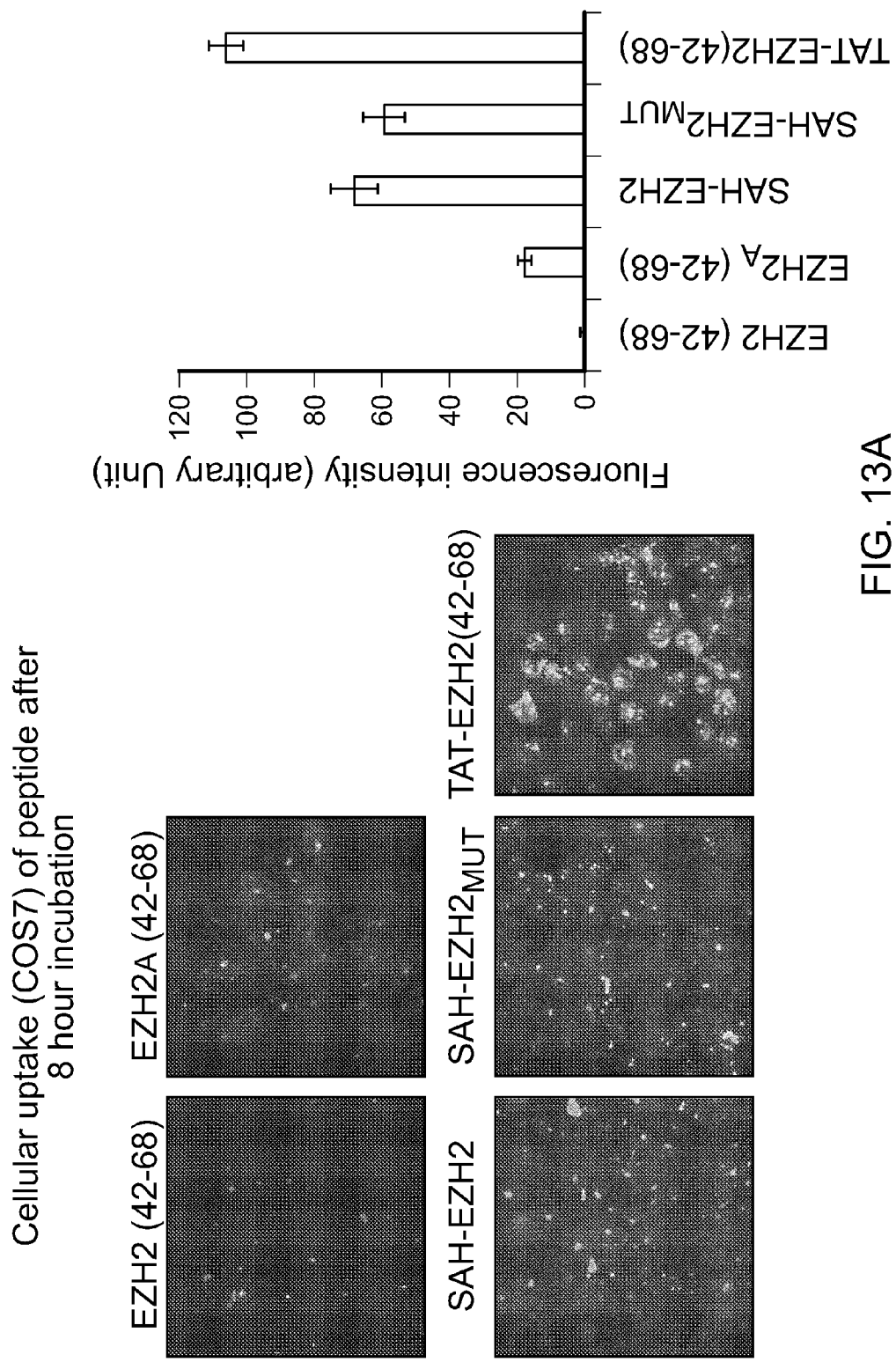
FIG. 13|Cellular uptake and intracellular stability of SAH-EZH2$_A$ peptides. (a) SAH-EZH2$_A$ peptides manifest a markedly increased propensity for cellular uptake compared to the corresponding unmodified peptide, with E54Q and E54Q/E59Q mutagenesis further enhancing uptake as reflected by the increased cellular fluorescence. Appending the cell penetrating sequence TAT to the unmodified EZH2 peptide likewise enhances peptide uptake, as measured by cellular fluorescence at 8 hours. (b) Analysis of cellular lysates by electrophoresis and fluorescence scan over time reveals that SAH-EZH2 peptides (SEQ ID NOS 40, 26-28 and 54, respectively, in order of appearance) persist at high levels in the cell, whereas intact TAT-EZH2 is not detected by the 2 hour timepoint. These data indicate that SAH-EZH2 peptides achieve rapid cellular uptake and remain fully intact. Thus, in contrast to SAH-EZH2 peptides, the TAT-EZH2 signal observed by fluorescence at 8 hours (a) reflects the presence of FITC, but not the fully intact peptide.
Figure 13B:
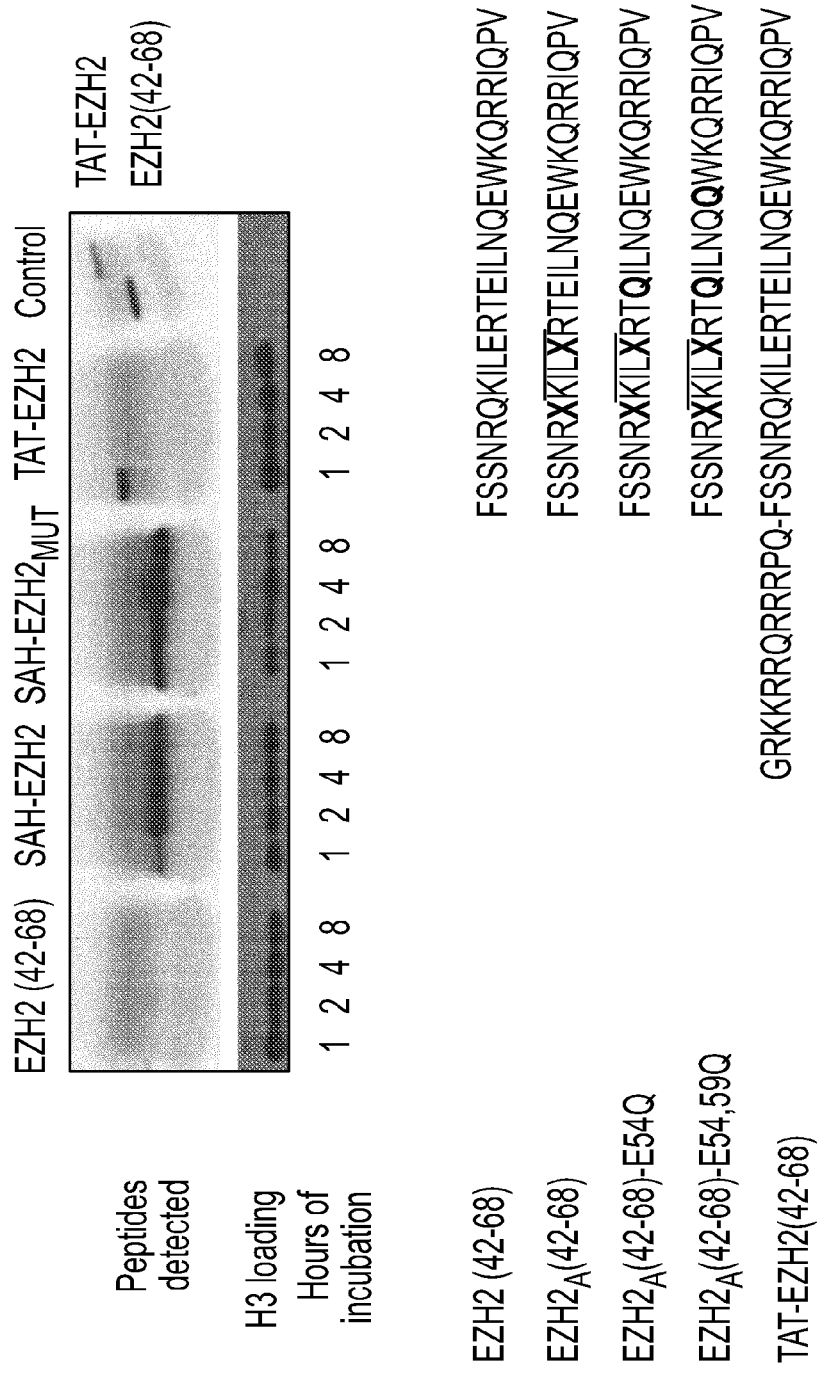

Targeted Disruption of the EZH2/EED Complex and Suppression of H3K27 Methylation We previously observed that neutralization of negatively charged residues, such as Asp and Glu, can enhance the permeability of stapled peptides[35-38,38,39]. Sequence comparison of EZH2 homologs indicates that Glu54 is not conserved, suggesting that this residue is dispensable for binding to EED[32,32]. Therefore, we mutated the non-interacting Glu54 residue of SAH-EZH2$_A$(42-68) to Gln (FIG. 7) and indeed observed further enhancement of cellular uptake (FIG. 8) without compromising in vitro binding activity (FIG. 9, 10). To generate a negative control peptide for cellular studies, we further mutated Glu59—a highly conserved residue among EZH2 homologs—to Gln in an effort to disrupt the salt bridge between Arg200 of EED and Glu59 of EZH2 at the binding interface (FIG. 7)[32,32]. We found this doubly mutant construct to manifest similar cellular penetrance (FIG. 8) but markedly reduced in vitro EED binding activity, as assessed by fluorescence polarization assay (FIG. 9) and FITC-SAH pull down of HA-EED (FIG. 10). Consistent with these data, confocal microscopy analyses documented robust cellular uptake and nuclear localization of both SAH-EZH2$_A$(42-68)E54Q and SAH-EZH2$_A$(42-68) E54Q/E59Q (hereafter referred to as SAH-EZH2 and SAH-EZH2$_{MUT}$, respectively) (FIG. 11), but only SAH-EZH2 effectively co-precipitated native EED from MLL-AF9 cells treated with the corresponding FITC-labeled peptides (FIG. 12). Whereas SAH-EZH2 peptides manifested marked cellular uptake compared to the corresponding unmodified peptides, appending a cell penetrating TAT moiety to the unmodified peptide (42-68) conferred uptake (FIG. 13a). However, time course analysis of intracellular full-length peptide by electrophoresis of lysates and fluorescence scan detection, documented that the SAH-EZH2 peptides persisted in full-length form over time, whereas the TAT-EZH2 peptide was undetectable by 2 hours (FIG. 13b). These data highlight that hydrocarbon stapling of the EZH2 peptide sequence not only confers robust cellular uptake but enables intracellular persistence of the peptide in full-length form (FIG. 13).

Figure 14:
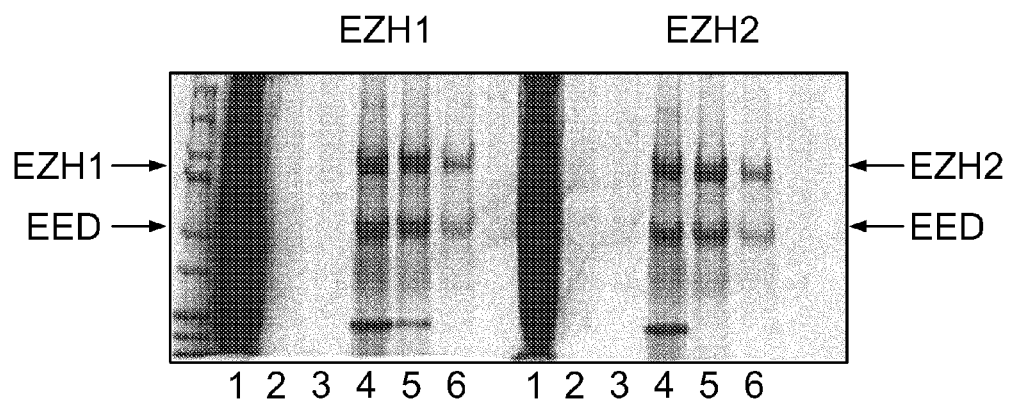
FIG. 14|Co-immunoprecipitation of HA-EED with FLAG-EZH1/FLAG-EZH2 by anti-FLAG agarose (coomassie blue staining). HA-EED was confirmed by HA-antibody western analysis (data not shown).
Figure 15:
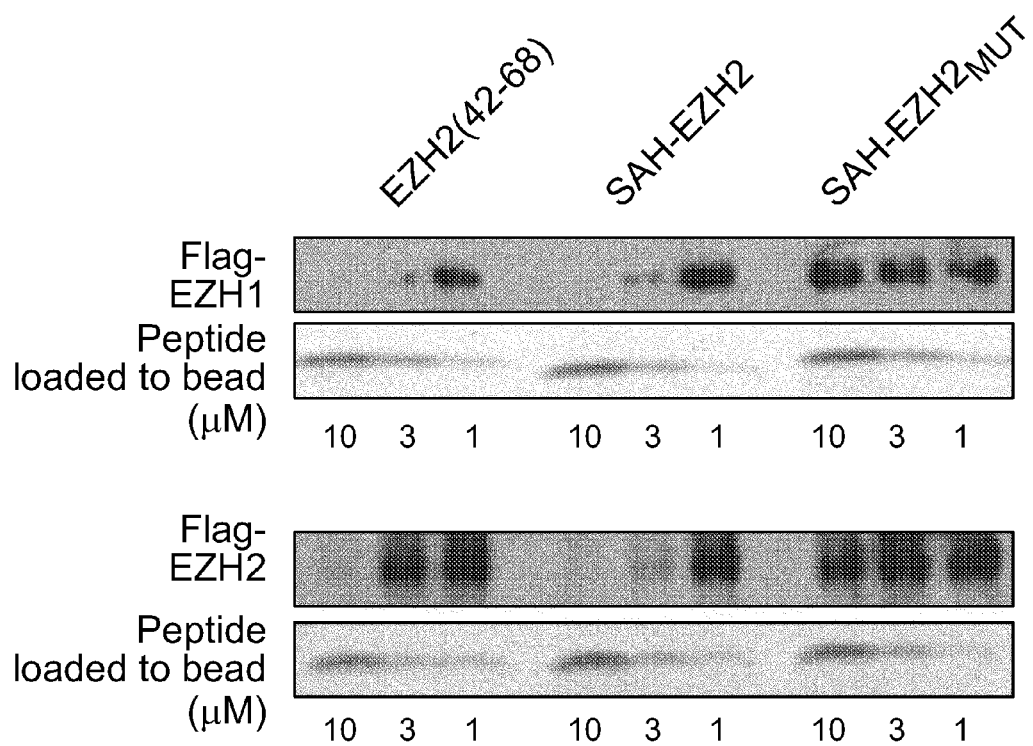
FIG. 15|Dissociation of HA-EED/EZH1 and HA-EED/EZH2 complexes (40 nM final concentration) by SAH- EZH2, but not SAH-EZH2$_{MUT}$ as assessed by anti-HA pull-down and EZH1/EZH2 western analysis.
Figure 16:
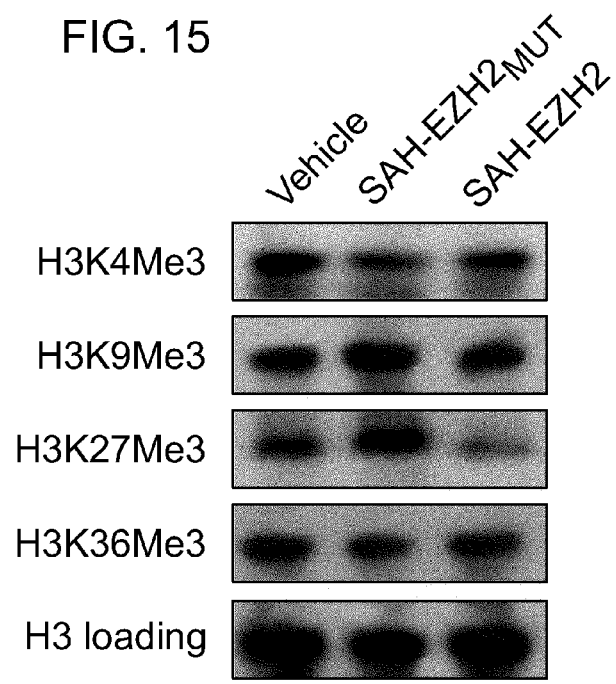
FIG. 16|Selective reduction of H3K27Me3 by SAH-EZH2, as assessed by trimethylation mark western analysis. MLL-AF9 leukemia cells were treated with SAH-EZH2 or SAH-EZH2$_{MUT}$ (10 μM final concentration) twice daily for 7 days before analysis.
Figure 17:
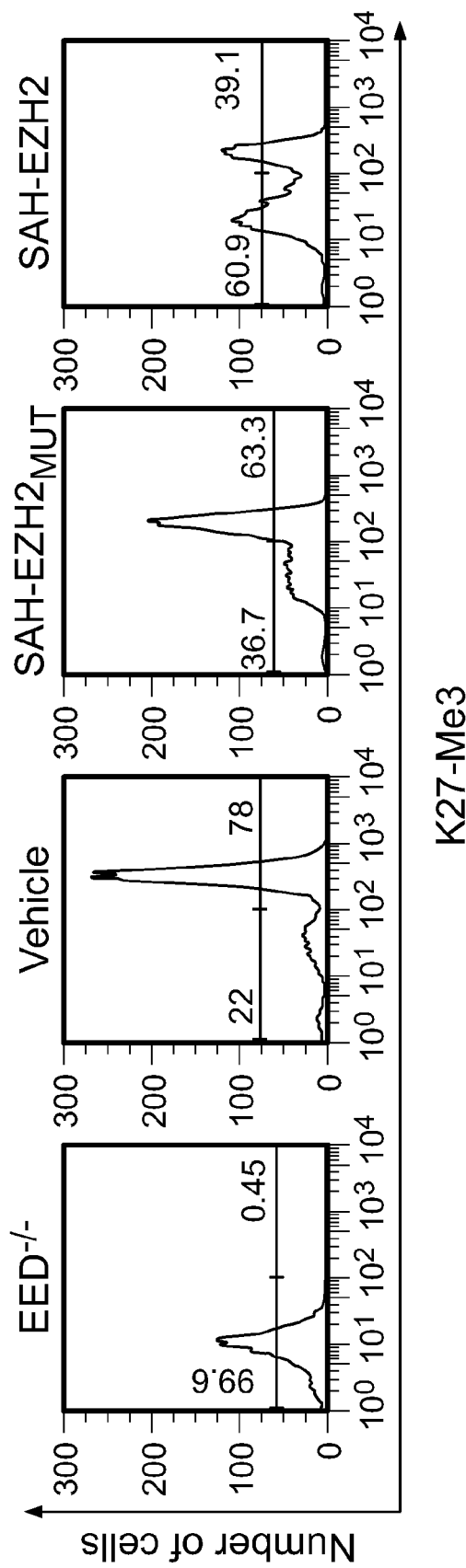
FIG. 17|Flow cytometric analysis of SAH-EZH2-treated MLL-AF9 leukemia cells. SAH-EZH2 decreased the number of cells manifesting H3Lys27 trimethylation.
Figure 18:
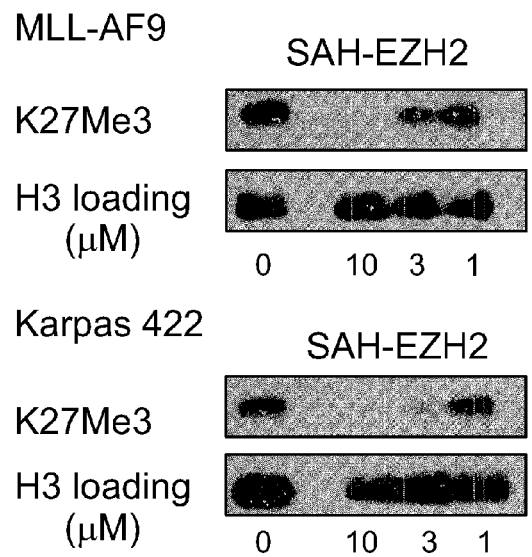
FIG. 18|SAH-EZH2 dose-responsively decreases H3K27Me3 levels in MLL-AF9 leukemia and Karpas422 lymphoma cells, as measured after 8 days of treatment.

Since the catalytic activity of PRC2 depends on the interaction between EZH2 and EED, we explored the capacity of SAH-EZH2 to disrupt EED engagement with EZH2, and its homolog EZH1 (FIG. 14, 15). Of note, EZH1 shares 86% amino acid identity with the EED-binding domain of EZH2, and is believed to form an alternate, catalytically active PRC2 complex with EED and Suz12[38-42]. In Ezh2$^{-/-}$ murine embryonic stem cells, EZH1 partially compensates for loss of EZH2 and maintains trimethylation of a subset of developmental genes[32,40]. Indeed, HA-EED co-immunoprecipitated Flag-EZH1 and Flag-EZH2 upon co-expression in sf21 cells (FIG. 14). When SAH-EZH2 peptides were incubated with these purified EZH1/EED and EZH2/EED complexes, dose-responsive dissociation of the protein interactions was observed for SAH-EZH2 but, importantly, not for the mutant control (FIG. 15). To determine if the capacity of SAH-EZH2 to target and dissociate these complexes functionally impaired PRC2 methyltransferase activity, MLL-AF9 cells were treated with SAH-EZH2 and histone modification was followed by western blot and flow cytometry (FIG. 16, FIG. 17). Of note, an extended treatment course (7 days) was employed owing to the prolonged half-life of the trimethyl mark.[32,43,44] Both experimental read-outs documented that SAH-EZH2 treatment decreased trimethylation of H3K27 (FIG. 16, FIG. 17). The selectivity of SAH-EZH2 activity was highlighted by the inactivity of SAH-EZH2$_{MUT}$ and the lack of a SAH-EZH2 effect on the H3K4, H3K9 and H3K36 methyl marks (FIG. 16). Importantly, inhibition of H3K27 methylation in both MLL-AF9 and Karpas422 cells was dose-responsive (FIG. 18). Thus, SAH-EZH2 targets native EED, dissociates its interactions with EZH1 and EZH2, and selectively decreases the trimethylation of H3K27.

Example 3

SAH-EZH2 Arrests Proliferation of MLL-AF9 Leukemia Cells

Figure 19:
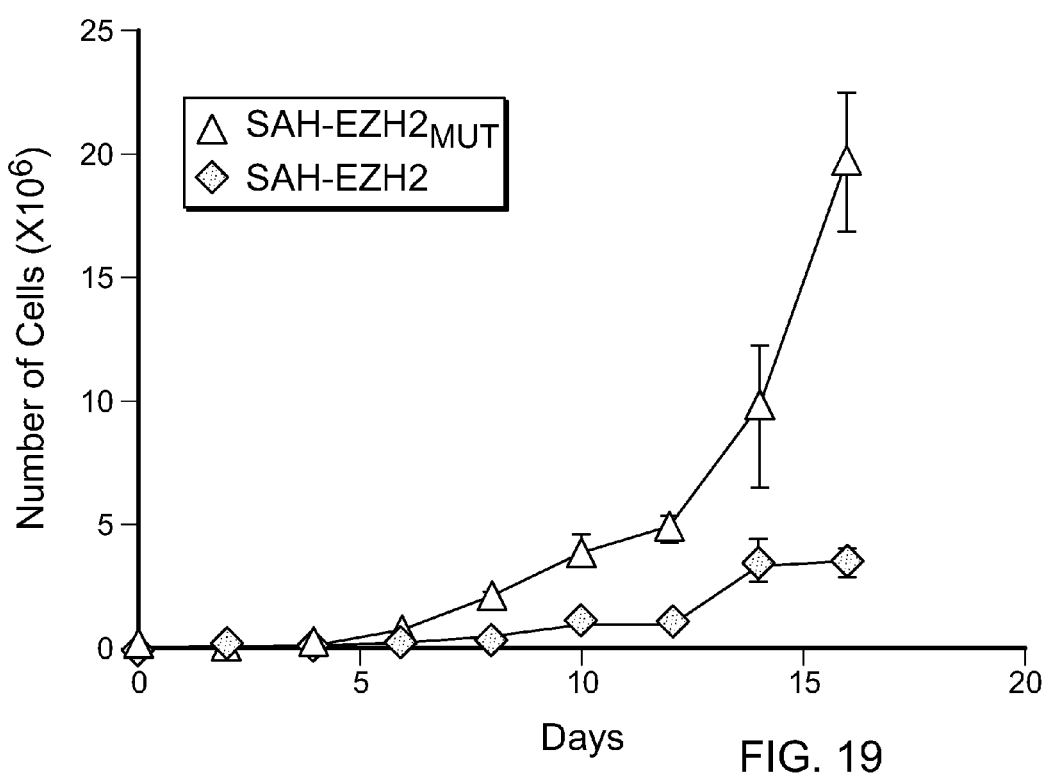
FIG. 19|SAH-EZH2, but not its mutant control, inhibits the proliferation of MLL-AF9 cells. Data represent mean and s.e.m for experiments performed in triplicate. MLL-AF9 leukemia cells were treated with 10 μM final concentration of SAH-EZH2 or SAH-EZH2$_{MUT}$ twice daily; water was used as vehicle.
Figure 20:
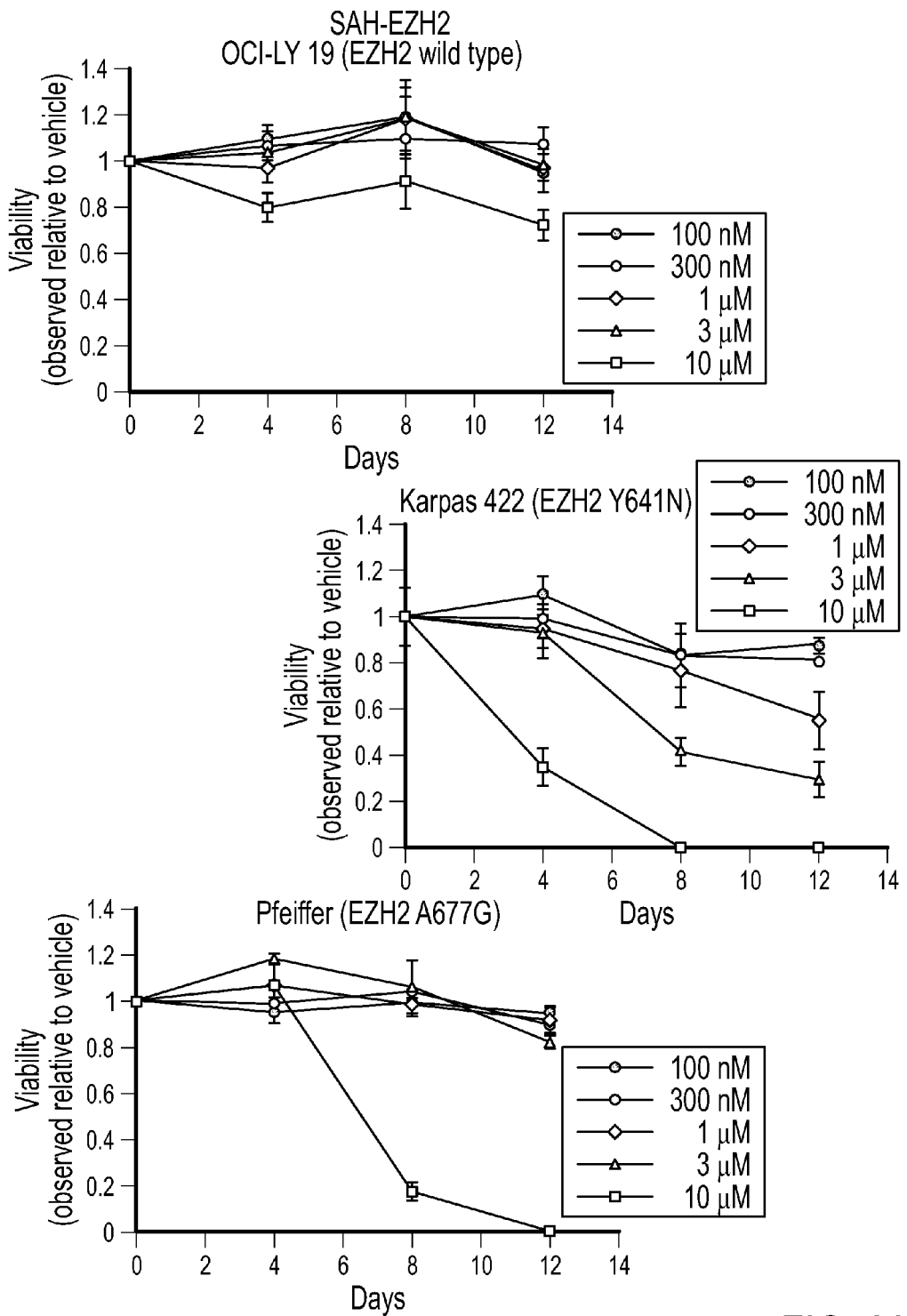
FIG. 20|Anti-proliferative effects of SAH-EZH2 on B cell lymphoma cell lines with wild-type or the indicated mutant versions of EZH2 protein.
Figure 21:
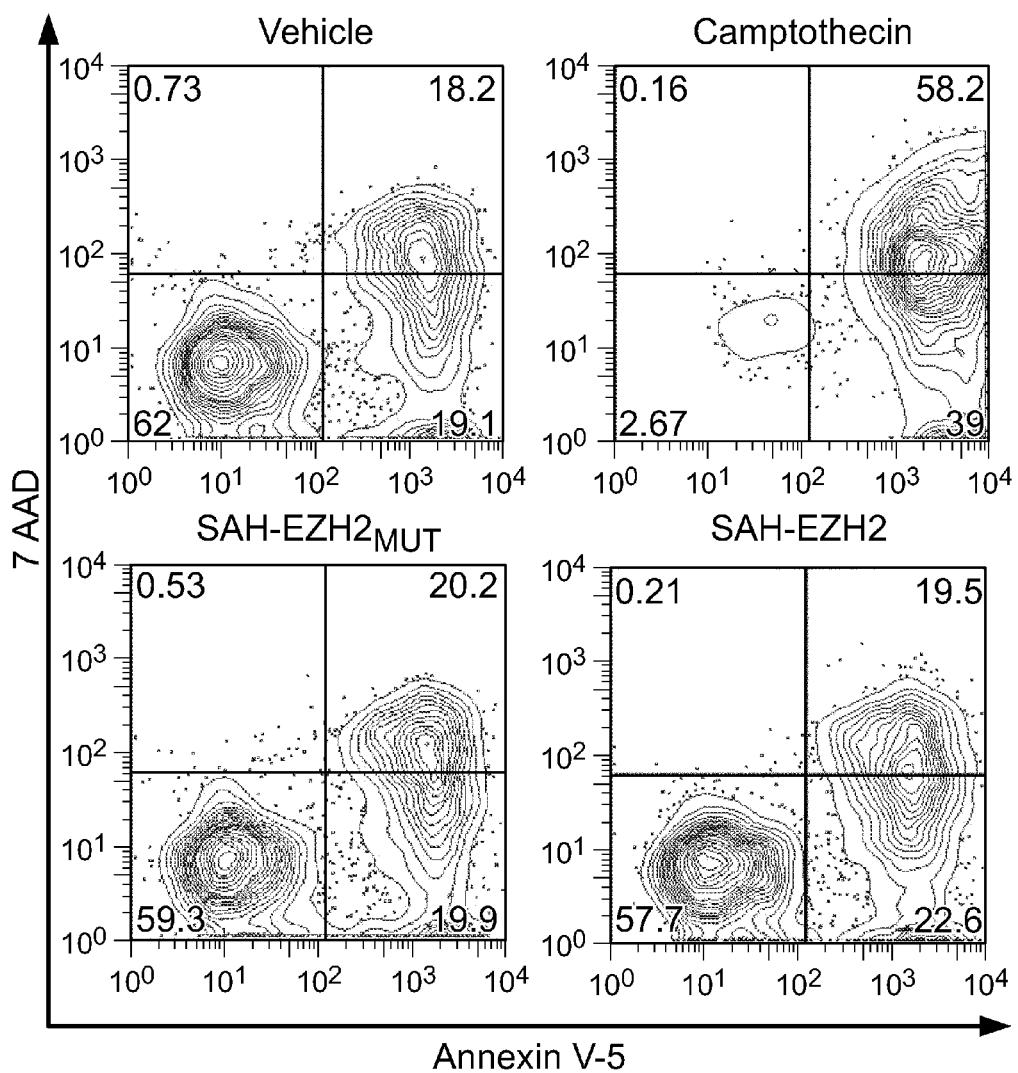
FIG. 21|The anti-leukemic activity of SAH-EZH2 is not mediated by a pro-apoptotic effect, as assessed by FACS analysis and 7AAD/Annexin V staining after 8 days of treatment with SAH-EZH2 peptides. MLL-AF9 leukemia cells were treated with 10 μM final concentration of SAH-EZH2 or SAH-EZH2$_{MUT}$ twice daily; water was used as vehicle.
Figure 22:
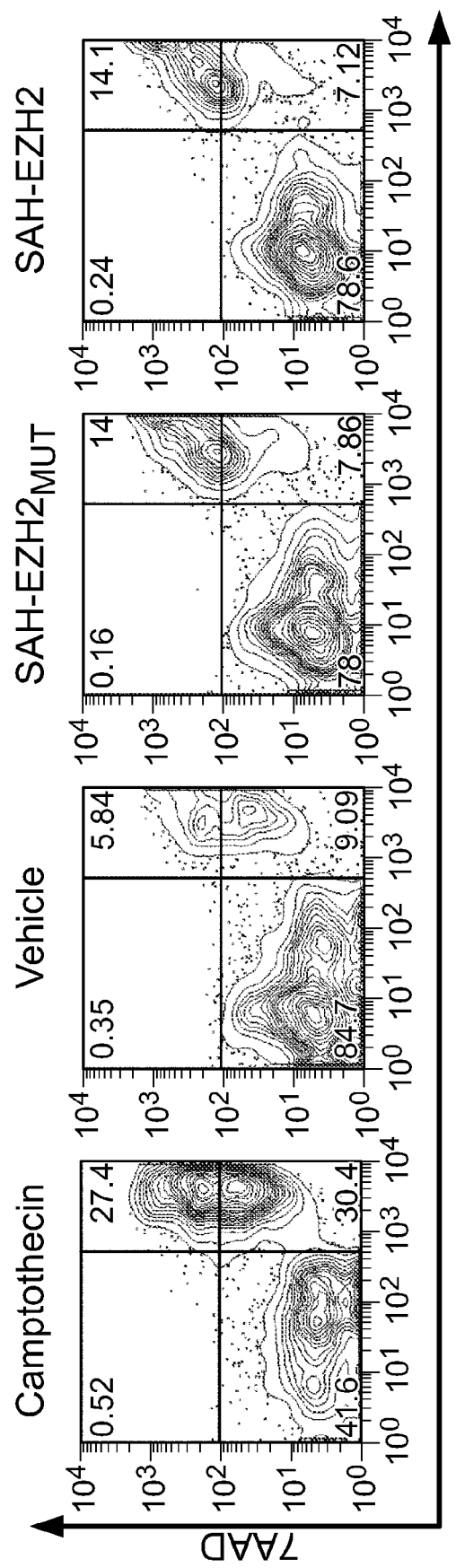
FIG. 22|Apoptosis analysis of MLL-AF9 cells after extended incubation with SAH-EZH2 peptides (16 days)
Figure 23:
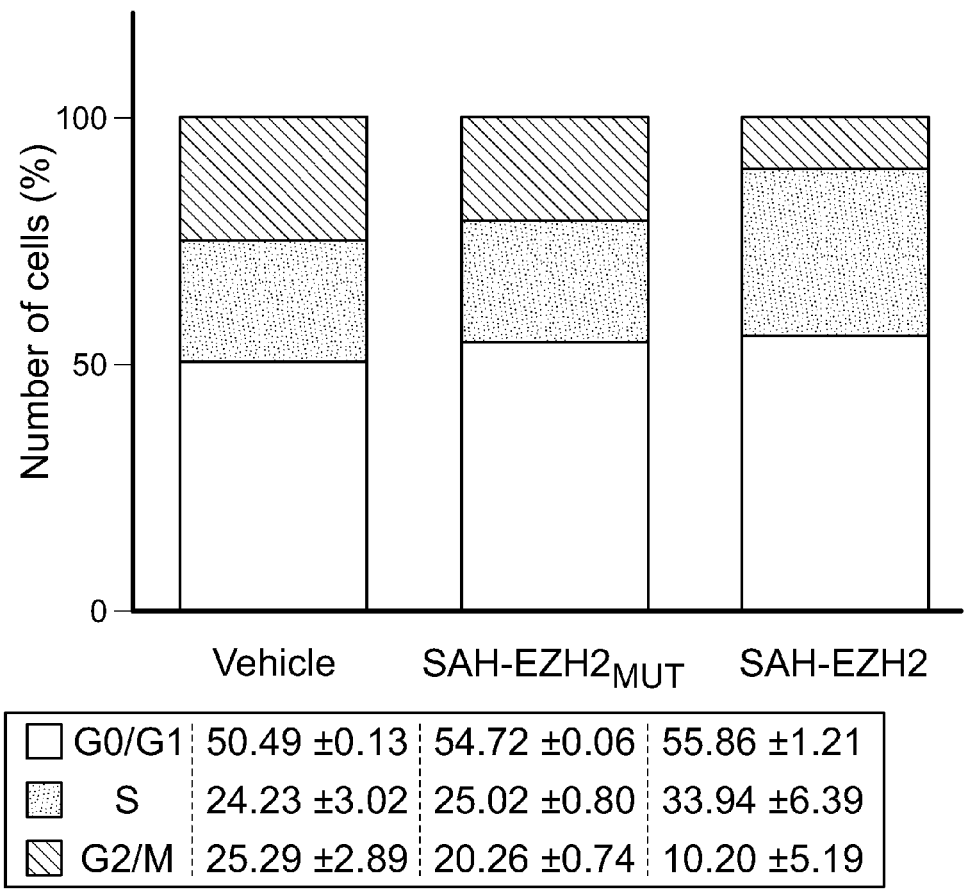
FIG. 23|Cell cycle analysis of SAH-EZH2-treated cells. Cells were stained with PI and analyzed by flow cytometry after 8 days of treatment. Data was analyzed using ModFIT software and represents mean±s.d. for experiments performed in duplicate. MLL-AF9 leukemia cells were treated with 10 μM final concentration of SAH-EZH2 or SAH-EZH2$_{MUT}$ twice daily; water was used as vehicle.
Figure 24:
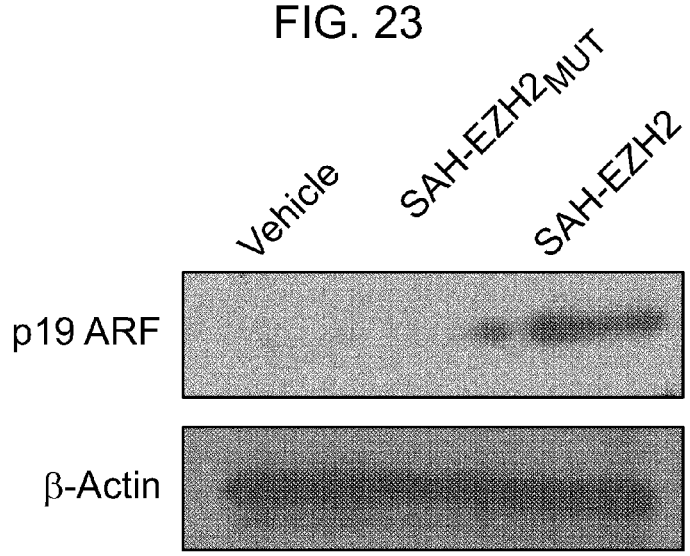
FIG. 24|SAH-EZH2, but not its mutant control, upregulates the expression of p19ARF upon treatment of MLL-AF9 cells (7 days), as assessed by western analysis. MLL-AF9 leukemia cells were treated with 10 μM final concentration of SAH-EZH2 or SAH-EZH2$_{MUT}$ twice daily; water was used as vehicle.

Since MLL-AF9 cells are dependent on EZH2 and the PRC2 complex for growth[33,34,40-42], we explored whether the biochemical activity of SAH-EZH2 translated into an anti-leukemic effect. We treated MLL-AF9 cells for an extended incubation period and noted significantly slowed growth by eight days for SAH-EZH2-but not mutant control-exposed cells (FIG. 19). These data are consistent with prior studies in which knockdown or knockout of EZH2 or EED impaired proliferation of MLL-AF9 cells[33,3440]. SAH-EZH2 also had a selective impact on the viability of mutant EZH2-driven B cell lymphoma cells bearing activating mutations Y641N or A677G, but not an EZH2-independent lymphoma cell bearing wild-type EZH2, further highlighting the mechanistic specificity of SAH-EZH2 activity (FIG. 20). To investigate whether the decreased growth rate of MLL-AF9 cells was associated with increased apoptosis, we stained cells with Annexin V5-PE and 7-AAD after 2, 4 and 8 day incubations with SAH-EZH2 or its mutant control peptide, followed by flow cytometric analysis. Little to no increase in apoptotic cells was observed upon treatment with SAH-EZH2 peptides for 8 (FIG. 21) or even 16 days (FIG. 22), whereas exposure to the chemotherapeutic agent, camptothecin, triggered a robust apoptotic effect. Given the lack of an apoptotic effect, we investigated whether the observed decreased growth of MLL-AF9 cells upon exposure to SAH-EZH2 was associated with modulation of the cell cycle. Whereas propidium iodide staining and flow cytometric analysis of SAH-EZH2-treated MLL-AF9 cells showed no cell cycle effects at day 4 of treatment (data not shown), by day 8, an increased percentage of cells in S phases and a corresponding decrease in G2/M was observed (FIG. 23). Compared to cells treated with the mutant control stapled peptide, SAH-EZH2 induced an increase of cells in S phase from 25.02% to 33.94%, and a decrease in G2/M phase from 20.26% to 10.20%. These data suggest that the effect of SAH-EZH2 on MLL-AF9 cell proliferation results from reduction of the fraction of cells in the G2/M phase. Interestingly, knockdown or genetic ablation of Ezh2 was previously reported to derepress the cell cycle inhibitory Ink4A/Arf locus[16,43-45]. Consistent with this finding, SAH-EZH2 treatment of MLL-AF9 cells increased p19ARF levels whereas cells treated with SAH-EZH2$_{MUT}$ or no peptide showed little to no p19ARF expression (FIG. 24). Taken together, these data indicate that the observed proliferative arrest of cells treated with SAH-EZH2 derives from a cell cycle blockade that coincides with increased expression of p19ARF.

Example 4

SAH-EZH2 Induces Monocytic/Macrophage Differentiation of MLL-AF9 Leukemia Cells

Figure 25:
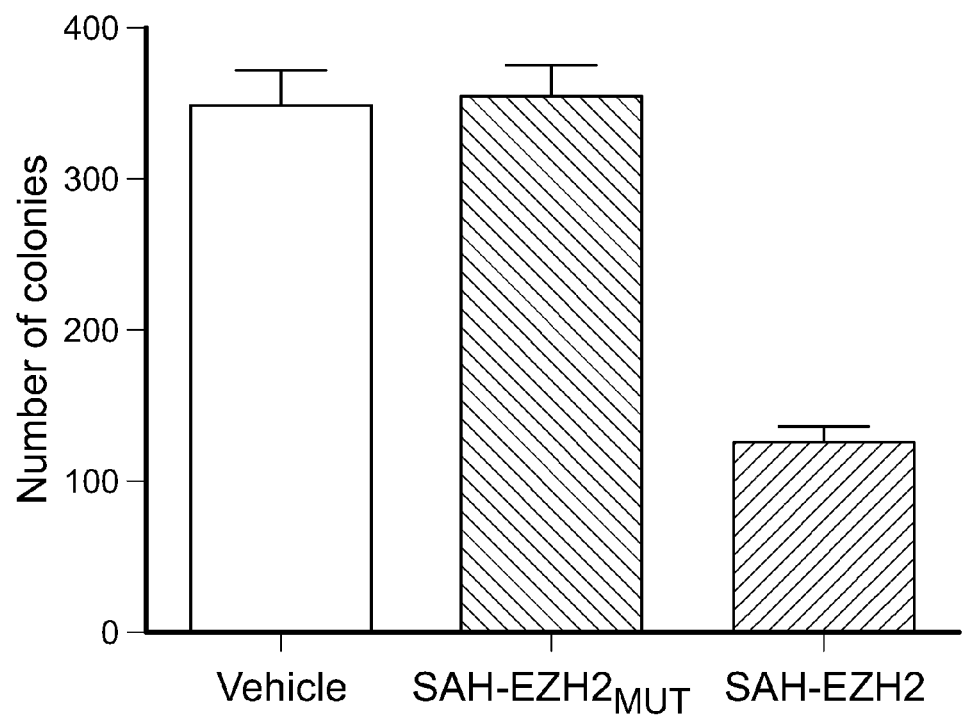
FIG. 25|Suppression of colony-forming potential by SAH-EZH2 as compared to vehicle and SAH-EZH2MUT, p<0.02258. Micrograph insets demonstrate representative colony morphologies.
Figure 25:
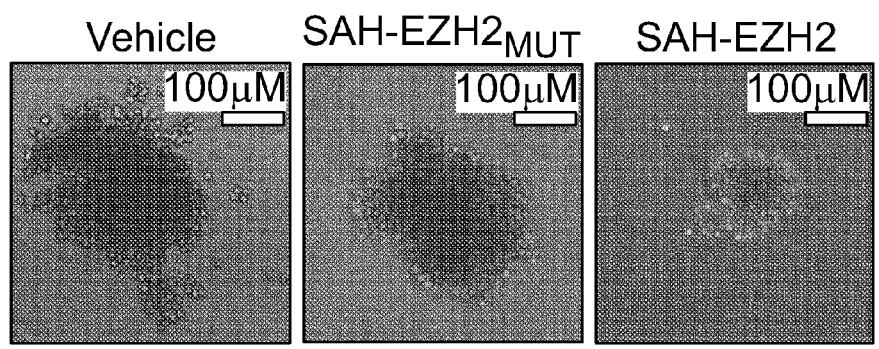
Figure 26:
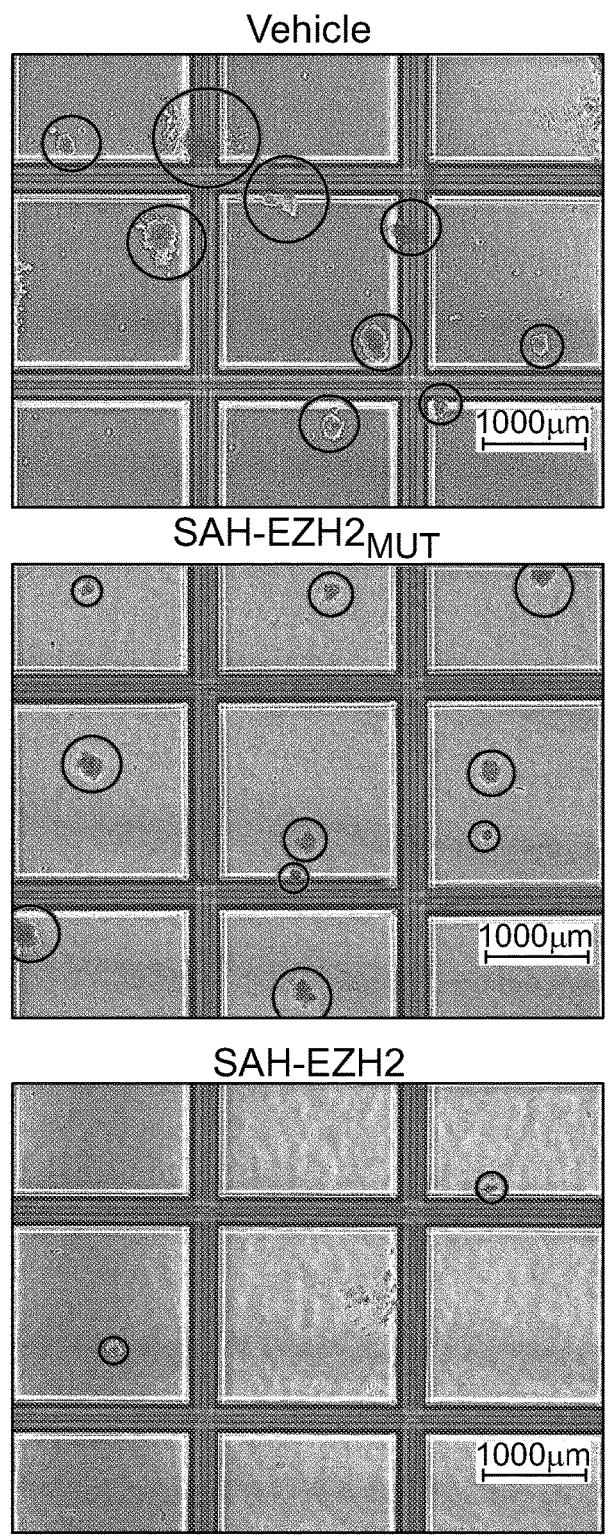
FIG. 26|SAH-EZH2-treated MLL-AF9 cells exhibited decreased colony-forming capacity compared to vehicle and SAH-EZH2$_{MUT}$-treated cells, as evidenced by the low power images.
Figure 27:
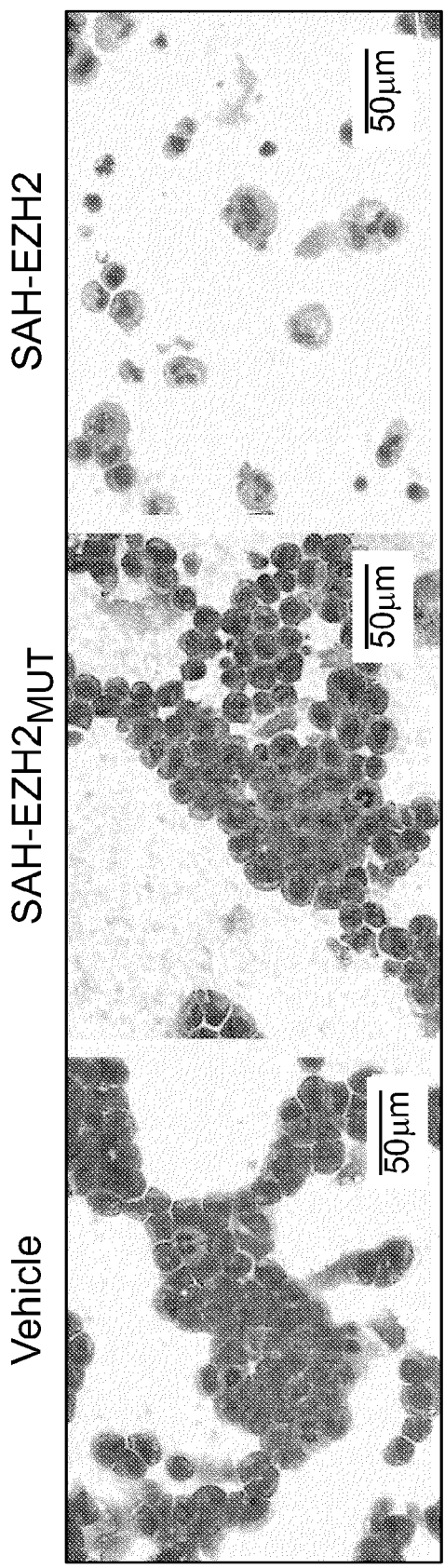
FIG. 27|Morphology of SAH-EZH2-treated MLL-AF9 leukemia cells. Whereas vehicle and SAH-EZH2$_{MUT}$-treated cells retain characteristic blastic features, SAH-EZH2-treated cells exhibit the morphology of monocyte/macrophage differentiation FIG. 28|Flow cytometric analysis of macrophage-specific cell surface marker expression (F4/80) of SAH-EZH2-treated (8 days) MLL-AF9 cells.
Figure 28:
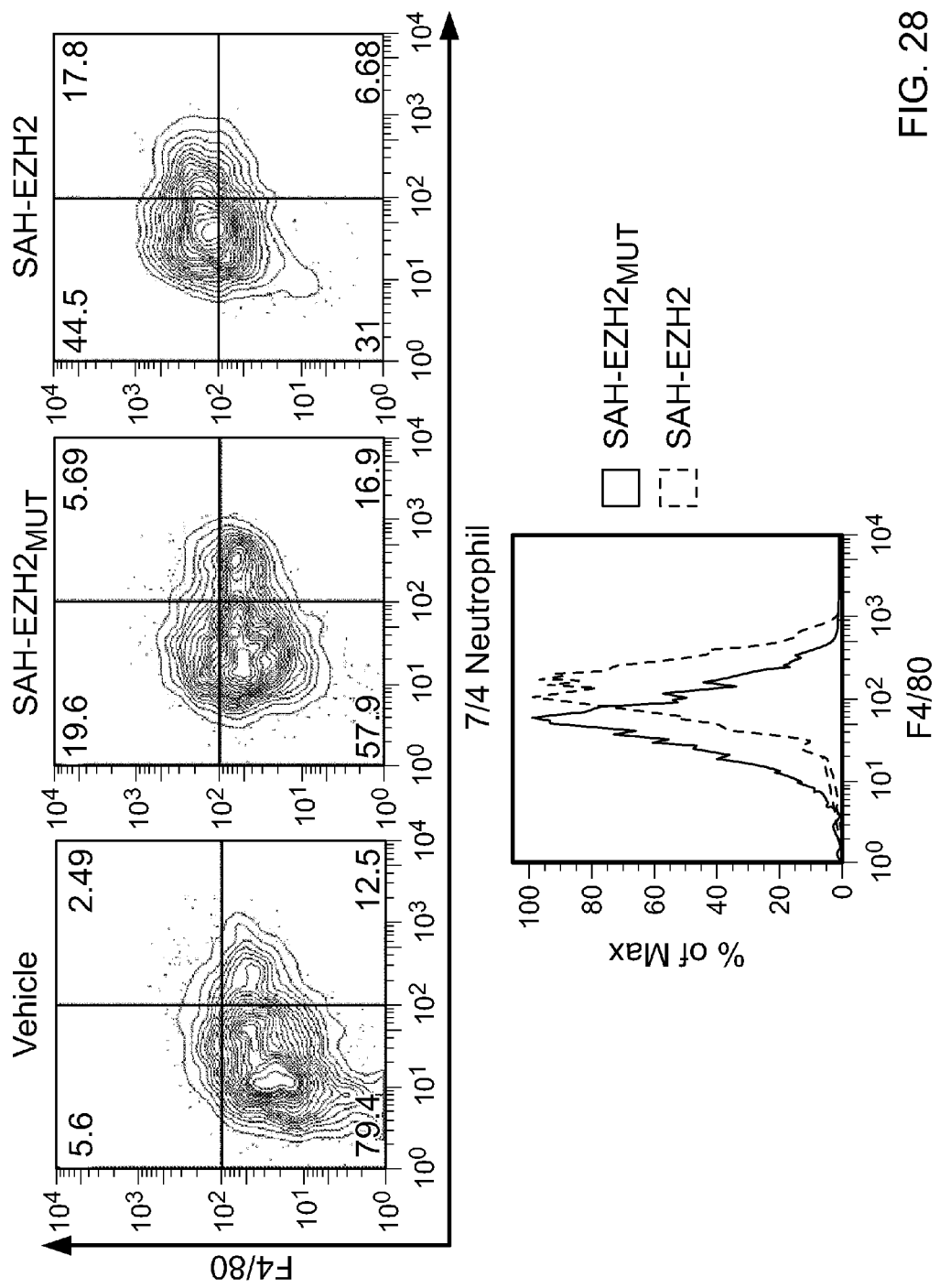
Figure 29A:
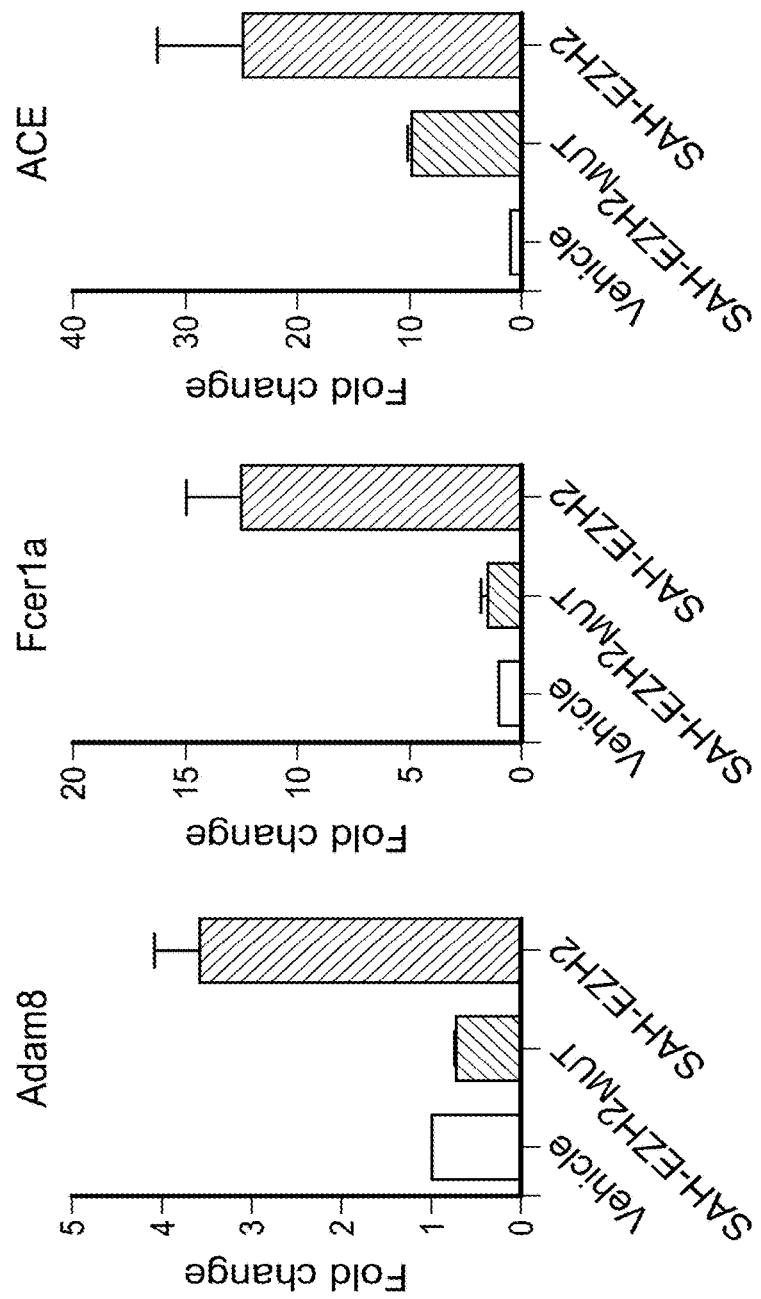
FIG. 29A|Comparative changes in cell surface marker gene expression based on analysis of a 288 gene set in MLL-AF9 cells treated with vehicle (water), SAH-EZH2, or SAH-EZH2$_{MUT}$ (10 μM peptide, 8 days).
Figure 29B:
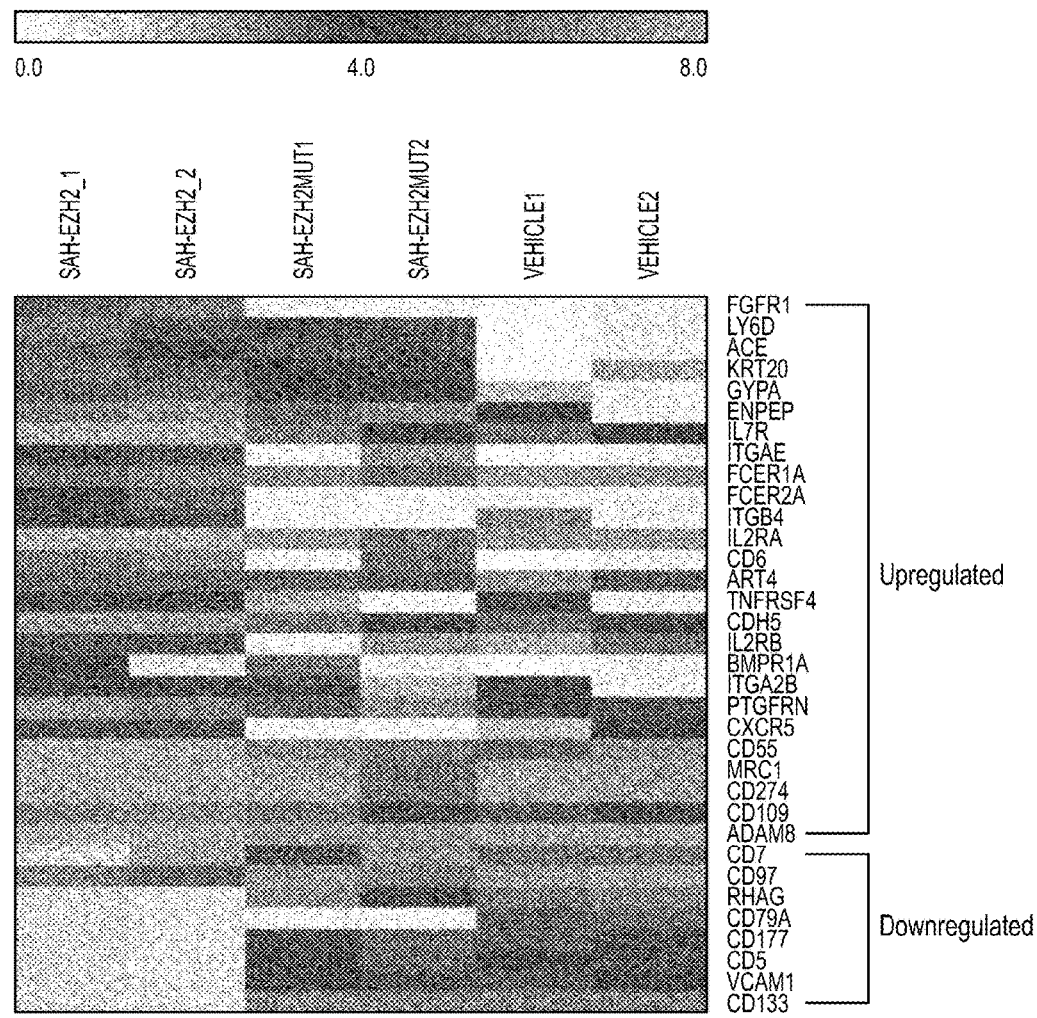
Figure 30A:
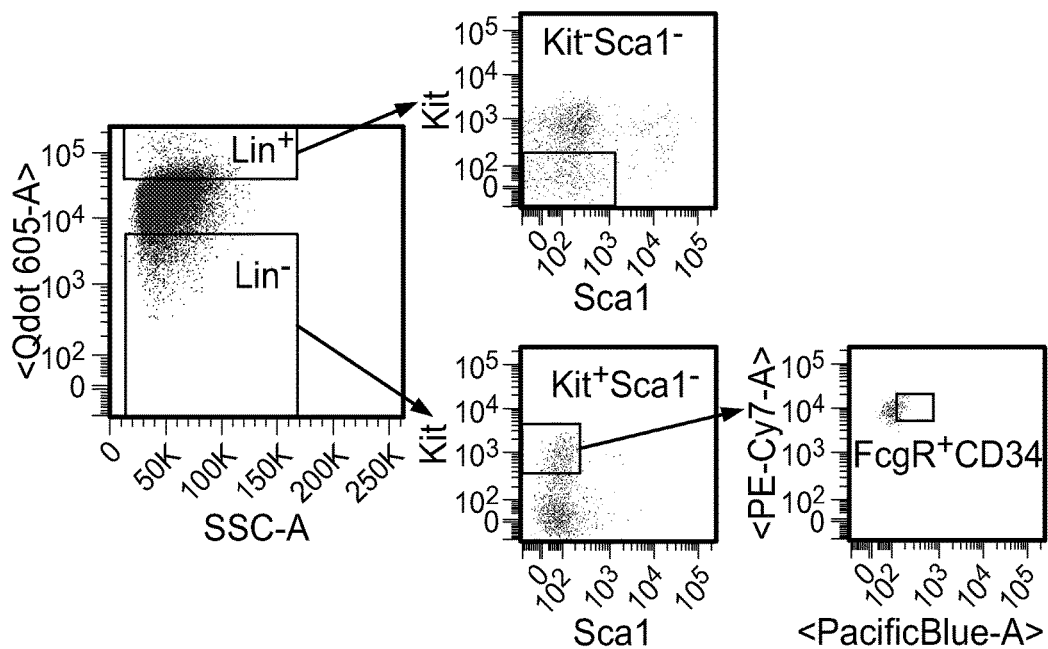
FIG. 30|(a) Cells were harvested from mice and FACS-sorted to isolate undifferentiated MLL-AF9 L-GMP cells (Lin−Kit+Scal−FcgR+CD34+) and differentiated leukemic blasts (Lin+Kit−Scal−). (b) Decreased CD133 expression in SAH-EZH2-treated (8 days) MLL-AF9 leukemia cells (left, p<0.015) and differentiated leukemic Lin+/kit− blast cells (right, p<0.023).
Figure 30B:
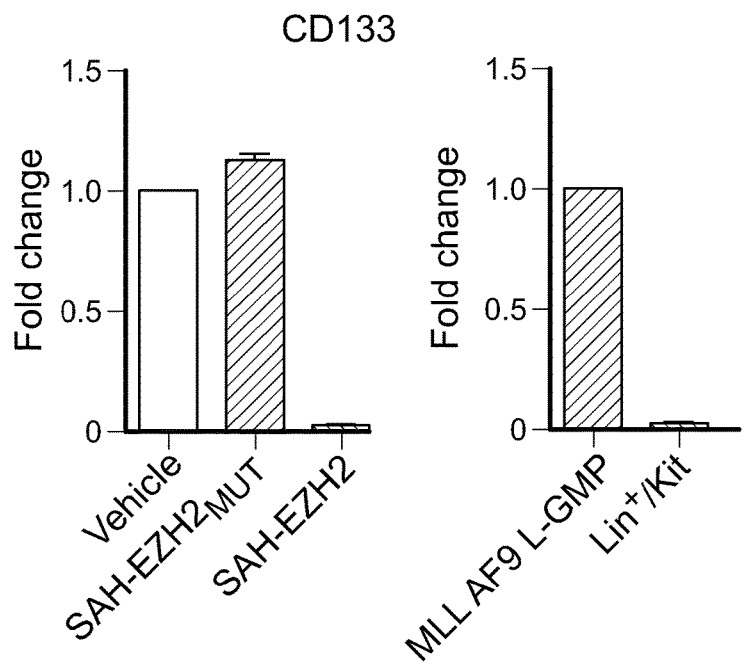

As MLL-AF9 cells are EZH2-dependent and manifest differentiation blockade due to epigenetic deregulation[46], we monitored the impact of SAH-EZH2-mediated disruption of PRC2 activity on the morphology of treated cells. MLL-AF9 cells were exposed to SAH-EZH2 for 14 days, followed by plating on methylcellulose with continued compound incubation. By day 7 after plating, SAH-EZH2 treatment decreased colony-forming capacity by 70% (FIG. 25, FIG. 26) compared to vehicle control, with SAH-EZH2$_{MUT}$ demonstrating no effect. Whereas vehicle- and SAH-EZH2$_{MUT}$-treated cells retained the morphology of immature leukemic blasts, exposure to SAH-EZH2 triggered myeloid cell maturation, with treated cells manifesting a monocyte/macrophage phenotype (FIG. 27). The apparent differentiation of MLL-AF9 leukemia was supported by the positive staining of SAH-EZH2-treated cells with the macrophage specific antibody F4/80 (FIG. 28). These observations phenocopy the induced differentiation of MLL-AF9 cells upon shRNA knockdown or genetic ablation of Ezh2 or Eed[33,33,34,34]. The sequence-based specificity of SAH-EZH2 modulation of PRC2 transcriptional targets was further confirmed by analysis of a cell surface marker 288 gene set in treated cells (FIG. 29A). Induced expression of the macrophage lineage-specific markers Ace1, Adam8 and Fcer1a, as detected by real time qPCR, exemplified the differentiation effect of SAH-EZH2 (FIG. 29B). Conversely, the expression of CD133, a marker associated with hematopoietic stem cells and populations of cancer stem cells[33,34,47-50], decreased significantly upon treatment with SAH-EZH2 (FIG. 30). Reduction in CD133 expression is likewise observed when monocyte/granulocyte progenitors differentiate to mature monocytes/granulocytes[51], and when comparing leukemic stem cell enriched MLL-AF9 leukemic granulocyte monocyte progenitor (L-GMP) cells to the more differentiated leukemic Lin+/kit-blast cells harvested from mice (FIG. 30).

Figure 31:
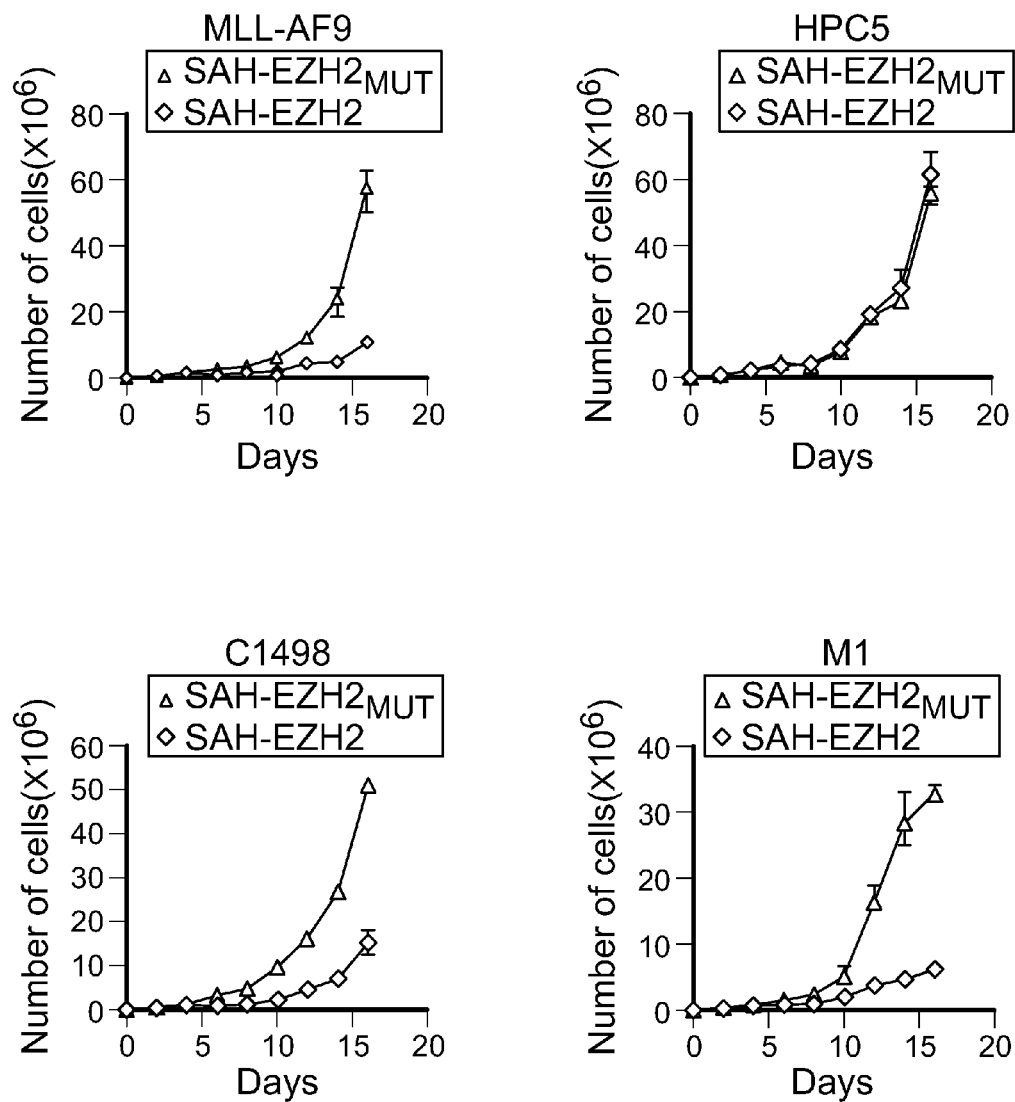
FIG. 31|Effect of SAH-EZH2 peptides on HPC5, C1498 and M1 cell proliferation. Data represent mean±s.e.m. for experiments performed in triplicate FIG. 32|The non-leukemic HPC5 cell line showed no apparent morphologic differences in response to SAH-EZH2 peptides FIG. 33|Comparative effect of SAH-EZH2 on the morphology of MLL-AF9 (differentiated) and HPC5 (undifferentiated) cells observed under high-magnification.
Figure 32:
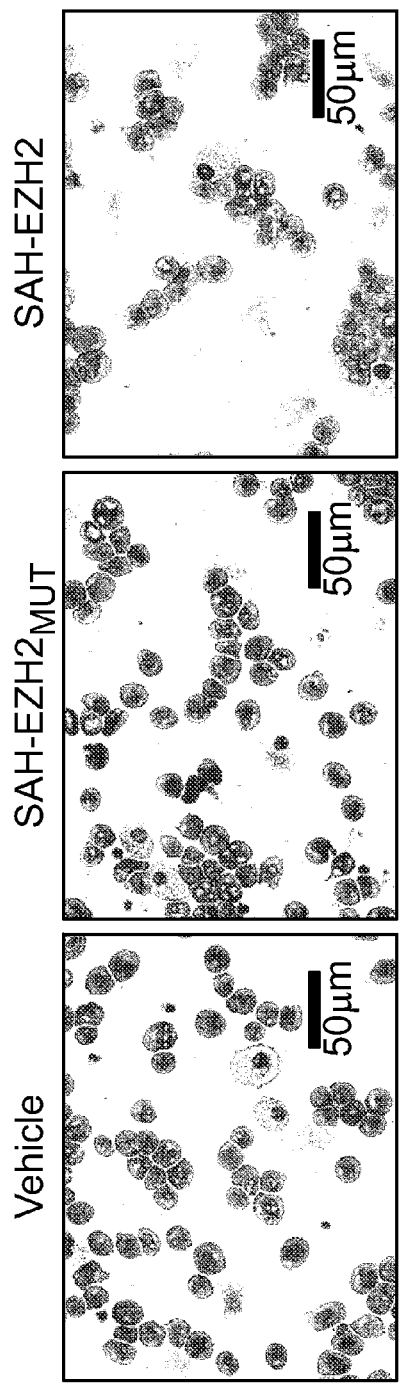
Figure 33:
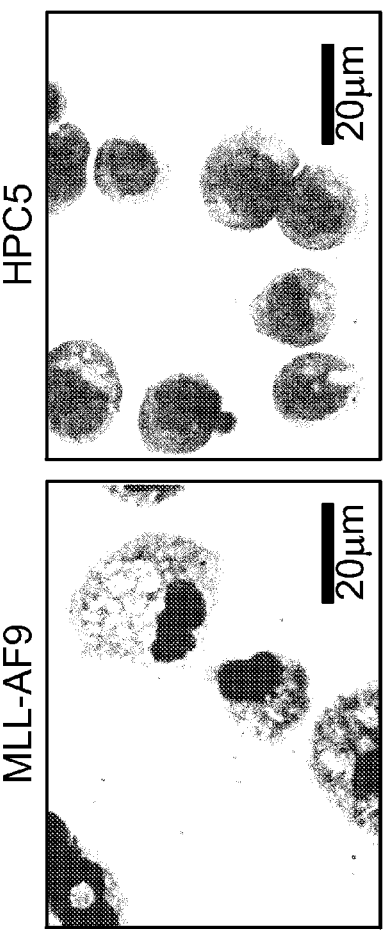

To probe the selectivity of the SAH-EZH2 anti-leukemic effect, we evaluated proliferative and morphologic responses in the immortalized, but non-tumorigenic, primitive hematopoietic progenitor cell line (HPC5), and two additional mouse myeloid leukemia cell lines (M1 and C1492). Of note, HPC5 cells were originally derived from adult bone marrow and then immortalized by expression of the LIM homeobox gene, 1hx2[52]; these cells are unique in that they partially reconstitute hematopoiesis in lethally irradiated mice without causing leukemia. As observed for MLL-AF9 cells, SAH-EZH2, but not its mutant derivative, inhibited the proliferation of C1498 and M1 myeloid leukemia cells, but the non-tumorigenic HPC5 cells showed no effect (FIG. 31). Correspondingly, the undifferentiated appearance of HPC5 cells was unaffected by treatment with vehicle, SAH-EZH2$_{MUT}$, or SAH-EZH2 (FIG. 32, FIG. 33). These data are consistent with the previous observation that shRNA knockdown of PRC2 components EED and Suz12 significantly decreased the proliferation of MLL-AF9; Nras$^{G12D}$ but had minimal impact on the proliferation of the non-leukemic transformed cell line 32D[34]. Thus, we find that the SAH-EZH2 treatment induces proliferation arrest and differentiation of leukemia cells but not untransformed hematopoietic cells.

Example 5

Comparative Anti-leukemic Activity of SAH-EZH2 and the Small Molecule EZH2 Inhibitor GSK126

Figure 34A:
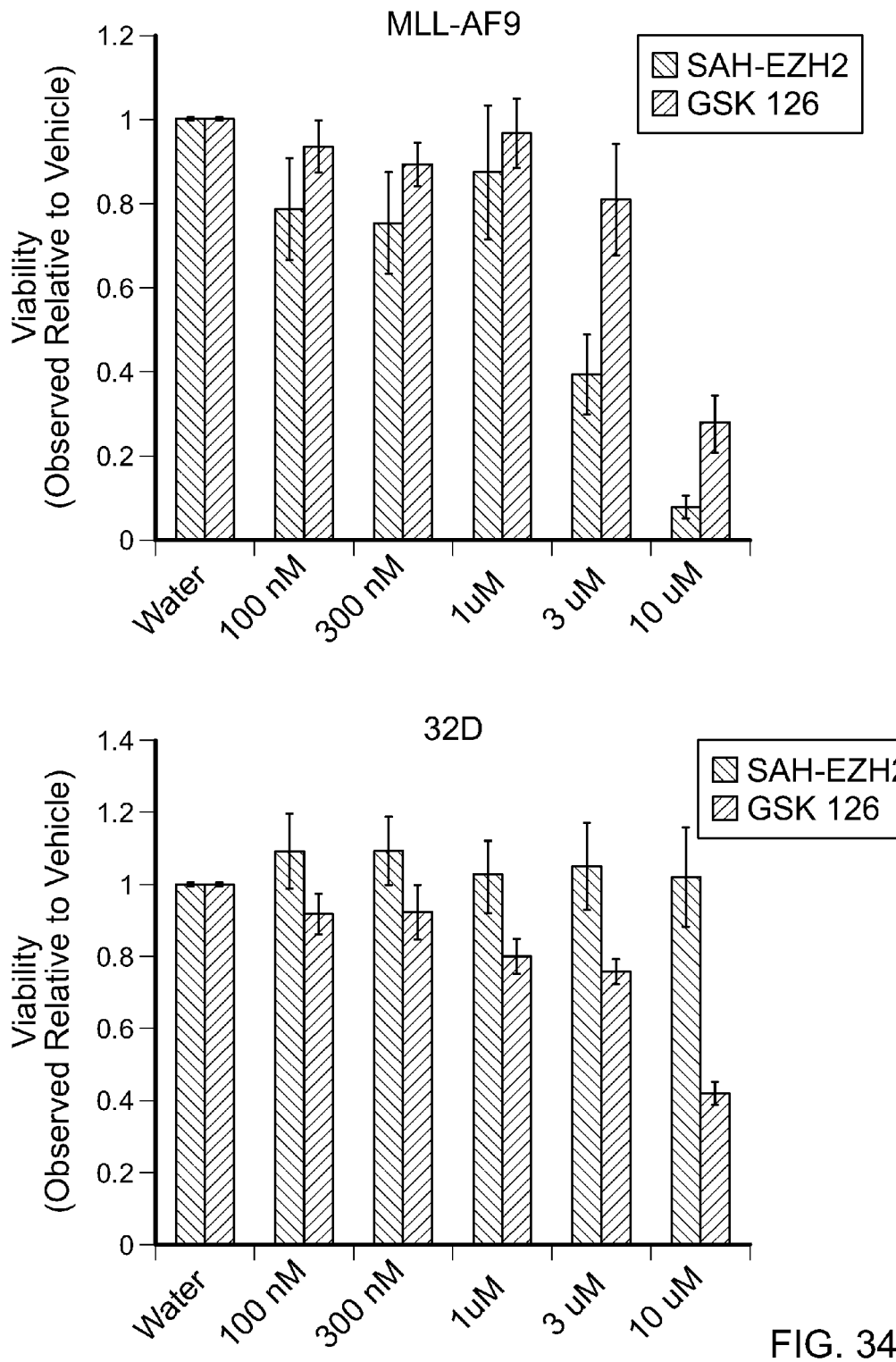
FIG. 34A|Dose-responsive effects of SAH-EZH2 and the small molecule EZH2 inhibitor GSK126 (McCabe et al. Nature, 492: 108-112, 2012) on the viability of EZH2-dependent (MLL-AF9) and EZH2-independent (32D) cell lines. Whereas GSK126 decreased the viability of both the EZH2-dependent and EZH2-independent (non-leukemic) cell lines, the reduction in viability by SAH-EZH2 was specific for the EZH2-dependent cell line, highlighting the selective mechanism of action of SAH-EZH2.
Figure 34B:
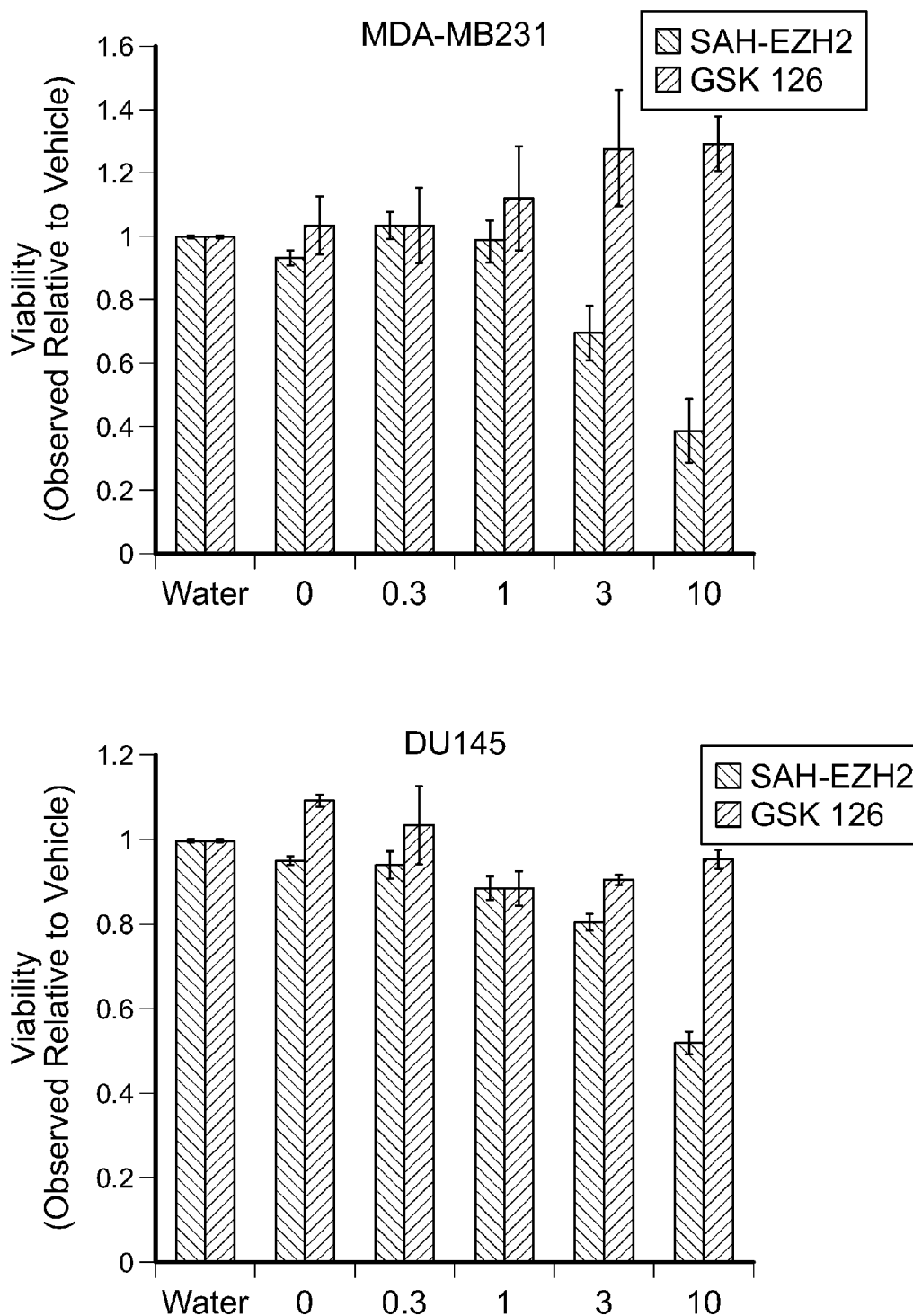
FIG. 34B|Dose-responsive effect of SAH-EZH2, but not GSK126, on the viability of MDA-MB231 breast cancer cells and DU145 prostate cancer cells, both of which are driven by pathologic EZH2 activity.
Figure 35:
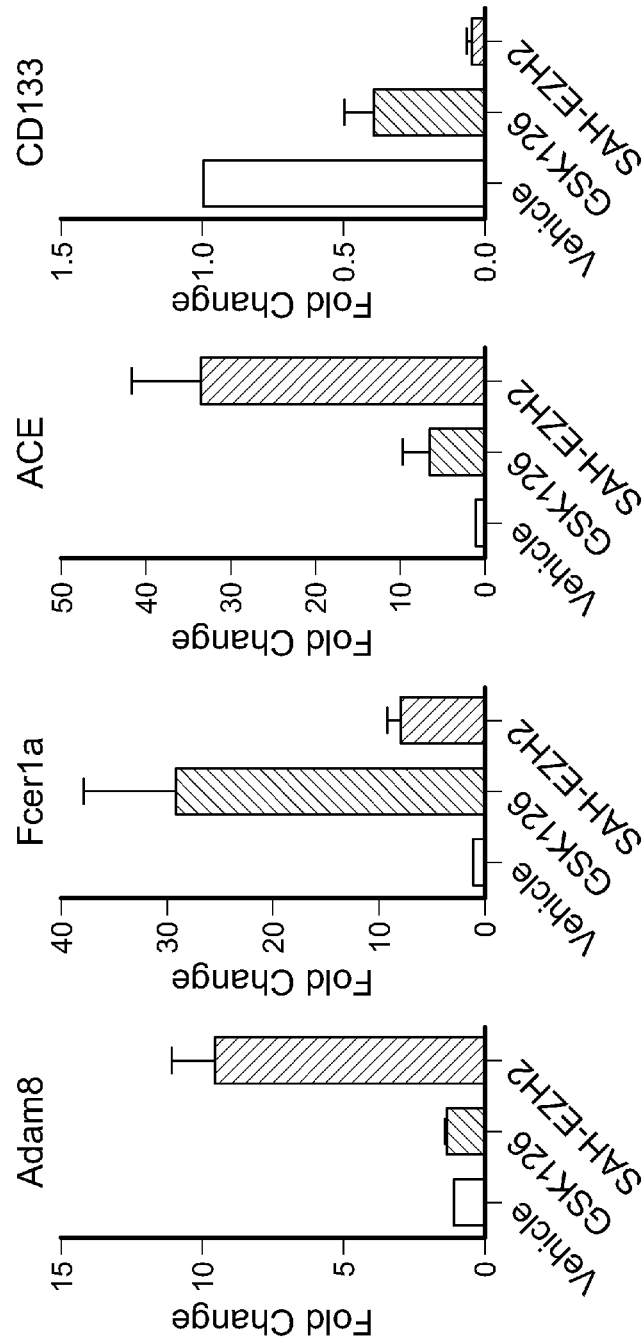
FIG. 35|Comparison of the effects of SAH-EZH2 and GSK126 on lineage specific cell surface marker expression of MLL-AF9 cells. Whereas the most notable effect of GSK126 was to increase expression of Fcer1a, SAH-EZH2 exhibited broader activity, with pronounced increases in the expression levels of Adam8, Fcer1a, and ACE. Whereas both GSK126 and SAH-EZH2 decreased the expression of cancer stem cell marker CD133, as measured after 8 days of treatment, SAH-EZH2 manifested a comparatively more robust suppressive effect.
Figure 36:
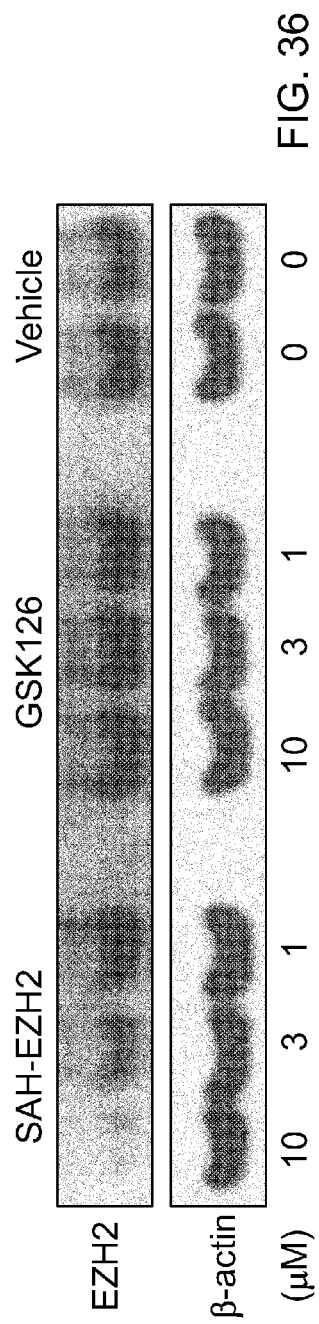
FIG. 36|Treatment of MLL-AF9 cells with SAH-EZH2 causes a dose-responsive decrease in EZH2 protein levels, whereas GSK126 has no such effect. These data highlight a distinct mechanism of action for SAH-EZH2, reflected by its capacity to target EED and dissociate the components of the PRC2 complex, leading to overall reduction of EZH2 levels.

To compare the functional and mechanism-based cellular activities of SAH-EZH2 and GSK126, a small molecule inhibitor of EZH2 enzymatic activity (McCabe et al. *Nature*, 492: 108-112, 2012), we conducted viability assays on the EZH2-dependent cell line MLL-AF9 and the EZH2-independent (non-leukemic) cell line 32D. Whereas GSK126 decreased the viability of both the EZH2-dependent and EZH2-independent (non-leukemic) cell lines, the reduction in viability by SAH-EZH2 was specific for the EZH2-dependent cell line, highlighting the selective mechanism of action of SAH-EZH2 (FIG. 34A). We further demonstrated the dose-responsive effect of SAH-EZH2, but not GSK126, on the viability of MDA-MB231 breast cancer cells and DU145 prostate cancer cells, both of which are driven by pathologic EZH2 activity (FIG. 34B). We next compared the effects of SAH-EZH2 and GSK126 on lineage specific surface marker expression in MLL-AF9 cells. Whereas the most notable effect of GSK126 was to increase expression of Fcer1a, SAH-EZH2 exhibited broader activity, increasing the expression levels of Adam8, Fcer1a, and ACE (FIG. 35). Whereas both GSK126 and SAH-EZH2 decreased the expression of cancer stem cell marker CD133, as measured after 8 days of treatment, SAH-EZH2 manifested a comparatively more robust suppressive effect (FIG. 35). As GSK126 has been reported to directly inhibit the enzymatic activity of EZH2 whereas SAH-EZH2 targets EED to dissociate the enzymatic complex, we explored the potential impact of these differential mechanisms of action on EZH2 protein levels in cells. We find that SAH-EZH2, but not GSK126, treatment induces a dose-responsive reduction in EZH2 protein levels (FIG. 36), consistent with SAH-EZH2 mediated destabilization of the EZH2 protein upon dissociation of the EZH2/EED complex. Given the distinct mechanisms of action of SAH-EZH2 and GSK126, we explored whether co-administration of the two compounds would enhance the anti-leukemic effects. Indeed, we observe that combination treatment of MLL-AF9 and Karpas422 cells with SAH-EZH2 and GSK126 dose-responsively enhances anti-proliferative activity compared to that of the respective compounds administered as single agents (FIG.

Figure 37:
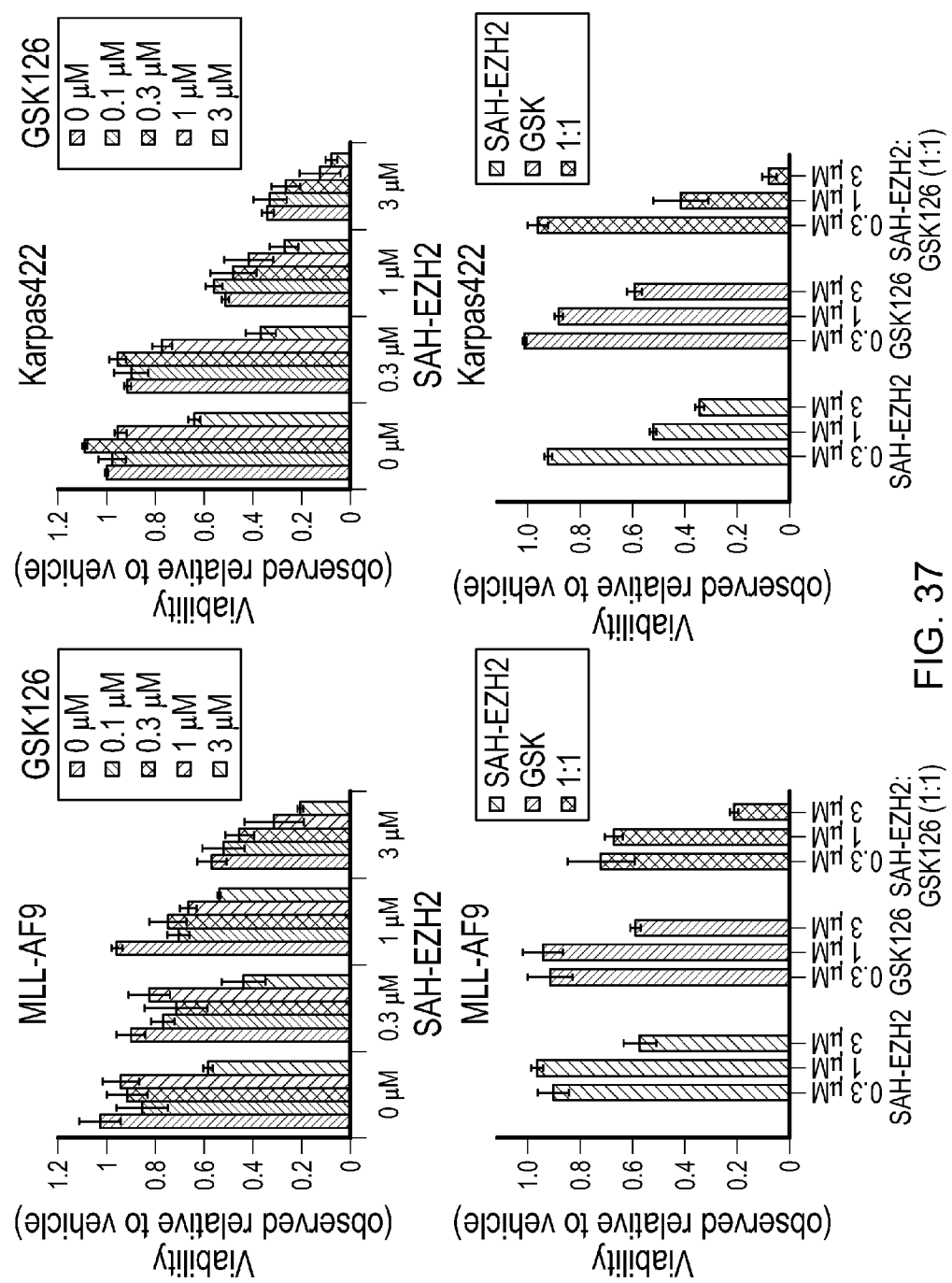
FIG. 37|Combination treatment of MLL-AF9 and Karpas422 cells with SAH-EZH2 and GSK126 manifests enhanced suppression of cellular viability compared to that of the respective compounds administered as single agents (top), with Calcusyn analysis documenting the synergistic effect of the combination (bottom).
Figure 38:
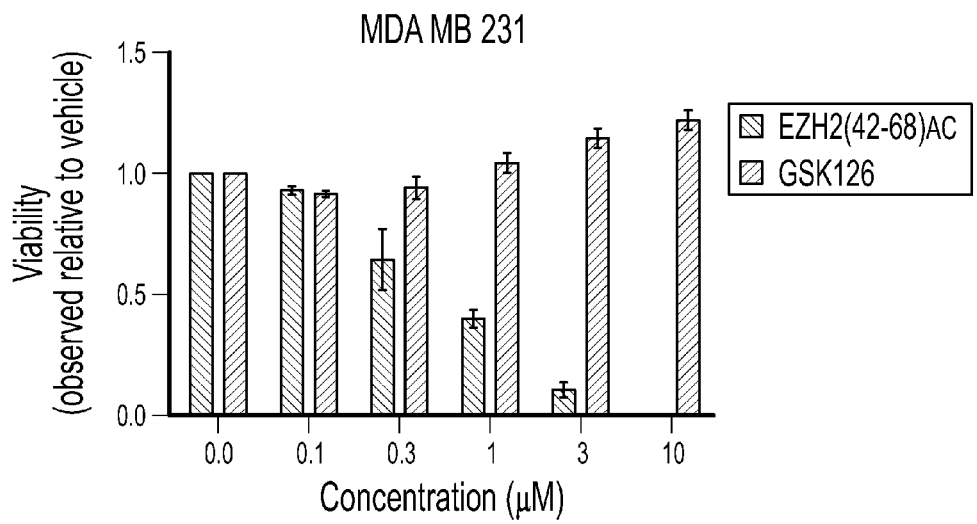
FIG. 38|Table showing the design of a doubly stapled SAH-EZH2 peptide and its improved binding activity compared to SAH-EZH2

37, top). Calcusyn analysis (Chou T C, Pharm Rev, 58:621-681, 2006) revealed $ED_{50}$ combination indices of 0.11 and 0.74 for MLL-AF9 and Karpas422 cells, respectively, indicating a synergistic effect of the combination (i.e. a combination index <1 reflects synergy) (FIG. 37, bottom). Thus, SAH-EZH2 manifests a unique mechanism of action by targeting EED, dissociating the EZH2/EED complex, and thereby reduces EZH2 protein levels. As a result, the H3K27Me3 mark is reduced over time and PRC2 transcriptional effects are inhibited, leading to anti-proliferative and induced-differentiation effects on EZH2-dependent leukemia cells.

Example 6

Enhanced EED Binding Affinity of a Doubly Stapled SAH-EZH2 Peptide

The EED binding affinities of SAH-EZH2 and SAH-EZH2(42-68)$_{AC}$ were assessed by their capacities to displace FITC-labeled EZH2(42-68) peptide from EED. Serially diluted acetyl-SAH-EZH2 and the doubly stapled acetyl-SAH-EZH2(42-68)AC (dose range from 2.5 nM to 10 µM) were incubated with purified EED (200 nM) and FITC-labeled EZH2(42-68) peptide (20 nM) for 30 min, followed by measurement of fluorescence polarization. N-terminal acetylated SAH-EZH2(42-68)$_{AC}$ displaced FITC-labeled EZH2(42-68) peptide from EED two times more efficiently than SAH-EZH2. The non-binding EZH2(47-64) construct was used as a negative control.

Example 7

Anti-proliferative Activity of the Doubly Stapled SAH-EZH2(42-68)$_{AC}$ Peptide on a Diverse Spectrum of Cancer Cell Lines To test the anti-proliferative effect of SAH-EZH2(42-68)$_{AC}$, breast (MDA-MB231) and prostate (DU145) cancer cell lines were treated with SAH-EZH2(42-68)$_{AC}$ at the indicated doses for 8 days and measured for viability by Cell Titer Glo®SAH-EZH2(42-68)$_{AC}$ was added to the culture medium once every other day. SAH-EZH2(42-68)$_{AC}$ demonstrated enhanced dose-dependent anti-proliferative effects compared to SAH-EZH2 treatment, which was administered twice daily (FIG. 34A) compared to the every other day schedule of SAH-EZH2(42-68)AC (FIG. 39). We further tested the anti-proliferative effects of SAH-EZH2(42-68)AC on a Ewing Sarcoma cell line (TC71) and neuroblastoma cell line (Kelly). The cells were treated with SAH-EZH2 (42-68)$_{AC}$ at the indicated doses for 6 days on an every other day schedule and then measured for viability using Cell Titer Glo®. SAH-EZH2(42-68)$_{AC}$ exhibits noticeable anti-proliferative effects on both TC71 and Kelly in a dose-dependent manner (FIG. 40). To test the anti-proliferative effect on chronic myelogenous leukemia, SAH-EZH2(42-68)$_{AC}$ was added to K562 cells at 10 µM every other day and viability was measured at days 2, 4, 6, and 10 using Cell Titer Glo®. SAH-EZH2(42-68)$_{AC}$ decreased proliferation of K562 cells in a dose-responsive manner (FIG. 41). To assess the anti-proliferative effects of SAH-EZH2(42-68)$_{AC}$ on androgen-dependent and advanced androgen-independent prostate cancer, SAH-EZH2(42-68)$_{AC}$ was added to cell culture every other day at the indicated doses and viability measured using Cell Titer Glo®. Whereas SAH-EZH2(42-68)$_{AC}$ was observed to anti-proliferative activity in each case, advanced androgen independent cancer cells (Abl, 22Rv1) were more sensitive to SAH-EZH2(42-68)$_{AC}$ treatment (IC50s for growth <1 µM) compared to the androgen-dependent LNCaP cells (FIG. 42).

Methods Used in the Examples

Synthesis of Stabilized Alpha-Helix of EZH2 Peptides: SAH-EZH2 peptides were designed based on the EED-binding domain of EZH2, with replacement of natural amino acids with olefinic residues at sites on the non-interacting face of the EZH2 helix, as defined by X-ray crystallography[32]. Hydrocarbon stapling, peptide purification and quantitation, and characterization by circular dichroism were performed as previously described in detail[35,36].

Cell Lines and Tissue Culture: MLL-AF9 leukemia cells were generated as described in Krivtsov et al.[46] and cultured in AF9 media, containing IMDM (Invitrogen) supplemented with 5% fetal calf serum (FCS), 5 ng/µl mouse recombinant IL3 (R&D systems), and 1% penicillin/streptomycin (Invitrogen). COS7 cells (ATCC) were cultured in DMEM media supplemented with 10% FCS and 1% penicillin/streptomycin. Sf21 cells (Invitrogen) were cultured in Grace insect media (Invitrogen) supplemented with 10% FCS and 1% penicillin/streptomycin.

SAH-EZH2/EED Binding Analyses: For fluorescence polarization binding analysis, C-terminal His-tagged EED (His-EED) was expressed in *Escherichia coli* BL21(DE3) using 0.3 mM IPTG for 6 h at room temperature. Bacterial pellet lysate was loaded onto a Ni-NTA column (Novagen) for purification of His-EED. Fluorescinated stapled peptides (final concentration, 25 nM) were incubated with His-EED (serial dilution range, 25 nM-8 µM) at room temperature until equilibrium was reached (~15 min) Binding activity was measured by fluorescence polarization on a Perkin-Elmer LS50B luminescence 5 spectrophotometer. $K_D$ values were determined by following equation, $$y = AF + \left(\frac{AB - AF}{L}\right) \times \frac{L + K_D + X - \sqrt{(L + K_D + X)^2 - 4 \times L \times X}}{2}$$

y: Fluorescence polarization, X: Receptor concentration, L: Ligand concentration AF: Minimum value of y, AB: Maximum value of y For anti-FITC pull down-based binding assays, HA-EED was produced in Sf21 cells as described in Shen et al.[29,46]. FITC-SAH-EZH2 peptides (final concentration, 50, 10, and 2 nM) were mixed with 2 µl, 0.5 µl and 0.2 µl of anti-FITC antibody (Abcam, 1 mg/ml) respectively, and incubated with 30 µl of protein G agarose (Roche) in 400 µl binding buffer (pH 8.0, 20 mM Tris-HCl, 150 mM NaCl, 0.3% NP40, 10% glycerol). After successive washes, HA-EED (final concentration of 40 nM each tube) was added and incubated for 3 h, followed by detection of HA-EED bound to FITC-SAH-EZH2 peptides by anti-HA (Santa Cruz Biotechnology) western analysis. Detection of FITC-SAH-EZH2 peptides was accomplished by fluorescence scan (GE Healthcare Life Sciences, Typhoon 9200).

Cellular Uptake of SAH-EZH2 Peptides: MLL-AF9 leukemia cells were seeded in 48-well plates at densities of 1.0×10⁶ cells per well in 200 µl of AF9 media. FITC-SAH-EZH2 peptides (final concentrations, 4, 2 and 1 µM) were added to the cells and incubated for 8 h. Cells were then washed three times with phosphate buffer saline (PBS, Sigma) and then trypsinized (0.05% Trypsin-EDTA, Invitrogen) at 37° C. for 5 min to remove any residual peptide attached to the cell surface. The cells were lysed with SDS loading buffer (Biorad) and brief sonication. Lysates were electrophoresed on SDS-PAGE gels (Biorad, Criterion tristricine 10-20%) and subjected to fluorescence scan (GE healthcare, Typhoon imager 9400)

Confocal Microscopy: COS7 cells were plated in 8-well CC²™ Chamber Slides™ (Nunc) for 1-2 days prior to experimentation. Slides were washed twice with serum-free DMEM media (Invitrogen) and FITC-SAH-EZH2 peptides were added in serum-free DMEM media at a final concentration of 4 µM. After 3 h incubation, an equal volume of DMEM media supplemented with 20% FCS was added, and the cells subjected to an additional 5 h incubation. Slides were washed three times with PBS and fixed with 4% paraformaldehyde (Electron Microscopy) for 12 min. After blocking with 5% goat serum (Vector) and staining with EED antibody (Millipore, produced in rabbit), the slides were stained with Alexa Fluor 647 donkey anti-rabbit IgG (Invitrogen). Nuclei were stained upon application of mounting medium containing DAPI (Vector). Confocal images were acquired on a Zeiss LSM700 microscopy and analyzed with ZEN 2011 software (Zeiss).

Immunoprecipitation Analyses: To assess the interaction between SAH-EZH2 peptides and native EED, MLL-AF9 leukemia cells ($2\times10^7$) were cultured in 10 ml AF9 media using 10 cm dishes (BD Biosciences) and FITC-SAH-EZH2 peptides added to final concentration of 20 µM, followed by 8-12 h incubation. Treated cells were washed and trypsinized as above, lysed and then incubated with 50 µl of FITC-antibody (1 mg/ml) and 100 µl of protein G agarose (Roche) for 3 h. The amount of EED bound to FITC-SAH-EZH2 peptides was assessed by anti-EED western analysis (Millipore). To monitor for dissociation of native EED-EZH1/EZH2 complexes by SAH-EZH2, Sf21 cells were co-transfected with HA-EED and FLAG-EZH1 or FLAG-EZH2 baculovirus. EED-EZH1 and EED-EZH2 complexes were purified by anti-FLAG agarose (Sigma). EED-EZH1 and EED-EZH2 complexes (40 nM final concentration) were incubated with FITC-SAH-EZH2 peptides (final concentrations, 10, 3 and 1 µM) in 200 µl binding buffer for 2 h. After successive washes, the mixtures were incubated with anti-HA agarose (Sigma) and the level of HA-EED-bound EZH1 and EZH2 assessed by anti-HA western analysis.

Analysis of Trimethylation Status: MLL-AF9 leukemia cells were seeded in 48-well plates at densities of $2\times10^5$ cells per well in 200 µl of AF9 media and then treated with SAH-EZH2 peptides (10 µM) twice daily for 7 days. Cells were then lysed in loading buffer (Biorad) with brief sonication and electrophoresed on SDS-PAGE gels (Thermoscientific, 4-20%). Levels of Lys4, Lys9, Lys27 (07-449, Millipore) and Lys36 trimethylation were analyzed by the corresponding trimethyl mark-specific antibodies (Millipore). For flow cytometric analysis of H3 Lys27 trimethylation, MLL-AF9 cells were treated with SAH-EZH2 peptides (10 µM) twice daily for 7 days and then fixed in 70% cold ethanol for overnight at −20° C. Cells were washed twice in PBS, stained with anti-Lys27-Me3 antibody (Cell Signaling, #9733S) for 20 min and then anti-rabbit IgG Alexafluoro-647 (Invitrogen) for 20 min, followed by FACS analysis using a BD FACSCalibur.

Cell Proliferation, Apoptosis, and Cell Cycle Analyses: To monitor the effect of SAH-EZH2 peptides on cell proliferation, MLL-AF9 cells were seeded in 48 well plates at densities of $2\times10^5$ cells per well in 150 µl of AF9 media and treated with SAH-EZH2 peptides (10 µM) twice daily. Cells were counted every other day using a hematocytometer. To evaluate apoptosis induction, the cells were stained with Annexin V5-PE and 7-AAD after 8 or 16 days of treatment with SAH-EZH2 peptides. Camptothecin (Biovision) was used as a positive control (2 µM, 48 h). Cells were analyzed using a BD FACScaliber and data was processed using Flowjo software. For cell cycle analysis, cells were stained with propidium iodide (BD Biosciences) after 4 or 8 days of treatment with SAH-EZH2 peptides. Cells were analyzed using a BD FACSCalibur and data processed using Modfit software.

Cellular Differentiation Analyses: To monitor the morphology of treated cells, MLL-AF9 leukemia cells were exposed to SAH-EZH2 peptides in AF9 media for 14 days, as described above. Cells were counted and then diluted into Methocult (STEMCELL technologies) supplemented with 10 ng/ml IL3, 10 ng/ml IL6, 10 ng/ml SCF, 5% FCS, and 1% penicillin/streptomycin at a density of 1000 cells/ml with continued exposure to SAH-EZH2 peptides (20 µM). Aliquots of methocult (1 ml) were plated in 3 cm dishes (BD Biosciences) and colonies counted after 7 day incubation. Cells were washed with PBS (Sigma), cytospun, and then stained using modified Giemsa stain (Sigma). Morphology was assessed by light microscopy (Nikon Eclipse E800 microscope). HPC5 cells were treated as above except that a higher concentration of SCF (100 ng/ml) was used in the culture media. To detect macrophage-specific cell surface marker expression, MLL-AF9 cells were treated with SAH-EZH2 peptides for 7 d followed by successive washes in PBS and immunostaining with Rat Anti Mouse F4/80 Antigen Alexa 647 (AbD Serotec) and PE Anti-Mouse Neutrophils Monoclonal antibody (CEDARLANE) antibodies. Cells were analyzed by BD FACS Calibur and data processed using Flowjo software.

Cited Publications

1. Nagy, P. L., Griesenbeck, J., Kornberg, R. D. & Cleary, M. L. A trithorax-group complex purified from *Saccharomyces cerevisiae* is required for methylation of histone H3. *Proc. Natl. Acad. Sci. U.S.A.* 99, 90-94 (2002).

2. Beisel, C., Imhof, A., Greene, J., Kremmer, E. & Sauer, F. Histone methylation by the *Drosophila* epigenetic transcriptional regulator Ash1. *Nature* 419, 857-862 (2002).

3. Cao, R. Role of Histone H3 Lysine 27 Methylation in Polycomb-Group Silencing. *Science* 298, 1039-1043 (2002).

4. Czermin, B. et al. *Drosophila* enhancer of Zeste/ESC complexes have a histone H3 methyltransferase activity that marks chromosomal Polycomb sites. *Cell* 111, 185-196 (2002).

5. Müller, J. et al. Histone methyltransferase activity of a *Drosophila* Polycomb group repressor complex. *Cell* 111, 197-208 (2002).

6. Kuzmichev, A. Histone methyltransferase activity associated with a human multiprotein complex containing the Enhancer of Zeste protein. *Genes & Development* 16, 2893-2905 (2002).

7. Varambally, S. et al. The polycomb group protein EZH2 is involved in progression of prostate cancer. *Nature* 419, 624-629 (2002).

8. Kleer, C. G. et al. EZH2 is a marker of aggressive breast cancer and promotes neoplastic transformation of breast epithelial cells. *Proc. Natl. Acad. Sci. U.S.A.* 100, 11606-11611 (2003).

9. Sasaki, M. et al. The overexpression of polycomb group proteins Bmil and EZH2 is associated with the progression and aggressive biological behavior of hepatocellular carcinoma. *Lab. Invest.* 88, 873-882 (2008).

10. Hinz, S. et al. Expression of the polycomb group protein EZH2 and its relation to outcome in patients with urothelial carcinoma of the bladder. *J. Cancer Res. Clin. Oncol.* 134, 331-336 (2007).

11. He, L.-R. et al. High expression of EZH2 is associated with tumor aggressiveness and poor prognosis in patients with esophageal squamous cell carcinoma treated with definitive chemoradiotherapy. *Int. J. Cancer* 127, 138-147 (2009).

12. Wagener, N. et al. Enhancer of zeste homolog 2 (EZH2) expression is an independent prognostic factor in renal cell carcinoma. *BMC Cancer* 10, 524 (2010).

13. Wang, C. et al. EZH2 Mediates epigenetic silencing of neuroblastoma suppressor genes CASZ1, CLU, RUNX3, and NGFR. *Cancer Research* 72, 315-324 (2012).

14. Beke, L., Nuytten, M., Van Eynde, A., Beullens, M. & Bollen, M. The gene encoding the prostatic tumor suppressor PSP94 is a target for repression by the Polycomb group protein EZH2. *Oncogene* 26, 4590-4595 (2007).

15. Yu, J. et al. Integrative Genomics Analysis Reveals Silencing of β-Adrenergic Signaling by Polycomb in Prostate Cancer. *Cancer Cell* 12, 419-431 (2007).

16. Sasaki, M., Yamaguchi, J., Itatsu, K., Ikeda, H. & Nakanuma, Y. Overexpression of polycomb group protein EZH2 relates to decreased expression of p16 INK4a in cholangiocarcinogenesis in hepatolithiasis. *J Pathol* 215, 175-183 (2008).

17. Banerjee, R. et al. The tumor suppressor gene rap1-GAP is silenced by miR-101-mediated EZH2 overexpression in invasive squamous cell carcinoma. *Oncogene* 30, 4339-4349 (2011).

18. Kong, D. et al. Loss of let-7 up-regulates EZH2 in prostate cancer consistent with the acquisition of cancer stem cell signatures that are attenuated by BR-DIM. *PLoS ONE* 7, e33729 (2012).

19. Varambally, S. et al. Genomic Loss of microRNA-101 Leads to Overexpression of Histone Methyltransferase EZH2 in Cancer. *Science* 322, 1695-1699 (2008).

20. Carvalho, J. et al. *Lack of microRNA-101 causes E-cadherin functional deregulation through EZH2 up-regulation in intestinal gastric cancer. J Pathol* 228, 31-44 (2012).

21. Morin, R. D. et al. Somatic mutations altering EZH2 (Tyr641) in follicular and diffuse large B-cell lymphomas of germinal-center origin. *Nature Genetics* 42, 181-185 (2010).

22. Yap, D. B. et al. Somatic mutations at EZH2 Y641 act dominantly through a mechanism of selectively altered PRC2 catalytic activity, to increase H3K27 trimethylation. *Blood* 117, 2451-2459 (2011).

23. Sneeringer, C. J. et al. Coordinated activities of wild-type plus mutant EZH2 drive tumor-associated hypertrimethylation of lysine 27 on histone H3 (H3K27) in human B-cell lymphomas. *Proceedings of the National Academy of Sciences* 107, 20980-20985 (2010).

24. McCabe, M. T. et al. Mutation of A677 in histone methyltransferase EZH2 in human B-cell lymphoma promotes hypertrimethylation of histone H3 on lysine 27 (H3K27). *Proceedings of the National Academy of Sciences* 109, 2989-2994 (2012).

25. Fussbroich, B. et al. EZH2 Depletion Blocks the Proliferation of Colon Cancer Cells. *PLoS ONE* 6, e21651 (2011).

26. Fujii, S., Ito, K., Ito, Y. & Ochiai, A. Enhancer of Zeste Homologue 2 (EZH2) Down-regulates RUNX3 by Increasing Histone H3 Methylation. *Journal of Biological Chemistry* 283, 17324-17332 (2008).

27. Wilson, B. G et al. Epigenetic Antagonism between Polycomb and SWI/SNF Complexes during Oncogenic Transformation. *Cancer Cell* 18, 316-328 (2010).

28. Chamberlain, S. J., Yee, D. & Magnuson, T. Polycomb repressive complex 2 is dispensable for maintenance of embryonic stem cell pluripotency. *Stem Cells* 26, 1496-1505 (2008).

29. Shen, X. et al. Jumonji Modulates Polycomb Activity and Self-Renewal versus Differentiation of Stem Cells. *Cell* 139, 1303-1314 (2009).

30. Knutson, S. K. et al. A selective inhibitor of EZH2 blocks H3K27 methylation and kills mutant lymphoma cells. *Nature Chemical Biology* (2012).doi:10.1038/nchembio.1084

31. McCabe, M. T. et al. EZH2 inhibition as a therapeutic strategy for lymphoma with EZH2-activating mutations. *Nature* (2012).doi:10.1038/nature11606

32. Han, Z. et al. Structural Basis of EZH2 Recognition by EED. *Structure* 15, 1306-1315 (2007).

33. Neff, T. et al. Polycomb repressive complex 2 is required for MLL-AF9 leukemia. *Proceedings of the National Academy of Sciences* 109, 5028-5033 (2012).

34. Shi, J. et al. *The Polycomb complex PRC2 supports aberrant self-renewal in a mouse model of MLL-AF9;Nras (G12D) acute myeloid leukemia. Oncogene* (2012).doi: 10.1038/onc.2012.110

35. Walensky, L. D. Activation of Apoptosis in Vivo by a Hydrocarbon-Stapled BH3 Helix. *Science* 305, 1466-1470 (2004).

36. Walensky, L. D. et al. A Stapled BID BH3 Helix Directly Binds and Activates BAX. *Molecular Cell* 24, 199-210 (2006).

37. Moellering, R. E. et al. Direct inhibition of the NOTCH transcription factor complex. *Nature* 462, 182-188 (2009).

38. Bernal, F. et al. *A Stapled p53 Helix Overcomes HDMX-Mediated Suppression of p53. Cancer Cell* 18, 411-422 (2010).

39. Deshayes, S., Morris, M. C., Divita, G. & Heitz, F. Cell-penetrating peptides: tools for intracellular delivery of therapeutics. *Cell. Mol. Life Sci.* 62, 1839-1849 (2005).

40. Shen, X. et al. *EZH1* Mediates Methylation on Histone H3 Lysine 27 and Complements EZH2 in Maintaining Stem Cell Identity and Executing Pluripotency. *Molecular Cell* 32, 491-502 (2008).

41. Ezhkova, E. et al. EZH1 and EZH2 cogovern histone H3K27 trimethylation and are essential for hair follicle homeostasis and wound repair. *Genes & Development* 25, 485-498 (2011).

42. Margueron, R. et al. Ezh1 and Ezh2 Maintain Repressive Chromatin through Different Mechanisms. *Molecular Cell* 32, 503-518 (2008).

43. Borun, T. W., Pearson, D. & Paik, W. K. Studies of histone methylation during the HeLa S-3 cell cycle. *J. Biol. Chem.* 247, 4288-4298 (1972).

44. Byvoet, P., Shepherd, G. R., Hardin, J. M. & Noland, B. J. histone half-life. *Archives of Biochemistry and Biophysics* 148, 558-567 (2003).

45. Bracken, A. P. et al. The Polycomb group proteins bind throughout the INK4A-ARF locus and are disassociated in senescent cells. *Genes & Development* 21, 525-530 (2007).

46. Krivtsov, A. V. et al. Transformation from committed progenitor to leukaemia stem cell initiated by MLL-AF9. *Nature* 442, 818-822 (2006).

47. Toren, A. et al. CD133-positive hematopoietic stem cell 'sternness' genes contain many genes mutated or abnormally expressed in leukemia. *Stem Cells* 23, 1142-1153 (2005).

48. Suetsugu, A. et al. Characterization of CD133+ hepatocellular carcinoma cells as cancer stem/progenitor cells. Biochemical and Biophysical Research Communications 351, 820-824 (2006).

49. Singh, S. K. et al. Identification of human brain tumour initiating cells. *Nature* 432, 396-401 (2004).

50. Hambardzumyan, D., Squatrito, M., Squartro, M. & Holland, E. C. Radiation resistance and stem-like cells in brain tumors. *Cancer Cell* 10, 454-456 (2006).

51. Di Tullio, A., Vu Manh, T. P., Schubert, A., Månsson, R. & Graf, T. CCAAT/enhancer binding protein alpha (C/EBP(alpha))-induced transdifferentiation of pre-B cells into macrophages involves no overt retrodifferentiation. *Proceedings of the National Academy of Sciences* 108, 17016-17021 (2011).

52. Pinto do O, P. Hematopoietic progenitor/stem cells immortalized by Lhx2 generate functional hematopoietic cells in vivo. *Blood* 99, 3939-3946 (2002).

53. You, J. S. & Jones, P. A. Cancer genetics and epigenetics: two sides of the same coin? *Cancer Cell* 22, 9-20 (2012).

54. Tan, J. et al. Pharmacologic disruption of Polycomb-repressive complex 2-mediated gene repression selectively induces apoptosis in cancer cells. *Genes & Development* 21, 1050-1063 (2007).

55. Momparler, R. L., Idaghdour, Y., Marquez, V. E. & Momparler, L. F. Synergistic antileukemic action of a combination of inhibitors of DNA methylation and histone methylation. *Leuk. Res.* 36, 1049-1054 (2012).

56. Miranda, T. B. et al. DZNep is a global histone methylation inhibitor that reactivates developmental genes not silenced by DNA methylation. *Molecular Cancer Therapeutics* 8, 1579-1588 (2009).

57. Chiang, P. K. Biological effects of inhibitors of S-adenosylhomocysteine hydrolase. *Pharmacol. Ther* 77, 115-134 (1998).

58. Borchardt, R. T., Keller, B. T. & Patel-Thombre, U. Neplanocin A. A potent inhibitor of S-adenosylhomocysteine hydrolase and of vaccinia virus multiplication in mouse L929 cells. *J. Biol. Chem.* 259, 4353-4358 (1984).

59. Stewart, M. L., Fire, E., Keating, A. E. & Walensky, L. D. The MCL-1 BH3 helix is an exclusive MCL-1 inhibitor and apoptosis sensitizer. *Nature Chemical Biology* 6, 595-601 (2010).

60. Takada, K. et al. Targeted Disruption of the BCL9/β-Catenin Complex Inhibits Oncogenic Wnt Signaling. *Sci Transl Med* 4, 148ra1 17 (2012).

61. Bird, G. H. et al. Hydrocarbon double-stapling remedies the proteolytic instability of a lengthy peptide therapeutic. *Proceedings of the National Academy of Sciences* 107, 14093-14098 (2010).

62. Bowen, N. J., Fujita, N., Kajita, M. & Wade, P. A. Mi-2/NuRD: multiple complexes for many purposes. *Biochim. Biophys. Acta* 1677, 52-57 (2004).

63. Simon, J. A. & Kingston, R. E. Mechanisms of polycomb gene silencing: knowns and unknowns. *Nat Rev Mol Cell Biol* 10, 697-708 (2009).

64. Ho, L. & Crabtree, G R. Chromatin remodelling during development. *Nature* 463, 474-484 (2010).

65. Margueron, R. & Reinberg, D. The Polycomb complex PRC2 and its mark in life. *Nature* 469, 343-349 (2011).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An internally cross-linked polypeptide that inhibits the interaction between Enhancer of Zeste Homolog 2 (EZH2) and Embryonic Ectoderm Development (EED), the internally cross-linked polypeptide comprising the amino acid sequence FSSNRX$_1$KILX$_2$RTEILNQEWKQRRIQPV (SEQ ID NO:26), wherein X$_1$ and X$_2$ are each a non-natural amino acid with an olefinic side chain, and wherein the internally cross-linked polypeptide is cell penetrant.

2. The internally cross-linked polypeptide of claim 1, wherein X$_1$ and X$_2$ are each (S)-2-(4'-pentenyl) alanine (S5).

3. The internally cross-linked polypeptide of claim 2, wherein the internally cross-linked polypeptide consists of the amino acid sequence set forth in SEQ ID NO: 26.

4. A pharmaceutical composition comprising the internally cross-linked polypeptide of claim 3 and a pharmaceutically acceptable carrier.

5. The pharmaceutical composition of claim 4, further comprising an inhibitor of EZH2 enzymatic activity.

6. The pharmaceutical composition of claim 5, wherein the inhibitor of EZH2 enzymatic activity is GSK126.

7. A method of treating an EZH2-overexpressing or EZH2-dependent cancer in a human subject in need thereof, the method comprising administering to the human subject an effective amount of the internally cross-linked polypeptide of claim 1.

8. The method of claim 7, further comprising administering to the human subject an inhibitor of EZH2 enzymatic activity.

9. An internally cross-linked polypeptide that inhibits the interaction between Enhancer of Zeste Homolog 2 (EZH2) and Embryonic Ectoderm Development (EED), the internally cross-linked polypeptide comprising the amino acid sequence FSSNRX$_1$KILX$_2$RTQILNQEWKQRRIQPV (SEQ ID NO:27), wherein X$_1$ and X$_2$ are each a non-natural amino acid with an olefinic side chain, and wherein the internally cross-linked polypeptide is cell penetrant.

10. The internally cross-linked polypeptide of claim 9, wherein X$_1$ and X$_2$ are each (S)-2-(4'-pentenyl) alanine (S5).

11. The internally cross-linked polypeptide of claim 10, wherein the internally cross-linked polypeptide consists of the amino acid sequence set forth in SEQ ID NO: 27.

12. A pharmaceutical composition comprising the internally cross-linked polypeptide of claim 11, and a pharmaceutically acceptable carrier.

13. The pharmaceutical composition of claim 12, further comprising an inhibitor of EZH2 enzymatic activity.

14. The pharmaceutical composition of claim 13, wherein the inhibitor of EZH2 enzymatic activity is GSK126.

15. A method of treating an EZH2-overexpressing or EZH2-dependent cancer in a human subject in need thereof, the method comprising administering to the human subject an effective amount of the internally cross-linked polypeptide of claim 10.

16. The method of claim 15, further comprising administering to the human subject an inhibitor of EZH2 enzymatic activity.

17. The method of claim 16, wherein the inhibitor of EZH2 enzymatic activity is GSK126.

18. The method of claim 15, wherein the cancer is a leukemia, a breast cancer, a prostate cancer, a sarcoma, or a neuroblastoma.

19. A method of treating an EZH2-overexpressing or EZH2-dependent cancer in a human subject in need thereof, the method comprising administering to the human subject an effective amount of the pharmaceutical composition of claim 12.

20. The method of claim 19, further comprising administering to the human subject an inhibitor of EZH2 enzymatic activity.

21. The method of claim 20, wherein the inhibitor of EZH2 enzymatic activity is GSK126.

22. The method of claim 19, wherein the cancer is a leukemia, a breast cancer, a prostate cancer, a sarcoma, or a neuroblastoma.

23. An internally cross-linked polypeptide that inhibits the interaction between Enhancer of Zeste Homolog 2 (EZH2) and Embryonic Ectoderm Development (EED), the internally cross-linked polypeptide comprising the amino acid sequence FSSNRX$_1$KILX$_2$RTX$_3$ILNX$_4$EWKQRRIQPV (SEQ ID NO: 56), wherein X$_1$, X$_2$, X$_3$, and X$_4$ are each a non-natural amino acid with an olefinic side chain, and wherein the internally cross-linked polypeptide is cell penetrant.

24. The internally cross-linked polypeptide of claim 23, wherein X$_1$, X$_2$, X$_3$, and X$_4$ are each (S)-2-(4'-pentenyl) alanine (S5).

25. The internally cross-linked polypeptide of claim 23, wherein the internally cross-linked polypeptide consists of the amino acid sequence set forth in SEQ ID NO: 56.

26. A pharmaceutical composition comprising the internally cross-linked polypeptide of claim 25 and a pharmaceutically acceptable carrier.

27. The pharmaceutical composition of claim 26, further comprising an inhibitor of EZH2 enzymatic activity.

28. The pharmaceutical composition of claim 27, wherein the inhibitor of EZH2 enzymatic activity is GSK126.

29. A method of treating an EZH2-overexpressing or EZH2-dependent cancer in a human subject in need thereof, the method comprising administering to the human subject an effective amount of the internally cross-linked polypeptide of claim 23.

30. The method of claim 29, further comprising administering to the human subject an inhibitor of EZH2 enzymatic activity.

31. The method of claim 30, wherein the inhibitor of EZH2enzymatic activity is GSK126.

32. An internally cross-linked polypeptide that inhibits the interaction between Enhancer of Zeste Homolog 2 (EZH2) and Embryonic Ectoderm Development (EED), the internally cross-linked polypeptide comprising an amino acid sequence set forth in FSSNRX$_1$KILX$_2$RTEILNQEWKQRRIQPV (SEQ ID NO:26), except that one or more amino acids at positions 2, 3, 9, 13, 14, 17, 21 or 23 of SEQ ID NO: 26 are substituted, and wherein X$_1$, and X$_2$, are each a non-natural amino acid with an olefinic side chain, and wherein the internally cross-linked polypeptide is cell penetrant.

33. The internally cross-linked polypeptide of claim 32, wherein the amino acids at positions 13 and 17, are each substituted with a non-natural amino acid with an olefinic side chain.

34. The internally cross-linked polypeptide of claim 32, wherein the internally cross-linked polypeptide consists of an amino acid sequence set forth in SEQ ID NO:26, but with 1 to 6 amino acid substitutions at positions selected from the group consisting of positions: 2, 3, 9, 13, 14, 17, 21, and 23, of SEQ ID NO: 26.

35. The internally cross-linked polypeptide of claim 32, wherein the internally cross-linked polypeptide comprises an amino acid sequence set forth in SEQ ID NO: 26 but with 1 to 4 amino acid substitutions at positions 2, 3, 9, 13, 14, 17, 21 or 23.

36. The internally cross-linked polypeptide of claim 32, wherein the internally cross-linked polypeptide comprises an amino acid sequence set forth in SEQ ID NO: 26 but with 1 amino acid substitution at position 2, 3, 9, 13, 14, 17, 21 or 23.

37. The internally cross-linked polypeptide of claim 32, wherein the non-natural amino acid is S5 [(S)-2-4'-pentenyl) alanine].

38. A pharmaceutical composition comprising the internally cross-linked polypeptide of claim 32 and a pharmaceutically acceptable carrier.

39. The pharmaceutical composition of claim 38, further comprising an inhibitor of EZH2 enzymatic activity.

40. The pharmaceutical composition of claim 39, wherein the inhibitor of EZH2 enzymatic activity is GSK126.

41. A method of treating an EZH2-overexpressing or EZH2-dependent cancer in a human subject in need thereof, the method comprising administering to the human subject an effective amount of the internally cross-linked polypeptide of claim 32.

42. The method of claim 41, further comprising administering to the human subject an inhibitor of EZH2 enzymatic activity.

43. The method of claim 42, wherein the inhibitor of EZH2 enzymatic activity is GSK126.

* * * * *

UNITED STATES PATENT AND TRADEMARK OFFICE
CERTIFICATE OF CORRECTION

PATENT NO. : 10,308,926 B2
APPLICATION NO. : 14/772143
DATED : June 4, 2019
INVENTOR(S) : Loren D. Walensky et al.

Page 1 of 1

It is certified that error appears in the above-identified patent and that said Letters Patent is hereby corrected as shown below:

On the Title Page

Item (54) Title:
Delete "STABLIZED" and insert -- STABILIZED --, therefor.

In the Specification

Column 1, Line 1:
Delete "STABLIZED" and insert -- STABILIZED --, therefor.

Column 1, Line 16:
Delete "Mar. 14, 2014," and insert -- Mar. 13, 2014, --, therefor.

In the Claims

Column 82, Line 8:
In Claim 31, delete "EZH2enzymatic" and insert -- EZH2 enzymatic --, therefor.

Column 82, Line 26:
In Claim 34, delete "NO:26," and insert -- NO: 26 --, therefor.

Column 82, Line 28:
In Claim 34, delete "23," and insert -- 23 --, therefor.

Signed and Sealed this
Fifth Day of November, 2019

Andrei Iancu
*Director of the United States Patent and Trademark Office*